(12) United States Patent
Höpken et al.

(10) Patent No.: US 11,643,468 B2
(45) Date of Patent: May 9, 2023

(54) CHIMERIC ANTIGEN RECEPTORS AND CAR-T CELLS THAT BIND CXCR5 AND METHODS OF USE THEREOF TO TREAT MEDICAL DISORDERS

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Uta Höpken, Berlin (DE); Armin Rehm, Berlin (DE); Julia Bluhm, Berlin (DE); Wolfgang Uckert, Berlin (DE)

(73) Assignee: Max-Delbrück-Centrum für Molekulare Medizin in der Hemlholtz-Gemeinschaft, Berlin (DE)

(*) Notice: Subject to any disclaimer, the term of this patent is extended or adjusted under 35 U.S.C. 154(b) by 470 days.

(21) Appl. No.: 16/641,181

(22) PCT Filed: Aug. 23, 2018

(86) PCT No.: PCT/EP2018/072750
§ 371 (c)(1),
(2) Date: Feb. 21, 2020

(87) PCT Pub. No.: WO2019/038368
PCT Pub. Date: Feb. 28, 2019

(65) Prior Publication Data
US 2020/0216550 A1 Jul. 9, 2020

(30) Foreign Application Priority Data
Aug. 23, 2017 (EP) .................... 17187554

(51) Int. Cl.
| | | |
|---|---|---|
| *C07K 16/28* | (2006.01) |
| *A61K 35/17* | (2015.01) |
| *C07K 14/725* | (2006.01) |
| *C07K 14/705* | (2006.01) |
| *C12N 5/0783* | (2010.01) |
| *A61P 35/00* | (2006.01) |

(52) U.S. Cl.
CPC .......... *C07K 16/2866* (2013.01); *A61K 35/17* (2013.01); *A61P 35/00* (2018.01); *C07K 14/7051* (2013.01); *C07K 14/70521* (2013.01); *C12N 5/0636* (2013.01); *C12N 5/0646* (2013.01); *C07K 2317/24* (2013.01); *C07K 2317/565* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01)

(58) Field of Classification Search
CPC ............ C07K 16/2866; C07K 14/7051; C07K 14/70521; C07K 2317/24; C07K 2317/565; C07K 2319/02; C07K 2319/03; C07K 2319/33; A61K 35/17; A61P 35/00; C12N 5/0636; C12N 5/0646; C12N 2510/00
See application file for complete search history.

(56) References Cited

FOREIGN PATENT DOCUMENTS

| | | | |
|---|---|---|---|
| WO | WO 2016/090034 A2 | 6/2016 | |
| WO | WO 2016/164731 A2 | 10/2016 | |
| WO | WO-2018114578 A1 * | 6/2018 | ............. A61K 47/65 |
| WO | WO-2018114804 A1 * | 6/2018 | ......... A61K 39/3955 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Sengsayadeth S, et al. (2022) eJHaem. 3(Suppl.1):6-10. (DOI:10.1002/jha2.338).*
https://www.cancer.gov/about-cancer/treatment/research/car-t-cells (accessed from the internet Sep. 7, 2022).*
International Search Report and Written Opinion, PCT/EP2018/072750, dated Feb. 14, 2019.
Panjideh, Hossein, et al., "Immunotherapy of B-cell non-Hodgkin lymphoma by targeting the chemokine receptor CXCR5 in a preclinical mouse model", Int. J. Cancer: 135, No. 11, pp. 2623-2632 (Apr. 29, 2014).
Sadelain, Michael, et al., "The Basic Principles of Chimeric Antigen Receptor Design," Cancer Discovery, vol. 3, No. 4, pp. 388-398 (Apr. 2, 2013).
Batlevi, C. L. et al., "Novel immunotherapies in lymphoid malignancies", Nature Reviews, Clinical Oncology, 2016, vol. 13, pp. 25-40.

* cited by examiner

*Primary Examiner* — Robert S Landsman
(74) *Attorney, Agent, or Firm* — Knobbe, Martens, Olson & Bear, LLP

(57) ABSTRACT

An isolated chimeric antigen receptor polypeptide (CAR), wherein the CAR comprises an extracellular antigen-binding domain, comprising an antibody or antibody fragment that binds a human CXC chemokine receptor type 5 (CXCR5) protein. Also disclosed is a nucleic acid molecule encoding the CAR of the invention, a genetically modified immune cell, preferably a T cell, expressing the CAR of the invention and the use of said cell in the treatment of a medical disorder associated with the presence of pathogenic cells expressing CXCR5, preferably pathogenic mature B cells and/or memory B cells, and/or pathogenic T cells and/or T follicular helper cells, in particular mature B cell non-Hodgkin's lymphoma (B-NHL), T cell non-Hodgkin's lymphoma, or autoantibody-dependent autoimmune disease, preferably selected from systemic lupus erythematosus (SLE) or rheumatoid arthritis.

24 Claims, 16 Drawing Sheets
Specification includes a Sequence Listing.

Fig. 3

| | Leader | scFv | Order | Linker | Spacer | Trans-membrane domain | Co-stimulatory domain | Activation domain |
|---|---|---|---|---|---|---|---|---|
| H28 | Igk | humanized | VH-VL | Whitlow | IgG1 | CD28 | CD28 | CD3ζ |
| R28 | Igk | rat | VH-VL | Whitlow | IgG1 | CD28 | CD28 | CD3ζ |
| HBB1 | Igk | humanized | VH-VL | Whitlow | IgG1 | CD28 | 4-1BB | CD3ζ |
| HBB2 | Igk | humanized | VH-VL | Whitlow | IgG1Δ | CD8α | 4-1BB | CD3ζ |
| H28BB | Igk | humanized | VH-VL | Whitlow | IgG1 | CD28 | CD28 4-1BB | CD3ζ |

Fig. 4

Protein alignment of hHC and hLC
rat vs. human
89% homology between humanized and rat sequence (hHC)
93% homology between humanized and rat sequence (hLC)

VH
Sequence ID: Query_228957  Length: 113  Number of Matches: 1

Range 1: 1 to 113 Graphics
Score        Expect   Method                         Identities       Positives       Gaps
214 bits(546) 4e-79   Compositional matrix adjust.   101/113(89%)    112/113(99%)    0/113(0%)

Rat    1   EVQLVESGGGLVQPGKSLKLSCSASGFTFSTSGMHWFRQAPGKGLDWVAYISSSSGFVYA  60
           EVQLVESGGGLVQPG SL+LSC+ASGFTFSTSGM+WFRQAPGKGL+WV+YISSSSGFVYA
Human  1   EVQLVESGGGLVQPGGSLRLSCAASGFTFSTSGMNWFRQAPGKGLEWVSYISSSSGFVYA  60

Rat    61  DAVKGRFTISRDNAQNTLYLQLNSLKSEDTAIYYCARSEAAFWGQGTLVTVSS  113
           D+VKGRFTISRDNAQN+LYLQ+NSL++EDTA+YYCARSEAAFWGQGTLVTVSS
Human  61  DSVKGRFTISRDNAQNSLYLQMNSLRAEDTAVYYCARSEAAFWGQGTLVTVSS  113

VL
Sequence ID: Query_74585  Length: 112  Number of Matches: 1

Range 1: 1 to 112 Graphics
Score        Expect   Method                         Identities       Positives       Gaps
213 bits(542) 1e-78   Compositional matrix adjust.   104/112(93%)    108/112(96%)    0/112(0%)

Rat    1   DIVLTQAPRSVSVTPGESASISCRSNKSRLSRMGITPLNWYLQKPGKSPQLLIYRMSNLA  60
           DIVLTQ+PRS+ VTPGE ASISCRS+KSRLSRMGITPLNWYLQKPG+SPQLLIYRMSN A
Human  1   DIVLTQSPRSLPVTGEPASISCRSSKSRLSRMGITPLNWYLQKPGQSPQLLIYRMSNRA  60

Rat    61  SGVPDRFSGSGSETDFTLKISKVETEDVGVYYCAQFLEYPPTFGSGTKLEIK  112
           SGVPDRFSGSGS TDFTLKISKVETEDVGVYYCAQFLEYPPTFGSGTKLEIK
Human  61  SGVPDRFSGSGSGTDFTLKISKVETEDVGVYYCAQFLEYPPTFGSGTKLEIK  112

Fig. 5 hHC Alterations
Sequence was codon optimized for *homo sapies*
90% homology to original sequence after codon optimization (CO)

VH
Sequence ID: Query_122263  Length: 339  Number of Matches: 1

Range 1: 1 to 333 Graphics

| Score | Expect | Identities | Gaps | Strand |
|---|---|---|---|---|
| 433 bits(234) | 4e-126 | 301/334(90%) | 2/334(0%) | Plus/Plus |

```
Original   1    GAGGTGCAGCTGGTGGAGAGC-GGCGGCGGCCTGGTGCAGCCCGGCGGCAGCCTGAGGCT   59
CO         1    GAGGTGCAGCTGGTGGA-ATCTGGCGGAGGACTGGTGCAGCCTGGCGGCTCTCTGAGACT   59

Original   60   GAGCTGCGCCGCCAGCGGCTTCACCTTCAGCACCAGCGGCATGAACTGGTTCAGGCAGGC   119
CO         60   GTCTTGTGCCGCCAGCGGCTTCACCTTCAGCACCAGCGGCATGAACTGGTTCAGACAGGC   119

Original   120  CCCCGGCAAGGGCCTGGAGTGGGTGAGCTACATCAGCAGCAGCGGCTTCGTGTACGC    179
CO         120  CCCTGGCAAGGGCCTGGAATGGGTGTCCTACATCAGCAGCAGCTCCGGCTTCGTGTACGC   179

Original   180  CGACAGCGTGAAGGGCAGGTTCACCATCAGCAGGGACAACGCCCAGAACAGCCTGTACCT   239
CO         180  CGACAGCGTGAAGGGCCGGTTCACCATCAGCAGAGACAACGCCCAGAACAGCCTGTACCT   239

Original   240  GCAGATGAACAGCCTGAGGGCCGACGACACCGCCGTGTACTACTGCGCCAGGAGCGACGC   299
CO         240  GCAGATGAACTCCCTGCGGGCCGACGACACCGCCGTGTACTACTGTGCCAGAAGCGAGGC   299

Original   300  CGCCTTCTGGGGCCAGGGCACCCTGGTGACCGTG   333
CO         300  CGCCTTTTGGGGCCAGGGAACACTCGTGACAGTG   333
```

Fig. 6 hLC Alterations
Sequence was codon optimized for *homo sapies*
89% homology to original sequence after codon optimization (CO)

VL
Sequence ID: Query_71369  Length: 336  Number of Matches: 1

Range 1: 1 to 336  Graphics

| Score | Expect | Identities | Gaps | Strand |
|---|---|---|---|---|
| 411 bits(222) | 2e-119 | 298/336(89%) | 0/336(0%) | Plus/Plus |

```
Original    1   GACATCGTGCTGACCCAGAGCCCCCGCAGCCTGCCCGTGACCCCCGGCGAGCCCGCCAGC   60
                ||||||||||||||||||||||||||| |  |||||  ||||||||  ||||||||||||
CO          1   GATATCGTGCTGACCCAGAGCCCCAGATCCCTGCCTGTGACACCTGGCGAGCCTGCCAGC   60

Original    61  ATCAGCTGCAGGTCCTCCAAGTCCAGGCTGAGCAGGATGGGCATCACCCCCCTGAACTGG   120
                ||||||||||   |  |||   ||||||||||||  ||||||||||||||||||||||||
CO          61  ATCAGCTGCAGAAGCAGCAAGAGCCGGCTGAGCCGGATGGGCATCACCCCCCTGAACTGG   120

Original    121 TACCTGCAGAAGCCCGGCCAGAGCCCCCAGCTGCTGATCTACAGGATGAGCAACAGGGCC   180
                || |||||||| || |||||||| ||||||||||||||||||| |||||||||||| ||
CO          121 TATCTGCAGAAACCCGGCCAGTCCCCCCAGCTGCTGATCTACCGGATGAGCAACAGAGCC   180

Original    181 AGCGGCGTGCCCGACAGGTTCAGCGGCAGCGGCAGCGGCACCGACTTCACCCTGAAGATC   240
                |||||||||||||||  || |||||||||| ||||||||||||||||||||||||||||
CO          181 AGCGGCGTGCCCGATAGATTTTCCGGCTCTGGAAGCGGCACCGACTTCACCCTGAAGATC   240

Original    241 AGCAAGGTGGAGACCGAGGACGTGGGCGTGTACTACTGCGCCCAGTTCCTGGAGTAcccc   300
                |||||||||||| ||||||||||||||||||||| |||||||||||||||||| |||||
CO          241 AGCAAGGTGGAAACCGAGGACGTGGGCGTGTACTATTGCGCCCAGTTCCTGGAATACCCC   300

Original    301 cccACCTTCGGCAGCGGCACCAAGCTGGAGATCAAG   336
                ||||||||| ||||||||||||||||||||| |||||
CO          301 CCCACCTTTGGCAGCGGCACCAAGCTGGAAATCAAG   336
```

GeneArt plasmids: humanized (left) and Rat (right)

CHIMERIC ANTIGEN RECEPTORS AND CAR-T CELLS THAT BIND CXCR5 AND METHODS OF USE THEREOF TO TREAT MEDICAL DISORDERS

RELATED APPLICATIONS

This application is a U.S. National Phase of International Application No. PCT/EP2018/072750, filed Aug. 23, 2018, designating the U.S. and published in English on Feb. 28, 2019, as WO 2019/038368 A1, which claims the benefit of European application No. 17187554.5, filed Aug. 23, 2017.

FIELD

The invention relates to an isolated chimeric antigen receptor polypeptide (CAR), wherein the CAR comprises an extracellular antigen-binding domain, comprising an antibody or antibody fragment that binds a CXC chemokine receptor type 5 (CXCR5) protein. The invention further relates to a nucleic acid molecule encoding the CAR of the invention, a genetically modified immune cell, preferably a T cell, expressing the CAR of the invention and the use of said cell in the treatment of a medical disorder associated with the presence of pathogenic cells expressing CXCR5, preferably pathogenic mature B cells and/or memory B cells, and/or pathogenic T cells and/or T follicular helper cells, in particular mature B cell non-Hodgkin's lymphoma (B-NHL), T cell non-Hodgkin's lymphoma, or autoantibody-dependent autoimmune disease, preferably selected from systemic lupus erythematosus (SLE) or rheumatoid arthritis.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32274238_1.TXT, the date of creation of the ASCII text file is Feb. 21, 2020, and the size of the ASCII text file is 82.2 KB.

BACKGROUND OF THE INVENTION

B-NHLs are heterogenous and can be distinguished by an aggressive and indolent course. The standard of care is typically combined antibody/chemotherapy, either alone or in combination with autologous stem cell transplantation, immunomodulatory drugs, irradiation, proteasome inhibitors, signaling pathway inhibitors, and for very few patients allogeneic stem cell transplantation applies. Because in many B-NHL entities the median age at diagnosis is >66-72 years, co-morbidities also exist that preclude intense and extended chemotherapies or even allogeneic bone marrow transplantations.

Inhibitors of B cell receptor (BCR) signaling in mature B cell lymphomas, foremost ibrutinib and others, have brought about a tremendous advance in remission rates. Despite initial high sensitivity to these class of kinase inhibitors, it is uncertain whether tumor eradication can be achieved and secondly, several studies revealed that clonal lymphoma and leukemia evolution led to the occurrence of resistance to Bruton tyrosine kinase (BTK) inhibition. Thus, the rapid emergence of secondary resistances to targeted therapies demonstrates the urgent need to find a solution for tolerable salvage therapies, applicable in particular to patients having received several lines of other chemotherapies and thus, with a reduced clinical performance (IPI score).

Adoptive chimeric antigen receptor (CAR)-T cell therapies targeted at the broadly expressed CD19 antigen on leukemia and lymphoma B cells has brought about substantial clinical efficacy and currently, more than 40 CD19 CAR-T cell studies are registered at the FDA for the treatment of B-NHL and B-ALL (www-clinicaltrials.gov). However, in anti-CD19 antibody or CAR-T cell therapies directed against B-NHL, resistance can occur due to antigen loss. A recent study showed that upon anti-CD19 CAR-T cell therapy, escape variants emerged that resulted from the selection for alternatively spliced CD19 isoforms and thus, loss of the cognate CD19 CAR epitope.

Thus, CXCR5 emerges as an alternative target for immunotherapy of B-cell lymphomas besides existing therapeutic mAbs or CAR-T cell therapies.

B cell derived lymphoproliferative disorders with distinctive nodal lodging, such as acute lymphoblastic leukemia (B-ALL), chronic lymphocytic leukemia (CLL), follicular lymphoma (FL), mantle cell lymphoma (MCL), diffuse large B-cell lymphoma (DLBCL) frequently express the homeostatic chemokine receptor CXCR5. CXCR5 is physiologically expressed on mature recirculating B cells and on a small subset of CD4+ T cells, the follicular T-helper cells (Tfh) and regulates their homeostatic trafficking and homing to B-cell follicles within secondary lymphoid organs. Importantly, CXCR5 is not expressed on B cell precursors within the bone marrow (BM), neither do plasma cells express this receptor.

To the knowledge of the inventors, no alternative anti-CXCR5 CAR constructs have been previously described, and no anti-CXCR5 antibody studies relevant to the medical approach of the present invention are currently available.

Panjideh et al (International Journal of Cancer, vol. 135, no. 11, 29 Apr. 2014) describes the use of a CXCR5 bi-specific antibody for the treatment of non-Hodgkin's lymphoma. Sadelain et al (Cancer Discovery, vol. 3, no. 4, 1 Apr. 2013) present a review of various CAR technologies, without reference to CXCR5. WO 2016/090034 discloses multiple possible targets for CAR constructs. CD185 (CXCR5) is mentioned, without any details regarding CAR components, medical uses or any reference to the relevance of the target. WO 2016/164731 describes the use of CAR-T cells directed against various B cell target antigens. CXCR5 is not mentioned as a CAR T target.

Alternative therapies for medical conditions such as those described above are in development or have been recently established, for example anti-CD19 CAR constructs, standard therapies such as cytotoxic chemotherapies, corticosteroids, immunomodulators like IMIDs, proteasome inhibitors, autologous stem cell transplantation, allogeneic stem cell transplantation, signaling inhibitors, and antibodies directed against CD20, Rituximab, and anti-CD19, Oletuzumab and with bispecific antibodies (BITE), comprised of an Fab fragment targeting CD19 and an anti-CD3 fragment (Blinatumomab).

Although a number of potential alternative therapies are in development for diseases of pathogenic B and T cells, a significant need remains for providing effective means for addressing such medical disorders.

SUMMARY OF THE INVENTION

In light of the prior art the technical problem underlying the invention was the provision of an agent suitable for treating diseases associated with pathogenic B cells and/or T cells, in particular non-Hodgkin's lymphoma or autoantibody-dependent autoimmune diseases.

This problem is solved by the features of the independent claims. Preferred embodiments of the present invention are provided by the dependent claims.

Therefore, the invention relates to a chimeric antigen receptor polypeptide (CAR), comprising:
 i. an extracellular antigen-binding domain, comprising an antibody or antibody fragment that binds CXC chemokine receptor type 5 (CXCR5) protein,
 ii. a transmembrane domain, and
 iii. an intracellular domain.

The present invention therefore relates to an anti-CXCR5 CAR construct and corresponding immune cells expressing said construct, preferably a CAR-T cell product that confers human T cells with a high cytotoxic activity against defined, mature B-NHLs, while sparing normal hematopoietic cells such as T cells (except for Tfh or other T cell lymphomas described herein), plasma B cells and their bone marrow precursors. In preferred embodiments all myeloid cells and NK cells are likewise spared; as the CAR-T cell product of the present invention shows no activity against these cells.

In preferred embodiments of the immunotherapy approach of the present invention, patient-derived T cells are transduced, preferably retrovirally, to express an artificial immune receptor as described herein, composed of an extracellular antibody-derived antigen recognition part, fused to a transmembrane section, and followed by intracellular signaling domains. The construct described herein therefore confers transduced T cells with anti-tumor cytolytic capacity.

Due to the preferred autologous transfer of T cells, a graft-versus-host-disease cannot occur upon treatment with the CAR-Ts of the present invention. Memory T cell formation, which is important for the prevention of a relapse, can develop.

Such mature B-NHL entities include, but are not limited to, certain stages of follicular lymphoma, diffuse large B-cell lymphoma, mantle cell lymphoma, and chronic lymphocytic leukemia.

For the first time, the anti-CXCR5 CAR-T cells will enable targeting of the tumor cells in the tumor microenvironment, because lymphoma growth-promoting Tfh cells will be eradicated concomitantly. Tumor cells within a given tumor entity are homogenously positive for the target antigen CXCR5, thus precluding unwanted positive selection of low/non-expressing tumor cells.

The anti-CXCR5 CAR-T cell described herein is in preferred embodiments applicable to the treatment of mature B-NHL patients who are not eligible for other therapies. More specifically, embodiments of the invention relate to the treatment of the following patient collectives:
 i) patients with multidrug resistances,
 ii) patients not eligible for allogeneic stem cell transplantation,
 iii) patients with co-morbidities that preclude further chemotherapies,
 iv) aged patients who do not tolerate chemotherapies,
 v) the CAR is applicable for salvage therapies even after progressive disease and multiple lines of other standard of care therapies have failed,
 vi) it is applicable even at low antigen density on target tumor cells, where antibodies can fail, and/or
 vii) it is applicable as a monotherapy which is not the case for antibodies.

The anti-CXCR5 CAR described herein confers high avidity to T cells, necessary for anti-tumor efficacy. It has been demonstrated that the anti-CXCR5 CAR of the present invention does not confer T cell-reactivity against physiological plasma B cells, T cells (except for Tfh cells and specific pathological CXCR5-expressing T-cells), NK cells, all myeloid cell lineages and their precursors. Thus, the present invention has an unprecedented low off-target reactivity on other hematopoietic tissues.

In contrast to anti-CD19 CAR-T cells, the anti-CXCR5 CAR of the present invention has no unwanted reactivity against immature B-NHLs, precursor B-cell neoplasia or physiological benign B-cell precursors.

As demonstrated in the examples below, in an in vitro co-culture system, anti-CXCR5 CAR-T cells become activated upon exposure to CXCR5-expressing human B-NHL tumor cell lines. These T cells then develop an effector phenotype with high level secretion of IFN-gamma, a phenotype that is predictive of a cytotoxic activity.

Additionally, a cytotoxicity assay (51Cr-release) against selected target cell lines, B-NHL, B and T cell leukemia, CXCR5-negative cells and CXCR5-transfectants, shows that selective cellular cytotoxicity is obtained only in cell lines positive for CXCR5.

Additional pre-clinical testing encompasses i) in vitro cytotoxicity testing against suitable B-NHL cell lines from patients, and ii) in vivo testing of anti-CXCR5 CAR activity against xenotransplanted B-NHL cell lines.

As such, the CAR of the present invention represents a surprising and beneficial approach towards the treatment of the medical conditions described herein. The employment of anti-CXCR5 CARs has not been previously attempted or described as a promising approach towards treating NHL. The minimal (if not non-existent) unwanted side effects, due to the selectivity of the marker, also represent a beneficial and surprising aspect of the present invention. In particular in patients, in which resistance to anti-CD19 treatments have arisen, the present invention represents a very promising approach towards eradication of malignancies.

In one embodiment, the invention relates to a chimeric antigen receptor (CAR) polypeptide as described herein, wherein when said CAR is expressed in a genetically modified immune cell, preferably a T lymphocyte, said immune cell binds CXCR5 on the surface of a CXCR5-expressing cell and is activated, thereby inducing cytotoxic activity against said CXCR5-expressing cell.

Examples of CXCR5-expressing cells are known to a skilled person, and can be identified by further screening of cancers or other pathogenic cells. Cell lines expressing CXCR5 are preferably DOHH-2, OCI-Ly7, SU-DHL4, JeKo-1, JVM-3, MEC-1 and/or SC-1.

In one embodiment, the invention relates to a chimeric antigen receptor polypeptide (CAR), comprising:
 an extracellular antigen-binding domain, comprising an antibody or antibody fragment that binds CXC chemokine receptor type 5 (CXCR5) protein, wherein said antibody or antibody fragment comprises VH and VL domains of a single chain antibody fragment, wherein preferably a linker polypeptide is positioned between the VH and VL domains, wherein said linker is preferably configured to not interfere with the antibody fragment-CXCR5 antigen interaction;
 a spacer polypeptide (also referred to as a hinge) positioned between the extracellular antigen-binding domain and a transmembrane domain, wherein said spacer polypeptide is preferably configured to not interfere with the antibody fragment-CXCR5 antigen interaction and/or with T cell activation when said CAR is expressed in a T cell expressing said CAR;

a transmembrane domain, wherein said transmembrane domain is preferably configured to not interfere with the antibody fragment-CXCR5 antigen interaction and/or with T cell activation when said CAR is expressed in a T cell expressing said CAR;

and an intracellular domain, wherein said intracellular domain comprises a co-stimulatory domain and a signalling domain, wherein said intracellular domain is preferably configured to provide signals to stimulate T cell activation upon binding to the CXCR5 target, for example by increasing cytokine production and/or facilitating T cell replication, thus leading to cytotoxic effect.

The CAR of the present invention may therefore employ various formats, comprising potentially different protein sequences for each of the functional domains described herein. A skilled person is capable of selecting and testing the desired function of the CARs, for example based on the experimental approaches demonstrated in the examples below. As such, the election of any given specific protein sequence to be used in the CAR of the invention, in any of the functional domains discussed herein, can be assessed by a skilled person using routine methods for functional efficacy. For example, various linker polypeptide sequences positioned between the VH and VL domains, various spacer polypeptide sequences (also referred to as a hinge) positioned between the extracellular antigen-binding domain and a transmembrane domain, various transmembrane domains and various intracellular domains, preferably comprising co-stimulatory and signalling domains, may be employed.

In embodiments of the invention, the CAR, and each of the elements or domains mentioned herein, are configured to not detrimentally interfere with the antibody fragment-CXCR5 antigen interaction, to not detrimentally interfere with T cell activation when said CAR is expressed in a T cell expressing said CAR, and to not detrimentally interfere with the CAR providing signals to stimulate T cell activation upon binding to the CXCR5 target.

Experimental approaches are described herein for assessing these properties of a CXCR5 CAR, such that the invention is considered to encompass various functional sequence variants and combinations of domains of the types described herein, without being limited to the particular sequences disclosed by way of example in the following. For example, specific activation of CAR-T cells of the present invention by CXCR5-expressing tumor cells can be demonstrated by the release of IFN-gamma, IL-2 and TNF-alpha, as shown below.

To the knowledge of the inventors, the present invention relates to the first described CXCR5 CAR, and first functional evidence of a desired therapeutic effect of a CXCR5 CAR in a medical setting. Alone the provision of a CXCR5 CAR, independent of the particular sequences employed in the various functional domains described herein, represents a significant and beneficial breakthrough in treating the many diseases associated with pathogenic mature B cells and/or memory B cells, and/or pathogenic T cells and/or T follicular helper cells.

Embodiments Relating to the Antigen-Binding Domain of the CAR:

In one embodiment, the invention relates to a chimeric antigen receptor (CAR) polypeptide as described herein, wherein the antigen-binding domain comprises a variable heavy chain (VH), said VH comprising:

a heavy chain complementary determining region 1 (H-CDR1) with at least 80% sequence identity to SEQ ID NO 1 (GFTFSTSG), a heavy chain complementary determining region 2 (H-CDR2) with at least 80% sequence identity to SEQ ID NO 2 (ISSSSGFV), and a heavy chain complementary determining region 3 (H-CDR3) with at least 80% sequence identity to SEQ ID NO 3 (ARSEAAF), and a variable light chain (VL), said VL comprising:

a light chain complementary determining region 1 (L-CDR1) with at least 80% sequence identity to SEQ ID NO 4 (KSRLSRMGITP), a light chain complementary determining region 2 (L-CDR2) with at least 66% sequence identity to SEQ ID NO 5 (RMS), and a light chain complementary determining region 3 (L-CDR3) with at least 80% sequence identity to SEQ ID NO 6 (AQFLEYPPT).

In one embodiment, the invention relates to a chimeric antigen receptor (CAR) polypeptide as described herein, comprising a VH domain that comprises CDR sequences of SEQ ID NO. 1, SEQ ID No. 2 and SEQ ID NO. 3, and a VL domain that comprises CDR sequences of SEQ ID NO. 4; SEQ ID NO 5, and SEQ ID NO. 6.

In preferred embodiments, the sequence variants with 80% or more sequence identity to the specific CDR sequences of SEQ ID 1-6 maintain CXCR5 binding with essentially the same or similar functional properties as VH and VL domains with the specific CDR sequences of SEQ ID NO 1-6, i.e. the CXCR5 binding is essentially the same or similar with respect to affinity, specificity and epitope binding mode.

The amino acid sequence of the scFV fragment was obtained originally from a rat-anti-human CXCR5 antibody and has been modified with respect to multiple improvements, for example by humanization of the VL and VH chains, in order to allow folding and expression in the context of a transmembrane receptor structure.

Furthermore, the order of the light and heavy chain fragments may be inverted upon the desired configuration of the antigen binding fragment.

Additionally, in some embodiments the linker sequence between heavy and light chains has been modified, for example by shortening, in order to enhance the CAR function.

Additionally, the nucleic acid sequence encoding the CAR has been codon-optimized in order to improve expression of the CAR.

These modifications enable sufficient surface expression on T cells and still maintain proper antigen binding. High affinity and high avidity enable CAR-T cells to i) recognize, ii) be activated against, and iii) kill tumor target cells with high, intermediate or low CXCR5 surface expression.

To the knowledge of the inventors, neither anti-CXCR5 CARs nor humanized anti-CXCR5 antibodies have been previously described in the art.

Due to the high affinity and avidity of the antigen-binding domain of the anti-CXCR5 CAR-T cell described herein, even low CXCR5-expressing mature B-NHLs can be recognized, allowing for T cell activation and tumor cell killing.

The anti-CXCR5 CAR-T cell product described herein is characterised by unique properties.

The anti-CXCR5 CAR as described herein has a high affinity and confers high specificity and avidity to T cells. These properties enable CAR-T cells to i) recognize, ii) be activated against, and iii) kill tumor target cells with high and low CXCR5 surface expression.

The number of CXCR5 antigens expressed on the surfaces of tumor cells can be quantified by using an anti-CXCR5 antibody coupled to a fluorescent-dye in conjunction with Quantibrite beads (from Becton Dicksinson). The preferred method applied to quantify CXCR5 antigens expressed on the surfaces of tumor cells is "fluorescence activated cell sorting/cell analysis" (FACS). Fluorescence intensity of beads correlates exactly with the numbers of fluorescent antibodies bound to cells, and this is a measure for the number of CXCR5 molecules on cells.

The VH and VL fragments described herein may be arranged in multiple configurations in the CAR and still maintain high specificity and high affinity for the target epitope. In some embodiments, the CAR may be configured in the VH-VL or VL-VH configuration, with variation in the linker, hinge, transmembrane domain, co-stimulatory domain and/or activation domains, and still maintain its efficacy. This surprising feature of the invention enables greater flexibility in the design of CARs directed against CXCR5, thereby enabling further modification and/or optimization of the CAR structure on the basis of the VH and VL domains described herein, if any further development should be necessary or desired.

Sequence alignments of the rat and humanized sequences are shown in FIG. 4. Accordingly, the sequences below also encompass generalized sequences representing both rat and humanized forms of the antigen-binding domains. In the sequence below, each X represents a potential amino acid change. Preferred amino acid substitutions are those described for each of the potentially altered positions.

All possible combinations of potential modifications for any given potentially variant residue proposed herein (as identified by X in the "generalized sequences") are encompassed by the present invention. By combining one or more of these various substitutions, humanized variants may be generated that exhibit the desired binding properties of the rat antigen-binding domain demonstrated herein. The CARs or parts thereof described herein also encompass a sequence with at least 70%, 80%, preferably 90%, sequence identity to those humanized sequences disclosed explicitly or disclosed through a sequence formula.

In one embodiment, the invention relates to a chimeric antigen receptor (CAR) polypeptide as described herein, comprising a VH domain with at least 70%, 80% sequence identity, preferably at least 85%, 90%, 95% or with 100% sequence identity, to SEQ ID NO 7:

```
EVQLVESGGGLVQPGX1SLX2LSCX3ASGFTFSTSGMX4WFRQAPGKGLX
5WVX6YISSSSGFVYADX7VKGRFTISRDNAQNX8LYLQX9NSLX10X11
EDTAX12YYCARSEAAFWGQGTLVTVSS,
``` wherein X1-X12 may be any amino acid, preferably X1: G or K, X2: R or K; X3: A or S; X4: N or H; X5: E or D; X6: S or A; X7: S or A; X8: S or T; X9: M or L; X10: R or K, X11: A or S; X12: V or I;

and a VL domain with at least 80% sequence identity, preferably at least 85%, 90%, 95% or with 100% sequence identity, to SEQ ID NO 8:

```
DIVLTQX1PRSX2PVTPGEX3ASISCRSX4KSRLSRMGITPLNWYLQKPG
X5SPQLLIYRMSNX6ASGVPDRFSGSGSX7TDFTLKISKVETEDVGVYYC
AQFLEYPPTFGSGTKLEIK,
``` wherein X1-X7 may be any amino acid, preferably X1: S or A; X2: L or V; X3: P or S; X4: S or N; X5: Q or K; X6: R or L; X7: G or E.

In preferred embodiments, the sequence variants with 80% or more sequence identity to the specific VH and VL sequences listed herein maintain CXCR5 binding with essentially the same or similar functional properties as VH and VL domains with the specific sequences recited herein, i.e. the CXCR5 binding is essentially the same or similar with respect to affinity, specificity and epitope binding mode.

In one embodiment, the invention relates to a chimeric antigen receptor (CAR) polypeptide as described herein, comprising

```
a VH domain according to
                                    SEQ ID NO 9
(EVQLVESGGGLVQPGGSLRLSCAASGFTFSTSGMNWFRQAPGKGLEWVS

YISSSSGFVYADSVKGRFTISRDNAQNSLYLQMNSLRAEDTAVYYCARSE

AAFWGQGTLVTVSS),
or

SEQ ID NO 10
(EVQLVESGGGLVQPGKSLKLSCSASGFTFSTSGMHWFRQAPGKGLDWVA

YISSSSGFVYADAVKGRFTISRDNAQNTLYLQLNSLKSEDTAIYYCARSE

AAFWGQGTLVTVSS)
and a VL domain according to

SEQ ID NO 11
(DIVLTQSPRSLPVTPGEPASISCRSSKSRLSRMGITPLNWYLQKPGQSP

QLLIYRMSNRASGVPDRFSGSGSGTDFTLKISKVETEDVGVYYCAQFLEY

PPTFGSGTKLEIK),
or

SEQ ID NO 12
(DIVLTQAPRSVSVTPGESASISCRSNKSRLSRMGITPLNWYLQKPGKSP

QLLIYRMSNLASGVPDRFSGSGSETDFTLKISKVETEDVGVYYCAQFLEY

PPTFGSGTKLEIK).
```

In further embodiments, the invention relates to a chimeric antigen receptor (CAR) polypeptide that comprises one or more linker, spacer, transmembrane, and signaling domains. In one embodiment, the CAR comprises an intracellular domain, which comprises a co-stimulatory domain and a signalling (activation) domain.

In one embodiment, the invention relates to a chimeric antigen receptor (CAR) polypeptide as described herein, wherein the extracellular antigen-binding domain comprises a linker polypeptide positioned between the VH and VL domains, wherein said linker is preferably selected from

```
a Whitlow
(SEQ ID NO 13; GSTSGSGKPGSGEGSTKG),
or

Gly-Ser
(SEQ ID NO 14; SSGGGGSGGGGSGGGGS)
linker,
``` linkers with at least 80% sequence identity to SEQ ID NO 13 or 14.

In one embodiment, the invention relates to a chimeric antigen receptor (CAR) polypeptide as described herein, comprising additionally a spacer polypeptide positioned between the extracellular antigen-binding domain and the transmembrane domain, wherein said spacer is selected from:

IgG1 spacer
(SEQ ID NO 15; PAEPKSPDKTHTCPPCPAPPVAGPSVFLFPPKPKD

TLMIARTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGKKD

PK),

IgG1Δ spacer
(SEQ ID NO 16; PAEPKSPDKTHTCPPCPAPPVAGPSVFLFPPKPKD

TLMIARTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSSLSPGK

K),

IgG4 (Hi-CH2-CH3) spacer
(SEQ ID NO 17; ESKYGPPCPPCPAPEFEGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK),

IgG4 (Hi-CH3) spacer
(SEQ ID NO 18; ESKYGPPCPPCPGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK),

IgG4 (Hi) spacer
(SEQ ID NO 19; ESKYGPPCPPCP), or a spacer with at least 80% sequence identity to any one of SEQ ID NO 15 to 19.

In one embodiment, the invention relates to a chimeric antigen receptor (CAR) polypeptide as described herein, wherein the transmembrane domain is selected from:

a CD8α domain
(SEQ ID NO 20; IYIWAPLAGTCGVLLLSLVITLYC),
or a CD28 domain
(SEQ ID NO 21; FWVLVVVGGVLACYSLLVTVAFIIFWV), transmembrane domains with at least 80% sequence identity to SEQ ID NO 20 or 21.

In one embodiment, the invention relates to a chimeric antigen receptor (CAR) polypeptide as described herein, wherein the intracellular domain comprises:

a co-stimulatory domain selected from a 4-1BB co-stimulatory domain
(SEQ ID NO 22; KRGRKKLLYIFKQPFMRPVQTTQEEDGCSCRFPEE EEGGCEL),
and/or a CD28 co-stimulatory domain
(SEQ ID NO 23; RSKRSRLLHSDYMNMTPRRPGPTRKHYQPYAPPRD

FAAYRSL), or
a co-stimulatory domain comprising both a 4-1BB (SEQ ID NO 22) and a CD28 co-stimulatory domain (SEQ ID NO 23) arranged adjacently, or
a co-stimulatory domain with at least 80% sequence identity to SEQ ID NO 22 or 23.

In one embodiment, the invention relates to a chimeric antigen receptor (CAR) polypeptide as described herein, comprising additionally a signaling domain (otherwise known as an activation domain), wherein said signaling domain is a CD3zeta (4-1BB or CD28) signaling domain
(SEQ ID NO 24; LRVKFSRSADAPAYQQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR), or
a signaling domain with at least 80% sequence identity to SEQ ID NO 24.

In one embodiment, the invention relates to a chimeric antigen receptor (CAR) polypeptide as described herein, comprising a sequence according to any one of SEQ ID NO 25, 26, 27, 28 or 29.

The exchange of signaling domains meets the demands for either a strong and rapid effector phase (CD28 co-stimulatory domain), or a long-lasting relapse control as secured by a T cell memory population (4-1BB signaling domain). As demonstrated herein, the various signaling domains may be exchanged in multiple configuration, providing a CAR with flexibility with respect to its design without loss of the advantageous binding properties.

In further embodiments of the invention, the CAR may comprise the following configurations:
H28: MP71-hCXCR5-VH-Whitlow-VL-IgG1-CD28-CD28-CD3z
R28: MP71-ratCXCR5-VH-Whitlow-VL-IgG1-CD28-CD28-CD3z
HBB1: MP71-hCXCR5-VH-Whitlow-VL-IgG1Δ-CD8α-4-1BB-CD3z
HBB2: MP71-hCXCR5-VH-Whitlow-VL-IgG1-CD28-4-1BB-CD3z
H28BB: MP71-hCXCR5-VH-Whitlow-VL-IgG1-CD28-CD28-4-1BB-CD3z The particular configurations are intended as preferred but non-limiting embodiments. The configurations above are also not intended to be limited by the specific sequences of those embodiments described herein. Sequence variation, in the context of these configurations, is possible and is encompassed by the scope of the present invention.

Due to the variants (by adding alternative components) employed as the linker, spacer, transmembrane and intracellular domains, it becomes apparent that the various components may be exchanged at required by the skilled person, and the CXCR5 binding properties may be maintained, thereby maintaining the desired biological effects.

In preferred embodiments, in combination with the MP71-vector and a gamma-retrovirus expression system, an unusually high transduction rate for human T cells can be achieved. The transduction system is variable due to a modular design of the CAR construct, meaning that lentiviruses as well as transposons can be employed, depending on the needs and preferences of the skilled person when carrying out the invention. Transfer of the genetic information/nucleic acid molecule for the CXCR5 CAR also includes CrispR/Cas and TALEN mediated insertion into target cell lines, preferably T lymphocytes, Natural Killer Cells, and induced pluripotent stem cells, iPS. All suitable methods for transferring the genetic information/nucleic acid molecule for the CXCR5 CAR into the cell expressing said CAR are encompassed by the present invention, and a suitable method may be selected by a skilled person when carrying out the invention. For example, multiple methods of transforming T cells are known in the art, including any given viral-based gene transfer method, such as those based on modified Retroviridae, and non-viral methods such as DNA-based transposons and direct transfer of mRNA by electroporation.

Additionally, the signaling components of the CAR construct have been exchanged in a three step cloning procedure that allows for a modular composition, and tailor-made construction by a skilled person, of clinically applicable anti-CXCR5 CARs.

In a further aspect of the invention, the invention relates to an isolated nucleic acid molecule, preferably in the form of a vector, such as a viral vector or a transposon vector, preferably a sleeping beauty vector, selected from the group consisting of:
a) a nucleic acid molecule comprising a nucleotide sequence
which encodes a chimeric antigen receptor (CAR) polypeptide according to any embodiment of the CAR described herein,
which encodes an extracellular antigen-binding domain, a transmembrane domain, and an intracellular domain, wherein the extracellular antigen-binding domain is encoded by at least one sequence of SEQ ID NO 37 or 38, and at least one sequence of SEQ ID NO 39 or 40,
according to SEQ ID No. 31, 32, 33, 34, or 35, and/or
b) a nucleic acid molecule which is complementary to a nucleotide sequence in accordance with a);
c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%;
d) a nucleic acid molecule which, as a consequence of the genetic code, is degenerate to a nucleotide sequence according to a) through c); and/or
e) a nucleic acid molecule according to a nucleotide sequence of a) through d) which is modified by deletions, additions, substitutions, translocations, inversions and/or insertions and is functionally analogous/equivalent to a nucleotide sequence according to a) through d).

In preferred embodiments of the invention, the isolated nucleic acid molecule, preferably in the form of a vector, such as a viral vector or a transposon vector, preferably a sleeping beauty vector, is selected from the group consisting of:
a) a nucleic acid molecule comprising a nucleotide sequence
which encodes a chimeric antigen receptor (CAR) polypeptide according to any embodiment of the CAR described herein,
which encodes an extracellular antigen-binding domain, a transmembrane domain, and an intracellular domain, wherein the extracellular antigen-binding domain is encoded by at least one sequence of SEQ ID NO 37, 53 or 38, and at least one sequence of SEQ ID NO 39, 54 or 40,
according to SEQ ID No. 31, 32, 33, 34, or 35, and/or
b) a nucleic acid molecule which is complementary to a nucleotide sequence in accordance with a);
c) a nucleic acid molecule comprising a nucleotide sequence having sufficient sequence identity to be functionally analogous/equivalent to a nucleotide sequence according to a) or b), comprising a sequence identity to a nucleotide sequence according to a) or b) of at least 80%, preferably 90%, or 95% sequence identity to a nucleotide sequence according to a) or b), wherein functional analogy relates to binding CXCR5 target antigen, and when corresponding T cells express said construct, the CAR-T cell product confers T cells with a cytotoxic activity against mature B-NHLs, while sparing normal hematopoietic cells such as T cells (except for Tfh or other T cell lymphomas described herein), plasma B cells and their bone marrow precursors; and/or
d) a nucleic acid molecule which, as a consequence of the genetic code, is degenerate to a nucleotide sequence according to a) through c).

The term degenerate to (or degenerated into) refers to differences in nucleotide sequence of a nucleic acid molecule, but according to the genetic code, do not lead to differences in amino acid protein product of the nucleotide sequence after translation. In one embodiment, the nucleic acid molecule relates to the above molecules under a) and b), a), b) and c), or a), b) and d).

Preferred amino acid and nucleotide sequences of the present invention:

| SEQ ID No. | Sequence | Description |
|---|---|---|
| 1 | GFTFSTSG | H-CDR1 |
| 2 | ISSSSGFV | H-CDR2 |
| 3 | ARSEAAF | H-CDR3 |
| 4 | KSRLSRMGITP | L-CDR1 |
| 5 | RMS | L-CDR2 |

| SEQ ID No. | Sequence | Description |
|---|---|---|
| 6 | AQFLEYPPT | L-CDR3 |
| 7 | EVQLVESGGGLVQPGX1SLX2LSCX3ASGFTFSTSGMX4WFRQAPGK GLX5WVX6YISSSSGFVYADX7VKGRFTISRDNAQNX8LYLQX9NSLX1 0X11EDTAX12YYCARSEAAFWGQGTLVTVSS<br>wherein X1: G OR K, X2: R OR K; X3: A OR S;<br>X4: N OR H; X5: E OR D; X6: S OR A; X7: S OR A;<br>X8: S OR T; X9: M OR L; X10: R OR K, X11: A OR S;<br>X12: V OR I | VH sequence "generalized" encompassing both rat and humanized sequences |
| 7 | EVQLVESGGGLVQPGXSLXLSCXASGFTFSTSGMXWFRQAPGKGLX WVXYISSSSGFVYADXVKGRFTISRDNAQNXLYLQXNSLXXEDTAXYY CARSEAAFWGQGTLVTVSS<br>wherein X is any amino acid, preferably those above. | VH sequence "generalized" encompassing both rat and humanized sequences |
| 8 | DIVLTQX1PRSX2PVTPGEX3ASISCRSX4KSRLSRMGITPLNWYLQKP GX5SPQLLIYRMSNX6ASGVPDRFSGSGSX7TDFTLKISKVETEDVGVY YCAQFLEYPPTFGSGTKLEIK<br>wherein X1: S or A; X2: L or V; X3: P or S;<br>X4: S or N; X5: Q or K; X6: R or L; X7: G or E | VL sequence "generalized" encompassing both rat and humanized sequences |
| 8 | DIVLTQXPRSXPVTPGEXASISCRSXKSRLSRMGITPLNWYLQKPGXS PQLLIYRMSNXASGVPDRFSGSGSXTDFTLKISKVETEDVGVYYCAQF LEYPPTFGSGTKLEIK<br>wherein X is any amino acid, preferably those above. | VL sequence "generalized" encompassing both rat and humanized sequences |
| 9 | EVQLVESGGGLVQPGSLRLSCAASGFTFSTSGMNWFRQAPGKGLE WVSYISSSSGFVYADSVKGRFTISRDNAQNSLYLQMNSLRAEDTAVYY CARSEAAFWGQGTLVTVSS | Humanized VH |
| 10 | EVQLVESGGGLVQPGKSLKLSCSASGFTFSTSGMHWFRQAPGKGLD WVAYISSSSGFVYADAVKGRFTISRDNAQNTLYLQLNSLKSEDTAIYYC ARSEAAFWGQGTLVTVSS | Rat VH |
| 11 | DIVLTQSPRSLPVTPGEPASISCRSSKSRLSRMGITPLNWYLQKPGQS PQLLIYRMSNRASGVPDRFSGSGSGTDFTLKISKVETEDVGVYYCAQF LEYPPTFGSGTKLEIK | Humanized VL |
| 12 | DIVLTQAPRSVSVTPGESASISCRSNKSRLSRMGITPLNWYLQKPGKS PQLLIYRMSNLASGVPDRFSGSGSETDFTLKISKVETEDVGVYYCAQF LEYPPTFGSGTKLEIK | Rat VL |
| 13 | GSTSGSGKPGSGEGSTKG | Whitlow linker |
| 14 | SSGGGGSGGGGSGGGGS | Gly-Ser linker |
| 15 | PAEPKSPDKTHTCPPCPAPPVAGPSVFLFPPKPKDTLMIARTPEVTCV VVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPGKKDPK | IgG1 spacer |
| 16 | PAEPKSPDKTHTCPPCPAPPVAGPSVFLFPPKPKDTLMIARTPEVTCV VVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSSLSPGKK | IgG1Δ spacer |
| 17 | ESKYGPPCPPCPAPEFEGGPSVFLFPPKPKDTLMISRTPEVTCVVVDV SQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK | IgG4 (HI—CH2—CH3) spacer |
| 18 | ESKYGPPCPPCPGQPREPQVYTLPPSQEEMTKNQVSLTCLVKGFYPS DIAVEWESNGQPENNYKTTPPVLDSDGSFFLYSRLTVDKSRWQEGNV FSCSVMHEALHNHYTQKSLSLSLGK | IgG4 (HI—CH3) spacer |
| 19 | ESKYGPPCPPCP | IgG4 (HI) spacer |

| SEQ ID No. | Sequence | Description |
|---|---|---|
| 20 | IYIWAPLAGTCGVLLLSLVITLYC | transmembrane domain CD8α |
| 21 | FWVLVVVGGVLACYSLLVTVAFIIFWV | transmembrane domain CD28 |
| 22 | KRGRKKLLYIFKQPFMRPVQTTQEEDGCSCRFPEEEEGGCEL | Co-stimulatory domain 4-1BB |
| 23 | RSKRSRLLHSDYMNMTPRRPGPTRKHYQPYAPPRDFAAYRSL | Co-stimulatory domain CD28 |
| 24 | LRVKFSRSADAPAYQQGQNQLYNELNLGRREEYDVLDKRRGRDPEM<br>GGKPRRKNPQEGLYNELQKDKMAEAYSEIGMKGERRRGKGHDGLYQ<br>GLSTATKDTYDALHMQALPPR | Activation domain CD3 zeta (4-1BB) or (CD28) |
| 25 | MDFQVQIFSFLLISASVIMSREVQLVESGGGLVQPGGSLRLSCAASGF<br>TFSTSGMNWFRQAPGKGLEWVSYISSSSGFVYADSVKGRFTISRDNA<br>QNSLYLQMNSLRAEDTAVYYCARSEAAFWGQGTLVTVSSGSTSGSG<br>KPGSGEGSTKGDIVLTQSPRSLPVTPGEPASISCRSSKSRLSRMGITPL<br>NWYLQKPGQSPQLLIYRMSNRASGVPDRFSGSGSGTDFTLKISKVETE<br>DVGVYYCAQFLEYPPTFGSGTKLEIKPAEPKSPDKTHTCPPCPAPPVA<br>GPSVFLFPPKPKDTLMIARTPEVTCVVVDVSHEDPEVKFNWYVDGVEV<br>HNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVE<br>WESNGQPENNYKTTPPVLDSDGSFFLYSKLTVDKSRWQQGNVFSCS<br>VMHEALHNHYTQKSLSLSPGKKDPKFWVLVVVGGVLACYSLLVTVAFII<br>FWVRSKRSRLLHSDYMNMTPRRPGPTRKHYQPYAPPRDFAAYRSLR<br>VKFSRSADAPAYQQGQNQLYNELNLGRREEYDVLDKRRGRDPEMGG<br>KPRRKNPQEGLYNELQKDKMAEAYSEIGMKGERRRGKGHDGLYQGL<br>STATKDTYDALHMQALPPR | H28 MP71-hCXCR5-VH-Whitlow-VL-IgG1-CD28-CD28-CD3z |
| 26 | MDFQVQIFSFLLISASVIMSREVQLVESGGGLVQPGKSLKLSCSASGFT<br>FSTSGMHWFRQAPGKGLDWVAYISSSSGFVYADAVKGRFTISRDNAQ<br>NTLYLQLNSLKSEDTAIYYCARSEAAFWGQGTLVTVSSGSTSGSGKPG<br>SGEGSTKGDIVLTQAPRSVSVTPGESASISCRSNKSRLSRMGITPLNW<br>YLQKPGKSPQLLIYRMSNLASGVPDRFSGSGSETDFTLKISKVETEDV<br>GVYYCAQFLEYPPTFGSGTKLEIKPAEPKSPDKTHTCPPCPAPPVAGP<br>SVFLFPPKPKDTLMIARTPEVTCVVVDVSHEDPEVKFNWYVDGVEVHN<br>AKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVM<br>HEALHNHYTQKSLSLSPGKKDPKFWVLVVVGGVLACYSLLVTVAFIIFW<br>VRSKRSRLLHSDYMNMTPRRPGPTRKHYQPYAPPRDFAAYRSLRVKF<br>SRSADAPAYQQGQNQLYNELNLGRREEYDVLDKRRGRDPEMGGKPR<br>RKNPQEGLYNELQKDKMAEAYSEIGMKGERRRGKGHDGLYQGLSTA<br>TKDTYDALHMQALPPR | R28 MP71-ratCXCR5-VH-Whitlow-VL-IgG1-CD28-CD28-CD3z |
| 27 | MDFQVQIFSFLLISASVIMSREVQLVESGGGLVQPGGSLRLSCAASGF<br>TFSTSGMNWFRQAPGKGLEWVSYISSSSGFVYADSVKGRFTISRDNA<br>QNSLYLQMNSLRAEDTAVYYCARSEAAFWGQGTLVTVSSGSTSGSG<br>KPGSGEGSTKGDIVLTQSPRSLPVTPGEPASISCRSSKSRLSRMGITPL<br>NWYLQKPGQSPQLLIYRMSNRASGVPDRFSGSGSGTDFTLKISKVETE<br>DVGVYYCAQFLEYPPTFGSGTKLEIKPAEPKSPDKTHTCPPCPAPPVA<br>GPSVFLFPPKPKDTLMIARTPEVTCVVVDVSHEDPEVKFNWYVDGVEV<br>HNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVE<br>WESNGQPENNYKTTPPVLDSDGSFFLYSKLTVDKSRWQQGNVFSCS<br>VMHEALHNHYTQKSLSSLSPGKKIYIWAPLAGTCGVLLLSLVITLYCKR<br>GRKKLLYIFKQPFMRPVQTTQEEDGCSCRFPEEEEGGCELLRVKFSR<br>SADAPAYQQGQNQLYNELNLGRREEYDVLDKRRGRDPEMGGKPRRK<br>NPQEGLYNELQKDKMAEAYSEIGMKGERRRGKGHDGLYQGLSTATK<br>DTYDALHMQALPPR | HBB1 MP71-hCXCR5-VH-Whitlow-VL-IgG1Δ-CD8α-4-1BB-CD3z |
| 28 | MDFQVQIFSFLLISASVIMSREVQLVESGGGLVQPGGSLRLSCAASGF<br>TFSTSGMNWFRQAPGKGLEWVSYISSSSGFVYADSVKGRFTISRDNA<br>QNSLYLQMNSLRAEDTAVYYCARSEAAFWGQGTLVTVSSGSTSGSG<br>KPGSGEGSTKGDIVLTQSPRSLPVTPGEPASISCRSSKSRLSRMGITPL<br>NWYLQKPGQSPQLLIYRMSNRASGVPDRFSGSGSGTDFTLKISKVETE<br>DVGVYYCAQFLEYPPTFGSGTKLEIKPAEPKSPDKTHTCPPCPAPPVA<br>GPSVFLFPPKPKDTLMIARTPEVTCVVVDVSHEDPEVKFNWYVDGVEV<br>HNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVE<br>WESNGQPENNYKTTPPVLDSDGSFFLYSKLTVDKSRWQQGNVFSCS | HBB2 MP71-hCXCR5-VH-Whitlow-VL-IgG1-CD28-4-1BB-CD3z |

| SEQ ID No. | Sequence | Description |
|---|---|---|
| | VMHEALHNHYTQKSLSLSPGKKDPKFWVLVVVGGVLACYSLLVTVAFII<br>FWVKRGRKKLLYIFKQPFMRPVQTTQEEDGCSCRFPEEEEGGCELLR<br>VKFSRSADAPAYQQGQNQLYNELNLGRREEYDVLDKRRGRDPEMGG<br>KPRRKNPQEGLYNELQKDKMAEAYSEIGMKGERRRGKGHDGLYQGL<br>STATKDTYDALHMQALPPR | |
| 29 | MDFQVQIFSFLLISASVIMSREVQLVESGGGLVQPGGSLRLSCAASGF<br>TFSTSGMNWFRQAPGKGLEWVSYISSSSGFVYADSVKGRFTISRDNA<br>QNSLYLQMNSLRAEDTAVYYCARSEAAFWGQGTLVTVSSGSTSGSG<br>KPGSGEGSTKGDIVLTQSPRSLPVTPGEPASISCRSSKSRLSRMGITPL<br>NWYLQKPGQSPQLLIYRMSNRASGVPDRFSGSGSGTDFTLKISKVETE<br>DVGVYYCAQFLEYPPTFGSGTKLEIKPAEPKSPDKTHTCPPCPAPPVA<br>GPSVFLFPPKPKDTLMIARTPEVTCVVVDVSHEDPEVKFNWYVDGVEV<br>HNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVE<br>WESNGQPENNYKTTPPVLDSDGSFFLYSKLTVDKSRWQQGNVFSCS<br>VMHEALHNHYTQKSLSLSPGKKDPKFWVLVVVGGVLACYSLLVTVAFII<br>FWVRSKRSRLLHSDYMNMTPRRPGPTRKHYQPYAPPRDFAAYRSLK<br>RGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRK<br>NPQEGLYNELQKDKMAEAYSEIGMKGERRRGKGHDGLYQGLSTATK<br>DTYDALHMQALPPR | H28BB<br>MP71-<br>hCXCR5-VH-<br>Whitlow-VL-<br>IgG1-CD28-<br>CD28-4-1BB-<br>CD3z |
| 30 | MDFQVQIFSFLLISASVIMSR | Lkappa Leader |
| 31 | ATGGATTTCCAGGTGCAGATCTTCAGCTTCCTGCTGATCTCCGCCA<br>GCGTGATCATGAGCCGCGAGGTGCAGCTGGTGGAATCTGGCGGA<br>GGACTGGTGCAGCCTGGCGGCTCTCTGAGACTGTCTTGTGCCGCC<br>AGCGGCTTCACCTTCAGCACCAGCGGCATGAACTGGTTCAGACAG<br>GCCCCTGGCAAGGGCCTGGAATGGGTGTCCTACATCAGCAGCAGC<br>TCCGGCTTCGTGTACGCCGACAGCGTGAAGGGCCGGTTCACCATC<br>AGCAGAGACAACGCCCAGAACAGCCTGTACCTGCAGATGAACTCC<br>CTGCGGGCCGAGGACACCGCCGTGTACTACTGTGCCAGAAGCGAG<br>GCCGCCTTTTGGGGCCAGGGAACACTCGTGACAGTGTCCAGCGGC<br>AGCACAAGCGGCTCTGGCAAACCTGGATCTGGCGAGGGCAGCACC<br>AAGGGCGATATCGTGCTGACCCAGAGCCCCAGATCCCTGCCTGTG<br>ACACCTGGCGAGCCTGCCAGCATCAGCTGCAGAAGCAGCAAGAGC<br>CGGCTGAGCCGGATGGGCATCACCCCCCTGAACTGGTATCTGCAG<br>AAACCCGGCCAGTCCCCCCAGCTGCTGATCTACCGGATGAGCAAC<br>AGAGCCAGCGGCGTGCCCGATAGATTTTCCGGCTCTGGAAGCGGC<br>ACCGACTTCACCCTGAAGATCAGCAAGGTGGAAACCGAGGACGTG<br>GGCGTGTACTATTGCGCCCAGTTCCTGGAATACCCCCCCACCTTTG<br>GCAGCGGCACCAAGCTGGAAATCAAGCCCGCCGAGCCCAAGAGC<br>CCCGACAAGACCCATACCTGCCCTCCATGTCCTGCCCCTCCAGTG<br>GCTGGCCCTAGCGTGTTCCTGTTCCCCCCAAAGCCCAAGGACACC<br>CTGATGATCGCCCGGACCCCTGAAGTGACCTGCGTGGTGGTGGAT<br>GTGTCCCACGAGGATCCCGAAGTGAAGTTCAATTGGTACGTGGAC<br>GGCGTGGAAGTGCACAACGCCAAGACCAAGCCCAGAGAGGAACAG<br>TACAACAGCACCTACCGGGTGGTGTCTGTGCTGACCGTGCTGCAT<br>CAGGACTGGCTGAACGGCAAAGAGTACAAGTGCAAGGTGTCCAAC<br>AAGGCCCTGCCTGCCCCCATCGAGAAAACCATCTCCAAGGCCAAG<br>GGACAGCCCCGCGAGCCCCAGGTGTACACTGCCTCCAAGCAGG<br>GACGAGCTGACCAAGAACCAGGTCAGCCTGACCTGCCTGGTCAAA<br>GGCTTCTATCCCAGCGACATCGCCGTGGAGTGGGAGAGCAATGGG<br>CAGCCGGAGAACAACTACAAGACCACGCCTCCCGTGCTGGACTCC<br>GACGGCTCCTTCTTCCTCTACAGCAAGCTCACCGTGGACAAGAGCA<br>GGTGGCAGCAGGGGAACGTCTTCTCATGCTCCGTGATGCATGAGG<br>CTCTGCACAACCACTACACGCAGAAGAGCCTCTCCCTGTCTCCGG<br>GTAAAAAAGATCCCAAATTTTGGGTGCTGGTGGTGGTTGGTGGAGT<br>CCTGGCTTGCTATAGCTTGCTAGTAACAGTGGCTTTTATTATTTTCT<br>GGGTGAGGAGTAAGAGGAGCAGGCTCCTGCACAGTGACTACATGA<br>ACATGACTCCCCGCCGCCCCGGGCCCACCCGCAAGCATTACCAGC<br>CCTATGCCCCACCACGCGACTTCGCAGCCTATCGCTCCCTGAGAG<br>TGAAGTTCAGCAGGAGCGCAGACGCCCCCGCGTACCAGCAGGGC<br>CAGAACCAGCTCTATAACGAGCTCAATCTAGGACGAAGAGAGGAGT<br>ACGATGTTTTGGACAAGAGACGTGGCCGGGACCCTGAGATGGGGG<br>GAAAGCCGAGAAGGAAGAACCCTCAGGAAGGCCTGTACAATGAAC<br>TGCAGAAAGATAAGATGGCGGAGGCCTACAGTGAGATTGGGATGA<br>AAGGCGAGCGCCGGAGGGGCAAGGGGCACGATGGCCTTTACCAG<br>GGTCTCAGTACAGCCACCAAGGACACCTACGACGCCCTTCACATG<br>CAGGCCCTGCCCCCTCGCTGA | H28<br>MP71-<br>hCXCR5-VH-<br>Whitlow-VL-<br>IgG1-CD28-<br>CD28-CD3z |
| 32 | ATGGATTTCCAGGTGCAGATCTTCAGCTTCCTGCTGATCTCCGCCA<br>GCGTGATCATGAGCCGCGAGGTACAGCTGGTGGAGTCTGGAGGAG<br>GCTTAGTGCAGCCTGGAAAGTCCCTGAAACTCTCCTGTTCAGCCTC<br>TGGATTCACATTCAGTACCTCTGGCATGCACTGGTTTCGCCAAGCT | R28<br>MP71-<br>ratCXCR5-VH-<br>Whitlow-VL- |

| SEQ ID No. | Sequence | Description |
|---|---|---|
| | CCAGGAAAGGGGCTGGATTGGGTTGCATACATTAGTAGTAGCAGC<br>GGTTTCGTCTATGCAGACGCTGTGAAGGGCCGGTTCACCATCTCCA<br>GAGACAATGCACAGAACACCCTGTACCTGCAACTCAACAGTCTGAA<br>GTCTGAAGACACTGCCATCTATTACTGTGCAAGAAGCGAGGCTGCT<br>TTCTGGGGCCAAGGCACTCTGGTCACTGTCTCTTCAGGCAGCACCA<br>GCGGCTCCGGCAAGCCTGGCTCTGGCGAGGGCAGCACAAAGGGA<br>GATATTGTGTTGACTCAAGCTCCACGCTCTGTATCTGTCACTCCTG<br>GAGAGTCAGCTTCCATCTCCTGCAGGTCTAATAAGAGTCGACTGAG<br>TAGGATGGGCATCACTCCCTTGAATTGGTACCTTCAGAAGCCAGGA<br>AAGTCTCCTCAGCTCCTGATATATCGGATGTCCAACCTTGCCTCAG<br>GAGTTCCAGACAGGTTTAGTGGCAGTGGGTCAGAAACAGATTTTAC<br>ACTGAAAATCAGTAAGGTGGAGACTGAGGATGTTGGCGTTTATTAC<br>TGTGCACAGTTTCTAGAATATCCTCCTACGTTCGGTTCTGGGACCA<br>AGCTGGAGATCAAACCTGCCGAGCCTAAGAGCCCCGACAAGACCC<br>ACACCTGTCCCCCTTGTCCTGCCCCTCCAGTGGCTGGCCCTAGCG<br>TGTTCCTGTTCCCCCCAAAGCCCAAGGATACCCTGATGATCGCCCG<br>GACCCCCGAAGTCACATGCGTGGTGGTGGACGTGAGCCACGAAGA<br>CCCTGAGGTCAAGTTCAACTGGTACGTGGACGGCGTGGAGGTGCA<br>TAATGCCAAGACAAAGCCGCGGGAGGAGCAGTACAACAGCACGTA<br>CCGTGTGGTCAGCGTCCTCACCGTCCTGCACCAGGACTGGCTGAA<br>TGGCAAGGAGTACAAGTGCAAGGTCTCCAACAAAGCCCTCCCAGC<br>CCCCATCGAGAAAACCATCTCCAAAGCCAAAGGGCAGCCCCGAGA<br>ACCACAGGTGTACACCCTGCCCCCATCCGGGATGAGCTGACCAA<br>GAACCAGGTCAGCCTGACCTGCCTGGTCAAAGGCTTCTATCCCAG<br>CGACATCGCCGTGGAGTGGGAGAGCAATGGGCAGCCGGAGAACA<br>ACTACAAGACCACGCCTCCCGTGCTGGACTCCGACGGCTCCTTCTT<br>CCTCTACAGCAAGCTCACCGTGGACAAGAGCAGGTGGCAGCAGGG<br>GAACGTCTTCTCATGCTCCGTGATGCATGAGGCTCTGCACAACCAC<br>TACACGCAGAAGAGCCTCTCCCTGTCTCCGGGTAAAAAAGATCCCA<br>AATTTTGGGTGCTGGTGGTGGTTGGTGGAGTCCTGGCTTGCTATAG<br>CTTGCTAGTAACAGTGGCCTTTATTATTTTCTGGGTGAGGAGTAAGA<br>GGAGCAGGCTCCTGCACAGTGACTACATGAACATGACTCCCCGCC<br>GCCCCGGGCCCACCCGCAAGCATTACCAGCCCTATGCCCCACCAC<br>GCGACTTCGCAGCCTATCGCTCCCTGAGAGTGAAGTTCAGCAGGA<br>GCGCAGACGCCCCCGCGTACCAGCAGGGCCAGAACCAGCTCTATA<br>ACGAGCTCAATCTAGGACGAAGAGAGGAGTACGATGTTTTGGACAA<br>GAGACGTGGCCGGGACCCTGAGATGGGGGGAAAGCCGAGAAGGA<br>AGAACCCTCAGGAAGGCCTGTACAATGAACTGCAGAAAGATAAGAT<br>GGCGGAGGCCTACAGTGAGATTGGGATGAAAGGCGAGCGCCGGA<br>GGGGCAAGGGGCACGATGGCCTTTACCAGGGTCTCAGTACAGCCA<br>CCAAGGACACCTACGACGCCCTTCACATGCAGGCCCTGCCCCCTC<br>GCTGA | IgG1-CD28-<br>CD28-CD3z |
| 33 | ATGGATTTCCAGGTGCAGATCTTCAGCTTCCTGCTGATCTCCGCCA<br>GCGTGATCATGAGCCGCGAGGTGCAGCTGGTGGAATCTGGCGGA<br>GGACTGGTGCAGCCTGGCGGCTCTCTGAGACTGTCTTGTGCCGCC<br>AGCGGCTTCACCTTCAGCACCAGCGGCATGAACTGGTTCAGACAG<br>GCCCCTGGCAAGGGCCTGGAATGGGTGTCCTACATCAGCAGCAG<br>TCCGGCTTCGTGTACGCCGACAGCGTGAAGGGCCGGTTCACCATC<br>AGCAGAGACAACGCCCAGAACAGCCTGTACCTGCAGATGAACTCC<br>CTGCGGGCCGAGGACACCGCCGTGTACTACTGTGCCAGAAGCGAG<br>GCCGCCTTTTGGGGCCAGGGAACACTCGTGACAGTGTCCAGCGGC<br>AGCACAAGCGGCTCTGGCAAACCTGGATCTGGCGAGGGCAGCACC<br>AAGGGCGATATCGTGCTGACCCAGAGCCCCAGATCCCTGCCTGTG<br>ACACCTGGCGAGCCTGCCAGCATCAGCTGCAGAAGCAGCAAGAGC<br>CGGCTGAGCCGGATGGGCATCACCCCCCTGAACTGGTATCTGCAG<br>AAACCCGGCCAGTCCCCCAGCTGCTGATCTACCGGATGAGCAAC<br>AGAGCCAGCGGCGTGCCCGATAGATTTTCCGGCTCTGGAAGCGGC<br>ACCGACTTCACCCTGAAGATCAGCAAGGTGGAAACCGAGGACGTG<br>GGCGTGTACTATTGCGCCCAGTTCCTGGAATACCCCCCCACCTTTG<br>GCAGCGGCACCAAGCTGGAAATCAAGCCCGCCGAGCCCAAGAGC<br>CCCGACAAGACCCATACCTGCCCTCCATGTCCTGCCCCTCCAGTG<br>GCTGGCCCTAGCGTGTTCCTGTTCCCCCCAAAGCCCAAGGACACC<br>CTGATGATCGCCCGGACCCCTGAAGTGACCTGCGTGGTGGTGGAT<br>GTGTCCCACGAGGATCCCGAAGTGAAGTTCAATTGGTACGTGGAC<br>GGCGTGGAAGTGCACAACGCCAAGACCAAGCCCAGAGAGGAACAG<br>TACAACAGCACCTACCGGGTGGTGTCTGTGCTGACCGTGCTGCAT<br>CAGGACTGGCTGAACGGCAAAGAGTACAAGTGCAAGGTGTCCAAC<br>AAGGCCCTGCCTGCCCCCATCGAGAAAACCATCTCCAAGGCCAAG<br>GGACAGCCCCGCGAGCCCCAGGTGTACACACTGCCTCCAAGCAGG<br>GACGAGCTGACCAAGAACCAGGTGTCCCTGACCTGCCTCGTGAAG<br>GGCTTCTACCCCTCCGATATCGCCGTGGAATGGGAGAGCAATGGC<br>CAGCCCGAGAACAACTACAAGACCACCCCCCTGTGCTGGACAGC<br>GACGGCTCATTCTTCCTGTACAGCAAGCTGACAGTGGACAAGAGCC<br>GGTGGCAGCAGGGCAACGTGTTCAGCTGCAGCGTGATGCACGAG<br>GCTCTGCACAACCACTACACCCAGAAGTCCCTGAGCAGCCTGAGC | HBB1<br>MP71-<br>hCXCR5-VH-<br>Whitlow-VL-<br>IgG1Δ-CD8α-<br>4-1BB-CD3z |

| SEQ ID No. | Sequence | Description |
|---|---|---|
| | CCAGGCAAGAAGATCTACATCTGGGCCCCTCTGGCCGGCACCTGT<br>GGCGTGCTGCTGCTGTCTCTCGTGATCACACTGTACTGCAAGCGG<br>GGCAGAAAGAAGCTGCTGTACATCTTCAAGCAGCCCTTCATGCGGC<br>CCGTGCAGACCACCCAGGAAGAGGACGGCTGCTCCTGCAGATTCC<br>CCGAGGAAGAAGAAGGCGGCTGCGAGCTGCTGCGCGTGAAGTTTT<br>CTAGAAGCGCCGACGCCCCTGCCTACCAGCAGGGCCAGAACCAGC<br>TGTACAACGAGCTGAACCTGGGCAGACGGGAAGAGTACGACGTGC<br>TGGATAAGCGGAGAGGCCGGGACCCTGAGATGGGCGGCAAGCCT<br>AGAAGAAAGAACCCCCAGGAAGGCCTGTATAACGAACTGCAGAAA<br>GACAAGATGGCCGAGGCCTACAGCGAGATCGGAATGAAGGGCGA<br>GCGGAGAAGAGGCAAGGGCCACGATGGACTGTACCAGGGCCTGA<br>GCACCGCCACCAAGGACACCTATGACGCCCTGCACATGCAGGCTC<br>TGCCCCCCAGATAA | |
| 34 | ATGGATTTCCAGGTGCAGATCTTCAGCTTCCTGCTGATCTCCGCCA<br>GCGTGATCATGAGCCGCGAGGTGCAGCTGGTGGAATCTGGCGGA<br>GGACTGGTGCAGCCTGGCGGCTCTCTGAGACTGTCTTGTGCCGCC<br>AGCGGCTTCACCTTCAGCACCAGCGGCATGAACTGGTTCAGACAG<br>GCCCCTGGCAAGGGCCTGGAATGGGTGTCCTACATCAGCAGCAGC<br>TCCGGCTTCGTGTACGCCGACAGCGTGAAGGGCCGGTTCACCATC<br>AGCAGAGACAACGCCCAGAACAGCCTGTACCTGCAGATGAACTCC<br>CTGCGGGCCGAGGACACCGCCGTGTACTACTGTGCCAGAAGCGAG<br>GCCGCCTTTTGGGGCCAGGGAACACTCGTGACAGTGTCCAGCGGC<br>AGCACAAGCGGCTCTGGCAAACCTGGATCTGGCGAGGGCAGCACC<br>AAGGGCGATATCGTGCTGACCCAGAGCCCCAGATCCCTGCCTGTG<br>ACACCTGGCGAGCCTGCCAGCATCAGCTGCAGAAGCAGCAAGAGC<br>CGGCTGAGCCGGATGGGCATCACCCCCCTGAACTGGTATCTGCAG<br>AAACCCGGCCAGTCCCCCCAGCTGCTGATCTACCGGATGAGCAAC<br>AGAGCCAGCGGCGTGCCCGATAGATTTTCCGGCTCTGGAAGCGGC<br>ACCGACTTCACCCTGAAGATCAGCAAGGTGGAAACCGAGGACGTG<br>GGCGTGTACTATTGCGCCCAGTTCCTGGAATACCCCCCCACCTTTG<br>GCAGCGGCACCAAGCTGGAAATCAAGCCCGCCGAGCCCAAGAGC<br>CCCGACAAGACCCATACCTGCCCTCCATGTCCTGCCCCTCCAGTG<br>GCTGGCCCTAGCGTGTTCCTGTTCCCCCCAAAGCCCAAGGACACC<br>CTGATGATCGCCCGGACCCCTGAAGTGACCTGCGTGGTGGTGGAT<br>GTGTCCCACGAGGATCCCGAAGTGAAGTTCAATTGGTACGTGGAC<br>GGCGTGGAAGTGCACAACGCCAAGACCAAGCCCAGAGAGGAACAG<br>TACAACAGCACCTACCGGGTGGTGTCTGTGCTGACCGTGCTGCAT<br>CAGGACTGGCTGAACGGCAAAGAGTACAAGTGCAAGGTGTCCAAC<br>AAGGCCCTGCCTGCCCCCATCGAGAAAACCATCTCCAAGGCCAAG<br>GGACAGCCCCGCGAGCCCCAGGTGTACACACTGCCTCCAAGCAGG<br>GACGAGCTGACCAAGAACCAGGTCAGCCTGACCTGCCTGGTCAAA<br>GGCTTCTATCCCAGCGACATCGCCGTGGAGTGGGAGAGCAATGGG<br>CAGCCGGAGAACAACTACAAGACCACGCCTCCCGTGCTGGACTCC<br>GACGGCTCCTTCTTCCTCTACAGCAAGCTCACCGTGGACAAGAGCA<br>GGTGGCAGCAGGGGAACGTCTTCTCATGCTCCGTGATGCATGAGG<br>CTCTGCACAACCACTACACGCAGAAGAGCCTCTCCCTGTCTCCGG<br>GTAAAAAAGATCCCAAATTTTGGGTGCTGGTGGTGGTTGGTGGAGT<br>CCTGGCTTGCTATAGCTTGCTAGTAACAGTGGCCTTTATTATTTTCT<br>GGGTGAAGCGGGGCAGAAAGAAGCTGCTGTACATCTTCAAGCAGC<br>CCTTCATGCGGCCCGTGCAGACCACCCAGGAAGAGGACGGCTGCT<br>CCTGCAGATTCCCCGAGGAAGAAGAAGGCGGCTGCGAGCTGCTGA<br>GAGTGAAGTTCAGCAGGAGCGCAGAGCCCCCGCGTACCAGCAG<br>GGCCAGAACCAGCTCTATAACGAGCTCAATCTAGGACGAAGAGAG<br>GAGTACGATGTTTTGGACAAGAGACGTGGCCGGGACCCTGAGATG<br>GGGGGAAAGCCGAGAAGGAAGAACCCTCAGGAAGGCCTGTACAAT<br>GAACTGCAGAAAGATAAGATGGCGGAGGCCTACAGTGAGATTGGG<br>ATGAAAGGCGAGCGCCGGAGGGGCAAGGGGCACGATGGCCTTTA<br>CCAGGGTCTCAGTACAGCCACCAAGGACACCTACGACGCCCTTCA<br>CATGCAGGCCCTGCCCCCTCGCTGA | HBB2<br>MP71-<br>hCXCR5-VH-<br>Whitlow-VL-<br>IgG1-CD28-4-<br>1BB-CD3z |
| 35 | ATGGATTTCCAGGTGCAGATCTTCAGCTTCCTGCTGATCTCCGCCA<br>GCGTGATCATGAGCCGCGAGGTGCAGCTGGTGGAATCTGGCGGA<br>GGACTGGTGCAGCCTGGCGGCTCTCTGAGACTGTCTTGTGCCGCC<br>AGCGGCTTCACCTTCAGCACCAGCGGCATGAACTGGTTCAGACAG<br>GCCCCTGGCAAGGGCCTGGAATGGGTGTCCTACATCAGCAGCAGC<br>TCCGGCTTCGTGTACGCCGACAGCGTGAAGGGCCGGTTCACCATC<br>AGCAGAGACAACGCCCAGAACAGCCTGTACCTGCAGATGAACTCC<br>CTGCGGGCCGAGGACACCGCCGTGTACTACTGTGCCAGAAGCGAG<br>GCCGCCTTTTGGGGCCAGGGAACACTCGTGACAGTGTCCAGCGGC<br>AGCACAAGCGGCTCTGGCAAACCTGGATCTGGCGAGGGCAGCACC<br>AAGGGCGATATCGTGCTGACCCAGAGCCCCAGATCCCTGCCTGTG<br>ACACCTGGCGAGCCTGCCAGCATCAGCTGCAGAAGCAGCAAGAGC<br>CGGCTGAGCCGGATGGGCATCACCCCCCTGAACTGGTATCTGCAG<br>AAACCCGGCCAGTCCCCCCAGCTGCTGATCTACCGGATGAGCAAC<br>AGAGCCAGCGGCGTGCCCGATAGATTTTCCGGCTCTGGAAGCGGC | H28BB<br>MP71-<br>hCXCR5-VH-<br>Whitlow-VL-<br>IgG1-CD28-<br>CD28-4-1BB-<br>CD3z |

| SEQ ID No. | Sequence | Description |
|---|---|---|
| | ACCGACTTCACCCTGAAGATCAGCAAGGTGGAAACCGAGGACGTG<br>GGCGTGTACTATTGCGCCCAGTTCCTGGAATACCCCCCCACCTTTG<br>GCAGCGGCACCAAGCTGGAAATCAAGCCCGCCGAGCCCAAGAGC<br>CCCGACAAGACCCATACCTGCCCTCCATGTCCTGCCCCTCCAGTG<br>GCTGGCCCAGCGTGTTCCTGTTCCCCCCAAAGCCCAAGGACACC<br>CTGATGATCGCCCGGACCCCTGAAGTGACCTGCGTGGTGGTGGAT<br>GTGTCCCACGAGGATCCCGAAGTGAAGTTCAATTGGTACGTGGAC<br>GGCGTGGAAGTGCACAACGCCAAGACCAAGCCCAGAGAGGAACAG<br>TACAACAGCACCTACCGGGTGGTGTCTGTGCTGACCGTGCTGCAT<br>CAGGACTGGCTGAACGGCAAAGAGTACAAGTGCAAGGTGTCCAAC<br>AAGGCCCTGCCTGCCCCCATCGAGAAAACCATCTCCAAGGCCAAG<br>GGACAGCCCCGCGAGCCCCAGGTGTACACTGCCTCCAAGCAGG<br>GACGAGCTGACCAAGAACCAGGTCAGCCTGACCTGCCTGGTCAAA<br>GGCTTCTATCCCAGCGACATCGCCGTGGAGTGGGAGAGCAATGGG<br>CAGCCGGAGAACAACTACAAGACCACGCCTCCCGTGCTGGACTCC<br>GACGGCTCCTTCTTCCTCTACAGCAAGCTCACCGTGGACAAGAGCA<br>GGTGGCAGCAGGGGAACGTCTTCTCATGCTCCGTGATGCATGAGG<br>CTCTGCACAACCACTACACGCAGAAGAGCCTCTCCCTGTCTCCGG<br>GTAAAAAAGATCCCAAATTTTGGGTGCTGGTGGTGGTTGGTGGAGT<br>CCTGGCTTGCTATAGCTTGCTAGTAACAGTGGCCTTTATTATTTTCT<br>GGGTGAGGAGTAAGAGGAGCAGGCTCCTGCACAGTGACTACATGA<br>ACATGACTCCCCGCCGCCCCGGGCCCACCCGCAAGCATTACCAGC<br>CCTATGCCCCACCACGCGACTTCGCAGCCTATCGCTCCCTGAAGC<br>GGGGCAGAAAGAAGCTGCTGTACATCTTCAAGCAGCCCTTCATGC<br>GGCCCGTGCAGACCACCCAGGAAGAGGACGGCTGCTCCTGCAGAT<br>TCCCCGAGGAAGAAGAAGGCGGCTGCGAGCTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGTTT<br>TGGACAAGAGACGTGGCCGGGACCCTGAGATGGGGGGAAAGCCG<br>AGAAGGAAGAACCCTCAGGAAGGCCTGTACAATGAACTGCAGAAA<br>GATAAGATGGCGGAGGCCTACAGTGAGATTGGGATGAAAGGCGAG<br>CGCCGGAGGGGCAAGGGGCACGATGGCCTTTACCAGGGTCTCAG<br>TACAGCCACCAAGGACACCTACGACGCCCTTCACATGCAGGCCCT<br>GCCCCCTCGCTGA | |
| 36 | ATGGATTTCCAGGTGCAGATCTTCAGCTTCCTGCTGATCTCCGCCA<br>GCGTGATCATGAGCCGC | Lkappa Leader |
| 37 | GAGGTGCAGCTGGTGGAATCTGGCGGAGGACTGGTGCAGCCTGG<br>CGGGCTCTCTGAGACTGTCTTGTGCCGCCAGCGGCTTCACCTTCAG<br>CACCAGCGGCATGAACTGGTTCAGACAGGCCCCTGGCAAGGGCCT<br>GGAATGGGTGTCCTACATCAGCAGCAGCTCCGGCTTCGTGTACGC<br>CGACAGCGTGAAGGGCCGGTTCACCATCAGCAGAGACAACGCCCA<br>GAACAGCCTGTACCTGCAGATGAACTCCCTGCGGGCCGAGGACAC<br>CGCCGTGTACTACTGTGCCAGAAGCGAGGCCGCCTTTTGGGGCCA<br>GGGAACACTCGTGACAGTGTCCAGC | Humanized VH Codon-optimized |
| 53 | GAGGTGCAGCTGGTGGAGAGCGGCGGCGGCCTGGTGCAGCCCGG<br>CGGCAGCCTGAGGCTGAGCTGCGCCGCCAGCGGCTTCACCTTCAG<br>CACCAGCGGCATGAACTGGTTCAGGCAGGCCCCCGGCAAGGGCC<br>TGGAGTGGGTGAGCTACATCAGCAGCAGCAGCGGCTTCGTGTACG<br>CCGACAGCGTGAAGGGCAGGTTCACCATCAGCAGGGACAACGCCC<br>AGAACAGCCTGTACCTGCAGATGAACAGCCTGAGGGCCGAGGACA<br>CCGCCGTGTACTACTGCGCCAGGAGCGAGGCCGCCTTCTGGGGC<br>CAGGGCACCCTGGTGACCGTG | Humanized VH Non-codon-optimzed |
| 38 | GAGGTACAGCTGGTGGAGTCTGGAGGAGGCTTAGTGCAGCCTGGA<br>AAGTCCCTGAAACTCTCCTGTTCAGCCTCTGGATTCACATTCAGTAC<br>CTCTGGCATGCACTGGTTTCGCCAAGCTCCAGGAAAGGGGCTGGA<br>TTGGGTTGCATACATTAGTAGTAGCAGCGGTTTCGTCTATGCAGAC<br>GCTGTGAAGGGCCGGTTCACCATCTCCAGAGACAATGCACAGAAC<br>ACCCTGTACCTGCAACTCAACAGTCTGAAGTCTGAAGACACTGCCA<br>TCTATTACTGTGCAAGAAGCGAGGCTGCTTTCTGGGGCCAAGGCAC<br>TCTGGTCACTGTCTCTTCA | Rat VH |
| 39 | GATATCGTGCTGACCCAGAGCCCCAGATCCCTGCCTGTGACACCT<br>GGCGAGCCTGCCAGCATCAGCTGCAGAAGCAGCAAGAGCCGGCT<br>GAGCCGGATGGGCATCACCCCCCTGAACTGGTATCTGCAGAAACC<br>CGGCCAGTCCCCCAGCTGCTGATCTACCGGATGAGCAACAGAGC<br>CAGCGGCGTGCCCGATAGATTTTCCGGCTCTGGAAGCGGCACCGA<br>CTTCACCCTGAAGATCAGCAAGGTGGAAACCGAGGACGTGGGCGT<br>GTACTATTGCGCCCAGTTCCTGGAATACCCCCCCACCTTTGGCAGC<br>GGCACCAAGCTGGAAATCAAG | Humanized VL |

| SEQ ID No. | Sequence | Description |
|---|---|---|
| 54 | GACATCGTGCTGACCCAGAGCCCCCGCAGCCTGCCCGTGACCCCC GGCGAGCCCGCCAGCATCAGCTGCAGGTCCTCCAAGTCCAGGCTG AGCAGGATGGGCATCACCCCCCTGAACTGGTACCTGCAGAAGCCC GGCCAGAGCCCCAGCTGCTGATCTACAGGATGAGCAACAGGGCC AGCGGCGTGCCCGACAGGTTCAGCGGCAGCGGCAGCGGCACCGA CTTCACCCTGAAGATCAGCAAGGTGGAGACCGAGGACGTGGGCGT GTACTACTGCGCCCAGTTCCTGGAGTACCCCCCCACCTTCGGCAG CGGCACCAAGCTGGAGATCAAG | Humanized VL Non-codon-optimzed |
| 40 | GATATTGTGTTGACTCAAGCTCCACGCTCTGTATCTGTCACTCCTG GAGAGTCAGCTTCCATCTCCTGCAGGTCTAATAAGAGTCGACTGAG TAGGATGGGCATCACTCCCTTGAATTGGTACCTTCAGAAGCCAGGA AAGTCTCCTCAGCTCCTGATATATCGGATGTCCAACCTTGCCTCAG GAGTTCCAGACAGGTTTAGTGGCAGTGGGTCAGAAACAGATTTTAC ACTGAAAATCAGTAAGGTGGAGACTGAGGATGTTGGCGTTTATTAC TGTGCACAGTTTCTAGAATATCCTCCTACGTTCGGTTCTGGGACCA AGCTGGAGATCAAA | Rat VL |
| 41 | GGCAGCACAAGCGGCTCTGGCAAACCTGGATCTGGCGAGGGCAG CACCAAGGGC | Humanized Whitlow |
| 42 | GGCAGCACCAGCGGCTCCGGCAAGCCTGGCTCTGGCGAGGGCAG CACAAAGGGA | Rat Whitlow |
| 43 | CCCGCCGAGCCCAAGAGCCCCGACAAGACCCATACCTGCCCTCCA TGTCCTGCCCCTCCAGTGGCTGGCCCTAGCGTGTTCCTGTTCCCC CCAAAGCCCAAGGACACCCTGATGATCGCCCGGACCCCCTGAAGTG ACCTGCGTGGTGGTGGATGTGTCCCACGAGGATCCCGAAGTGAAG TTCAATTGGTACGTGGACGGCGTGGAAGTGCACAACGCCAAGACC AAGCCCAGAGAGGAACAGTACAACAGCACCTACCGGGTGGTGTCT GTGCTGACCGTGCTGCATCAGGACTGGCTGAACGGCAAAGAGTAC AAGTGCAAGGTGTCCAACAAGGGCCCTGCCTGCCCCCATCGAGAAA ACCATCTCCAAGGCCAAGGGACAGCCCCGCGAGCCCCAGGTGTAC ACACTGCCTCCAAGCAGGGACGAGCTGACCAAGAACCAGGTCAGC CTGACCTGCCTGGTCAAAGGCTTCTATCCCAGCGACATCGCCGTG GAGTGGGAGAGCAATGGGCAGCCGGAGAACAACTACAAGACCACG CCTCCCGTGCTGGACTCCGACGGCTCCTTCTTCCTCTACAGCAAGC TCACCGTGGACAAGAGCAGGTGGCAGCAGGGGAACGTCTTCTCAT GCTCCGTGATGCATGAGGCTCTGCACAACCACTACACGCAGAAGA GCCTCTCCCTGTCTCCGGGTAAAAAAGATCCCAAA | Humanized IgG1 spacer |
| 44 | CCTGCCGAGCCTAAGAGCCCCGACAAGACCCACACCTGTCCCCCT TGTCCTGCCCCTCCAGTGGCTGGCCCTAGCGTGTTCCTGTTCCCC CCAAAGCCCAAGGATACCCTGATGATCGCCCGGACCCCCGAAGTC ACATGCGTGGTGGTGGACGTGAGCCACGAAGACCCTGAGGTCAAG TTCAACTGGTACGTGGACGGCGTGGAGGTGCATAATGCCAAGACA AAGCCGCGGGAGGAGCAGTACAACAGCACGTACCGTGTGGTCAGC GTCCTCACCGTCCTGCACCAGGACTGGCTGAATGGCAAGGAGTAC AAGTGCAAGGTCTCCAACAAAGCCCTCCCAGCCCCCATCGAGAAAA CCATCTCCAAAGCCAAAGGGCAGCCCCGAGAACCACAGGTGTACA CCCTGCCCCCATCCCGGGATGAGCTGACCAAGAACCAGGTCAGCC TGACCTGCCTGGTCAAAGGCTTCTATCCCAGCGACATCGCCGTGG AGTGGGAGAGCAATGGGCAGCCGGAGAACAACTACAAGACCACGC CTCCCGTGCTGGACTCCGACGGCTCCTTCTTCCTCTACAGCAAGCT CACCGTGGACAAGAGCAGGTGGCAGCAGGGGAACGTCTTCTCATG CTCCGTGATGCATGAGGCTCTGCACAACCACTACACGCAGAAGAG CCTCTCCCTGTCTCCGGGTAAAAAAGATCCCAAA | Rat IgG1 spacer |
| 45 | CCAGGTGTCCCTGACCTGCCTCGTGAAGGGCTTCTACCCCTCCGA TATCGCCGTGGAATGGGAGAGCAATGGCCAGCCCGAGAACAACTA CAAGACCACCCCCCCTGTGCTGGACAGCGACGGCTCATTCTTCCT GTACAGCAAGCTGACAGTGGACAAGAGCCGGTGGCAGCAGGGCAA CGTGTTCAGCTGCAGCGTGATGCACGAGGCTCTGCACAACCACTA CACCCAGAAGTCCCTGAGCAGCCTGAGCCCAGGCAAGAAG | Humanized IgG1Δ spacer |
| 46 | CCTGCCGAGCCTAAGAGCCCCGACAAGACCCACACCTGTCCCCCT TGTCCTGCCCCTCCAGTGGCTGGCCCTAGCGTGTTCCTGTTCCCC CCAAAGCCCAAGGATACCCTGATGATCGCCCGGACCCCCGAAGTC ACATGCGTGGTGGTGGACGTGAGCCACGAAGACCCTGAGGTCAAG TTCAACTGGTACGTGGACGGCGTGGAGGTGCATAATGCCAAGACA AAGCCGCGGGAGGAGCAGTACAACAGCACGTACCGTGTGGTCAGC GTCCTCACCGTCCTGCACCAGGACTGGCTGAATGGCAAGGAGTAC AAGTGCAAGGTCTCCAACAAAGCCCTCCCAGCCCCCATCGAGAAAA CCATCTCCAAAGCCAAAGGGCAGCCCCGAGAACCACAGGTGTACA CCCTGCCCCCATCCCGGGATGAGCTGACCAAGAA | Rat IgG1Δ spacer |

-continued

| SEQ ID No. | Sequence | Description |
|---|---|---|
| 47 | ATCTACATCTGGGCCCCTCTGGCCGGCACCTGTGGCGTGCTGCTG<br>CTGTCTCTCGTGATCACACTGTACTGC | transmembrane domainCD8α |
| 48 | TTTTGGGTGCTGGTGGTGGTTGGTGGAGTCCTGGCTTGCTATAGCT<br>TGCTAGTAACAGTGGCCTTTATTATTTTCTGGGTG | transmembrane domainCD28 |
| 49 | AAGCGGGGCAGAAAGAAGCTGCTGTACATCTTCAAGCAGCCCTTCA<br>TGCGGCCCGTGCAGACCACCCAGGAAGAGGACGGCTGCTCCTGC<br>AGATTCCCCGAGGAAGAAGAAGGCGGCTGCGAGCTG | Co-stimulatory domain4-1BB |
| 50 | AGGAGTAAGAGGAGCAGGCTCCTGCACAGTGACTACATGAACATG<br>ACTCCCCGCCGCCCCGGGCCCACCCGCAAGCATTACCAGCCCTAT<br>GCCCCACCACGCGACTTCGCAGCCTATCGCTCCCTG | Co-stimulatory domainCD28 |
| 51 | CTGCGCGTGAAGTTTTCTAGAAGCGCCGACGCCCCTGCCTACCAG<br>CAGGGCCAGAACCAGCTGTACAACGAGCTGAACCTGGGCAGACGG<br>GAAGAGTACGACGTGCTGGATAAGCGGAGAGGCCGGGACCCTGA<br>GATGGGCGGCAAGCCTAGAAGAAAGAACCCCCAGGAAGGCCTGTA<br>TAACGAACTGCAGAAAGACAAGATGGCCGAGGCCTACAGCGAGAT<br>CGGAATGAAGGGCGAGCGGAGAAGAGGCAAGGGCCACGATGGAC<br>TGTACCAGGGCCTGAGCACCGCCACCAAGGACACCTATGACGCCC<br>TGCACATGCAGGCTCTGCCCCCCAGATAA | Activation domainCD3 zeta (4-1BB) |
| 52 | AGAGTGAAGTTCAGCAGGAGCGCAGACGCCCCCGCGTACCAGCAG<br>GGCCAGAACCAGCTCTATAACGAGCTCAATCTAGGACGAAGAGAG<br>GAGTACGATGTTTTGGACAAGAGACGTGGCCGGGACCCTGAGATG<br>GGGGGAAAGCCGAGAAGGAAGAACCCTCAGGAAGGCCTGTACAAT<br>GAACTGCAGAAAGATAAGATGGCGGAGGCCTACAGTGAGATTGGG<br>ATGAAAGGCGAGCGCCGGAGGGGCAAGGGGCACGATGGCCTTTA<br>CCAGGGTCTCAGTACAGCCACCAAGGACACCTACGACGCCCTTCA<br>CATGCAGGCCCTGCCCCCTCGCTGA | Activation domainCD3 zeta (CD28) |

A further aspect of the invention relates to a vector comprising a nucleic acid molecule as described herein, preferably a viral vector, more preferably a gamma retroviral vector. In another aspect of the invention, the invention relates to a transposon vector, preferably a sleeping beauty vector, encoding and preferably capable of expressing the inventive CAR.

A further aspect of the invention relates to a genetically modified immune cell comprising a nucleic acid molecule or vector as described herein, and/or expressing a CAR as described herein.

In a preferred embodiment the immune cells intended for administering in treatment of the diseases mentioned herein are genetically modified with a nucleic acid as described herein, encoding and expressing the anti-CXCR5 CAR as described herein, using a "Sleeping beauty" transposon system, in particular a sleeping beauty transposase. The Sleeping Beauty transposon system is a synthetic DNA transposon designed to introduce precisely defined DNA sequences into the chromosomes of vertebrate animals, in the context of the present invention for the purposes of modifying immune cells to express the CAR as described herein. The sleeping beauty transposons combine the advantages of viruses and naked DNA. Viruses have been evolutionarily selected based on their abilities to infect and replicate in new host cells. Simultaneously, cells have evolved major molecular defense mechanisms to protect themselves against viral infections. Avoiding the use of viruses is also important for social and regulatory reasons. The use of non-viral vectors such as the sleeping beauty system therefore avoids many, but not all, of the defenses that cells employ against vectors. For this reason, the sleeping beauty system enables particularly effective and safe genetic modification of the immune cells for administration to a patient.

In further embodiments of the invention, CrispR/Cas and TALEN-mediated insertion of the CXCR5 CAR encoding nucleic acid may be employed. CrispR/Cas, known to a skilled person, which is adapted from a naturally occurring process in bacteria, may be employed to precisely and efficiently edit DNA to insert the appropriate coding sequences into the immune cell, preferably T cell, of interest. Cas9, a protein that acts as a molecular pair of scissors, is guided to a specific DNA sequence by an associated RNA molecule (a guide RNA). When Cas9 arrives at its target location on the DNA, it facilitates a change in the local genetic code, affecting the function of that gene. CRISPR/Cas9 can deliver the CAR gene to a very specific site within the T cell genome, which may reduce the risk of gene insertion at incorrect or undesired locations.

In one embodiment the immune cell is preferably selected from the group consisting of a T lymphocyte or an NK cell, more preferably cytotoxic T lymphocytes.

In a preferred embodiment the genetically modified immune cell comprising a nucleic acid molecule or vector as described herein, and/or expressing a CAR as described herein, is characterised in that it is CD4+ and/or CD8+ T cell, preferably a mixture of CD4+ and CD8+ T cells. These T cell populations, and preferably the composition comprising both CD4+ and CD8+ transformed cells, show particularly effective cytolytic activity against various malignant B cells, such as B-NHL, preferably against those cells and/or the associated medical conditions described herein.

In a preferred embodiment the genetically modified immune cells comprising a nucleic acid molecule or vector as described herein, and/or expressing a CAR as described herein, are CD4+ and CD8+ T cells, preferably in a ration of 1:10 to 10:1, more preferably in a ratio of 5:1 to 1:5, 2:1 to 1:2 or 1:1. Administration of CXCR5-directed modified CAR-T cells expressing the CAR described herein at the ratios mentioned, preferably at a 1:1 CD4+/CD8+ ratio, lead to beneficial characteristics during treatment of the diseases mentioned herein, for example these ratios lead to improved therapeutic response and reduced toxicity.

An additional and surprising aspect of the invention is an improved stability of the CAR as disclosed herein. The CAR polypeptide can readily be stored for extended periods under appropriate conditions without any loss of binding affinity.

A further aspect of the invention relates to a genetically modified immune cell as described herein for use in the treatment of a medical disorder associated with the presence of pathogenic cells expressing CXCR5.

In one embodiment the medical disorder to be treated is associated with the presence of pathogenic mature B cells and/or memory B cells.

In one embodiment the medical disorder to be treated is mature B cell non-Hodgkin's lymphoma (B-NHL).

In other embodiments the medical disorder to be treated is a B cell derived lymphoproliferative disorder, selected preferably from the group consisting of acute lymphoblastic leukemia (B-ALL), chronic lymphocytic leukemia (CLL), follicular lymphoma (FL), mantle cell lymphoma (MCL) and diffuse large B cell lymphoma (DLBCL).

In one embodiment the medical disorder to be treated is associated with the presence of pathogenic T cells and/or T follicular helper cells.

In one embodiment the medical disorder to be treated is a T cell non-Hodgkin's lymphoma, with or without a leukemic tumor cell dissemination.

In one embodiment the medical disorder to be treated is a T cell derived lymphoproliferative disorder, selected preferably from the group consisting of angioimmunoblastic T cell lymphoma, cutaneous T cell lymphoma and T cell lymphoma with a leukemic dissemination.

A further aspect of the invention relates to a genetically modified immune cell as described herein expressing the inventive CAR for use as a medicament in the treatment of an autoantibody-dependent autoimmune disease.

In a preferred embodiment the autoimmune disease is selected from systemic lupus erythematosus (SLE) or rheumatoid arthritis.

Only recently, CAR-T cells have also been discussed as a targeted approach to treat autoantibody-mediated diseases (Ellebrecht et al. (2016) Science 353:179-184). The ability to target CXCR5 would inhibit co-localization of autoreactive B cells and Tfh cells, which would be of great benefit for the treatment of autoimmune diseases.

Mild forms of autoimmune disease are usually initially treated with nonsteroidal anti-inflammatory drugs (NSAID) or disease-modifying anti-rheumatic drugs (DMARD). More severe forms of rheumatoid arthritis (RA) and systemic lupus erythematosus (SLE), involving organ dysfunction due to active disease, usually are treated with steroids in conjunction with strong immunosuppressive agents such as cyclophosphamide, a cytotoxic agent that targets cycling cells. Only recently belimumab, an antibody targeting the cytokine BAFF, which is found at elevated levels in serum of patients with autoimmune diseases, received approval by the Food and Drug Administration (FDA) for its use in SLE.

However, only newly formed B cells rely on BAFF for survival in humans, whereas memory B cells and plasma cells are less susceptible to selective BAFF inhibition (Jacobi et al. (2010) Arthritis Rheum 62:201-210). For rheumatoid arthritis (RA), TNF inhibitors were the first licensed biological agents, followed by abatacept, rituximab, and tocilizumab and others: they suppress key inflammatory pathways involved in joint inflammation and destruction, which, however, comes at the price of an elevated infection risk due to relative immunosuppression (Chan et al. (2010) Nat Rev Immunol 10:301-316, Keyser (2011) Curr Rheumatol Rev 7:77-87).

Rituximab, a monoclonal antibody that depletes B cells from the circulation, in particular has increasingly been prescribed for the treatment of RA but also for granulomatosis with polyangiitis and other antineutrophil cytoplasmic antibody-associated vasculitides. But rituximab is not without risks and carries a similar adverse event risk rate as cyclophosphamide (Shah et al. (2015) ImmunoTargets and Therapy 4:173-183). Hence, more fine-tuned and longer-lasting approaches targeting autoreactive B cells and autoantibody responses are warranted.

The invention relates further to methods of treatment of the medical conditions described herein, comprising typically the administration of a therapeutically effective amount of the CAR, or immune cell expressing said CAR, to a patient in need of said treatment.

The invention is demonstrated by way of example by the following figures. The figures are to be considered as providing a further description of potentially preferred embodiments that enhance the support of one or more non-limiting embodiments of the invention.

BRIEF DESCRIPTION OF THE DRAWINGS

FIG. 3: List of preferred constructs and potential combinations of the various structural elements of the CARs as described herein.

FIG. 4: Sequence comparisons between the mAb binding regions and the preferred humanized sequences employed in the present CAR. Alignments are depicted showing sequence identity between the rat and humanized hHC (SEQ ID NO: 55 and SEQ ID NO: 57, respectively) and rat and humanized hLC sequences (SEQ ID NO: 58 and 59, respectively). As is depicted, 89% sequence identity is evident between humanized and rat hHC sequences (SEQ ID NO: 56), and 93% sequence identity is evident between humanized and rat hLC sequences (SEQ ID NO: 59).

FIG. 5: Sequence depiction of the DNA sequence encoding the mAb binding regions hHC, in particular showing a sequence comparison between the original (SEQ ID NO: 61) and codon optimized (CO) (SEQ ID NO: 62) DNA sequences encoding the humanized hHC.

FIG. 6: Sequence depiction of the DNA sequence encoding the mAb binding region hLC, in particular showing a sequence comparison between the original (SEQ ID NO: 63) and codon optimized (CO) (SEQ ID NO: 64) DNA sequences encoding the humanized hLC.

DETAILED DESCRIPTION OF THE INVENTION

Figure 1:
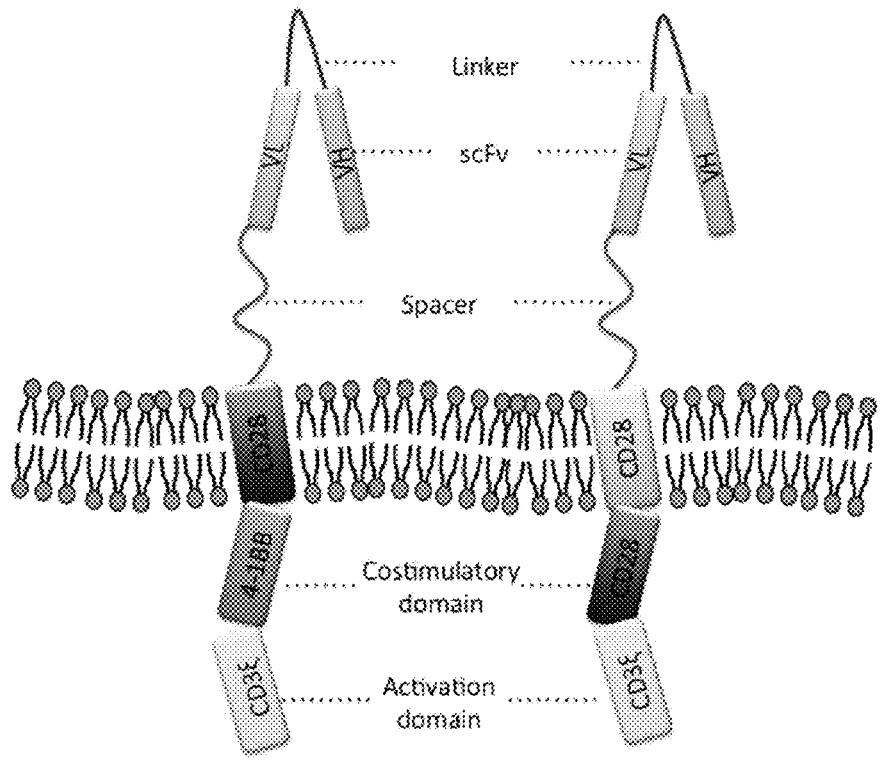
FIG. 1: Schematic representation of preferred CAR structures. Depicted are the VL and VH domains of the antigen-binding domain, including the linker positioned between the VH and VL domains. Also depicted is the spacer region, positioned between the antigen-binding domain and the transmembrane domain. Also depicted are variants of the intracellular domain, comprising for example co-stimulatory and activation domains.
Figure 2:
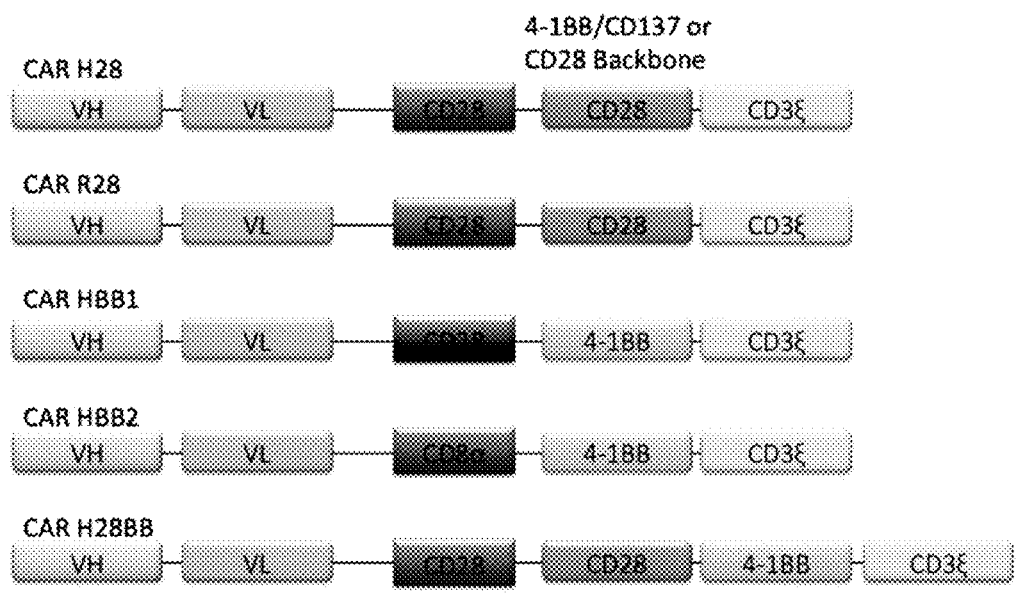
FIG. 2: Schematic representation of preferred CAR constructs H28, R28, HBB1, HBB2, and H28BB. The preferred constructs of the invention comprise variants of the transmembrane domain, costimulatory and activation domains. Essentially, the preferred embodiments of the invention enable exchange of these various domains, preferably of those particular embodiments disclosed herein, although also encompassing additional domains with analogous functions known to one skilled in the art.

Chimeric Antigen Receptors:

According to the present invention, a chimeric antigen receptor polypeptide (CAR), comprises an extracellular antigen-binding domain, comprising an antibody or antibody fragment that binds a target antigen, a transmembrane domain, and an intracellular domain. CARs are typically described as comprising an extracellular ectodomain (antigen-binding domain) derived from an antibody and an endodomain comprising signaling modules derived from T cell signaling proteins.

In a preferred embodiment, the ectodomain preferably comprises variable regions from the heavy and light chains of an immunoglobulin configured as a single-chain variable fragment (scFv). The scFv is preferably attached to a hinge region that provides flexibility and transduces signals through an anchoring transmembrane moiety to an intracellular signaling domain. The transmembrane domains originate preferably from either CD8α or CD28. In the first generation of CARs the signaling domain consists of the zeta chain of the TCR complex. The term "generation" refers to the structure of the intracellular signaling domains. Second generation CARs are equipped with a single costimulatory domain originated from CD28 or 4-1BB. Third generation CARs already include two costimulatory domains, e.g. CD28, 4-1BB, ICOS or OX40, CD3 zeta. The present invention preferably relates to a second or third generation CAR.

In various embodiments, genetically engineered receptors that redirect cytotoxicity of immune effector cells toward B cells are provided. These genetically engineered receptors referred to herein as chimeric antigen receptors (CARs). CARs are molecules that combine antibody-based specificity for a desired antigen (e.g., CXCR5) with a T cell receptor-activating intracellular domain to generate a chimeric protein that exhibits a specific anti-CXCR5 cellular immune activity. As used herein, the term, "chimeric," describes being composed of parts of different proteins or DNAs from different origins.

CARs contemplated herein, comprise an extracellular domain (also referred to as a binding domain or antigen-binding domain) that binds to CXCR5, a transmembrane domain, and an intracellular domain, or intracellular signaling domain. Engagement of the anti-CXCR5 antigen binding domain of the CAR with CXCR5 on the surface of a target cell results in clustering of the CAR and delivers an activation stimulus to the CAR-containing cell. The main characteristic of CARs are their ability to redirect immune effector cell specificity, thereby triggering proliferation, cytokine production, phagocytosis or production of molecules that can mediate cell death of the target antigen expressing cell in a major histocompatibility complex (MHC) independent manner, exploiting the cell specific targeting abilities of monoclonal antibodies, soluble ligands or cell specific co-receptors.

In various embodiments, a CAR comprises an extracellular binding domain that comprises a humanized CXCR5-specific binding domain; a transmembrane domain; one or more intracellular signaling domains. In particular embodiments, a CAR comprises an extracellular binding domain that comprises a humanized anti-CXCR5 antigen binding fragment thereof; one or more spacer domains; a transmembrane domain; one or more intracellular signaling domains.

The "extracellular antigen-binding domain" or "extracellular binding domain" are used interchangeably and provide a CAR with the ability to specifically bind to the target antigen of interest, CXCR5. The binding domain may be derived either from a natural, synthetic, semi-synthetic, or recombinant source. Preferred are scFv domains.

"Specific binding" is to be understood as via one skilled in the art, whereby the skilled person is clearly aware of various experimental procedures that can be used to test binding and binding specificity. Methods for determining equilibrium association or equilibrium dissociation constants are known in the art. Some cross-reaction or background binding may be inevitable in many protein-protein interactions; this is not to detract from the "specificity" of the binding between CAR and epitope. "Specific binding" describes binding of an anti-CXCR5 antibody or antigen binding fragment thereof (or a CAR comprising the same) to CXCR5 at greater binding affinity than background binding. The term "directed against" is also applicable when considering the term "specificity" in understanding the interaction between antibody and epitope.

An "antigen (Ag)" refers to a compound, composition, or substance that can stimulate the production of antibodies or a T cell response in an animal. In particular embodiments, the target antigen is an epitope of a CXCR5 polypeptide. An "epitope" refers to the region of an antigen to which a binding agent binds. Epitopes can be formed both from contiguous amino acids or noncontiguous amino acids juxtaposed by tertiary folding of a protein.

"Single-chain Fv" or "scFv" antibody fragments comprise the VH and VL domains of an antibody, wherein these domains are present in a single polypeptide chain and in either orientation {e.g., VL-VH or VH-VL). Generally, the scFv polypeptide further comprises a polypeptide linker between the VH and VL domains which enables the scFv to form the desired structure for antigen binding. In preferred embodiments, a CAR contemplated herein comprises antigen-specific binding domain that is an scFv and may be a murine, human or humanized scFv. Single chain antibodies may be cloned from the V region genes of a hybridoma specific for a desired target. In particular embodiments, the antigen-specific binding domain that is a humanized scFv that binds a human CXCR5 polypeptide. An illustrative example of a variable heavy chain that is suitable for constructing anti-CXCR5 CARs contemplated herein include, but are not limited to the amino acid sequence set forth in SEQ ID NO: 9. An illustrative example of a variable light chain that is suitable for constructing anti-CXCR5 CARs contemplated herein include, but is not limited to the amino acid sequence set forth in SEQ ID NO: 11.

Antibodies and Antibody Fragments:

The CAR comprises an extracellular antigen-binding domain, comprising an antibody or antibody fragment that binds CXCR5 polypeptide. Antibodies or antibody fragments of the invention therefore include, but are not limited to polyclonal, monoclonal, bispecific, human, humanized or chimeric antibodies, single chain fragments (scFv), single variable fragments (ssFv), single domain antibodies (such as VHH fragments from nanobodies), Fab fragments, F(ab')$_2$ fragments, fragments produced by a Fab expression library, anti-idiotypic antibodies and epitope-binding fragments or combinations thereof of any of the above, provided that they retain similar binding properties of the CAR described herein, preferably comprising the corresponding CDRs, or VH and VL regions as described herein. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments comprised by the CAR of the invention, either produced by the modification of whole antibodies or synthesized de novo using recombinant DNA methodologies.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The CARs of the invention are intended to bind against mammalian, in particular human, protein targets. The use of protein names may correspond to either mouse or human versions of a protein.

Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore.

Humanized antibodies comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807, 715; 5,866,692; 6,331,415; 5,530,101; 5,693,761; 5,693, 762; 5,585,089; 6,180,370; 5,225,539; 6,548,640.

The term humanized antibody means that at least a portion of the framework regions, and optionally a portion of CDR regions or other regions involved in binding, of an immunoglobulin is derived from or adjusted to human immunoglobulin sequences. The humanized, chimeric or partially humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin.

As used herein, human or humanized antibody or antibody fragment means an antibody having an amino acid sequence corresponding to that of an antibody produced by a human and/or has been made using any of the techniques for making human antibodies known in the art or disclosed herein. Human antibodies or fragments thereof can be selected by competitive binding experiments, or otherwise, to have the same epitope specificity as a particular mouse antibody. The humanized antibodies of the present invention surprisingly share the useful functional properties of the mouse antibodies to a large extent. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

Variable Regions and CDRs

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies.

There are a number of techniques available for determining CDRs, such as an approach based on cross-species sequence variability (i.e., Kabat et al. Sequences of Proteins of Immunological Interest, (5th ed., 1991, National Institutes of Health, Bethesda Md.)); and an approach based on crystallographic studies of antigen-antibody complexes (Al-Lazikani et al. (1997) J. Molec. Biol. 273:927-948). Alternative approaches include the IMGT international ImMunoGeneTics information system, (Marie-Paule Lefranc). The Kabat definition is based on sequence variability and is the most commonly used method. The Chothia definition is based on the location of the structural loop regions, wherein the AbM definition is a compromise between the two used by Oxford Molecular's AbM antibody modelling software (refer www.bioinf.org.uk: Dr. Andrew C. R. Martin's Group). As used herein, a CDR may refer to CDRs defined by one or more approach, or by a combination of these approaches.

In some embodiments, the invention provides an antibody or fragment thereof incorporated into a CAR, wherein said antibody or fragment thereof comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 70%, 75%, 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

Additional Components of the CAR

In certain embodiments, the CARs contemplated herein may comprise linker residues between the various domains, added for appropriate spacing and conformation of the molecule, for example a linker comprising an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids.

Illustrative examples of linkers include glycine polymers; glycine-serine polymers; glycine-alanine polymers; alanine-serine polymers; and other flexible linkers known in the art, such as the Whitlow linker. Glycine and glycine-serine polymers are relatively unstructured, and therefore may be able to serve as a neutral tether between domains of fusion proteins such as the CARs described herein.

In particular embodiments, the binding domain of the CAR is followed by one or more "spacers" or "spacer polypeptides," which refers to the region that moves the antigen binding domain away from the effector cell surface to enable proper cell/cell contact, antigen binding and activation. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain comprises the CH2 and CH3 domains of IgG1 or IgG4. In one embodiment the Fc-binding domain of such a spacer/hinge region is mutated in a manner that prevents binding of the CAR to Fc-receptors expressed on macrophages and other innate immune cells.

The binding domain of the CAR may in some embodiments be followed by one or more "hinge domains," which play a role in positioning the antigen binding domain away from the effector cell surface to enable proper cell/cell contact, antigen binding and activation. A CAR may comprise one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8 alpha, CD4, CD28, PD1, CD 152, and CD7, which may be wild-type hinge regions from these molecules or may be altered. In another embodiment, the hinge domain comprises a PD1, CD 152, or CD8 alpha hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from the alpha, beta or zeta chain of the T-cell receptor, CD3ε, CD3ζ, CD4, CD5, CD8 alpha, CD9, CD 16, CD22, CD27, CD28, CD33, CD37, CD45, CD64, CD80, CD86, CD 134, CD 137, CD 152, CD 154, and PD1. In one embodiment, the CARs contemplated herein comprise a TM domain derived from CD8 alpha or CD28

In particular embodiments, CARs contemplated herein comprise an intracellular signaling domain. An "intracellular signaling domain," refers to the part of a CAR that participates in transducing the message of effective anti-CXCR5 CAR binding to a human CXCR5 polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. CARs contemplated herein comprise one or more co-stimulatory signaling domains to enhance the efficacy, expansion and/or memory formation of T cells expressing CAR receptors. As used herein, the term, "co-stimulatory signaling domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

In one embodiment, the CAR comprises an intracellular domain, which comprises a co-stimulatory domain and a signalling (activation) domain. The CAR construct may therefore include an intracellular signaling domain (CD3 zeta) of the native T cell receptor complex and one or more co-stimulatory domains that provide a second signal to stimulate full T cell activation. Co-stimulatory domains are thought to increase CAR T cell cytokine production and facilitate T cell replication and T cell persistence. Co-stimulatory domains have also been shown to potentially prevent CAR T cell exhaustion, increase T cell antitumor activity, and enhance survival of CAR T cells in patients. As a non-limiting example, CAR constructs with the 4-1BB co-stimulatory domain have been associated with gradual, sustained expansion and effector function, increased persistence, and enriched central memory cells (TCM) in the T cell subset composition in preclinical studies. 4-1BB is a member of the tumor necrosis factor (TNF) superfamily, and it is an inducible glycoprotein receptor in vivo that is primarily expressed on antigen-activated CD4 and CD8 T cells. As a non-limiting example, CD28 is member of the immunoglobulin (Ig) superfamily. It is constitutively expressed on resting and activated CD4 and CD8 T cells and plays a critical role in T cell activation by stimulating the PI3K-AKT signal transduction pathway. In one embodiment, the intracellular domain comprises both 4-1BB and CD28 costimulatory domains. Other co-stimulatory domains comprise ICOS and OX40 that can be combined with the CD3 zeta signaling (activation) domain.

Polypeptides

"Peptide" "polypeptide", "polypeptide fragment" and "protein" are used interchangeably, unless specified to the contrary, and according to conventional meaning, i.e., as a sequence of amino acids.

Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

In various embodiments, the CAR polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Nucleic Acids

As used herein, the terms "polynucleotide" or "nucleic acid molecule" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100%) sequence identity to any of the reference sequences described herein, typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus {e.g., herpes simplex virus), poxvirus, baculovirus, papillomavirus, and papovavirus {e.g., SV40). Examples of expression vectors are pClneo vectors (Promega) for expression in mammalian cells; pLenti4/V5-DEST™, pLenti6/VN5-DEST™, and pLenti6.2/V5-GW/lacZ (Invitrogen) for lentivirus-mediated gene transfer and expression in mammalian cells. In particular embodiments, the coding sequences of the chimeric proteins disclosed herein can be ligated into such expression vectors for the expression of the chimeric protein in mammalian cells. The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Vectors

In particular embodiments, a cell (e.g., an immune effector cell, such as a T cell) is transduced with a retroviral vector, e.g., a lentiviral vector, encoding a CAR. For example, an immune effector cell is transduced with a vector encoding a CAR that comprises a humanized anti-CXCR5 antibody or antigen binding fragment that binds a CXCR5 polypeptide, with a transmembrane and intracellular signaling domain, such that these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lenti virus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In further embodiments of the invention, CrispR/Cas and TALEN-mediated insertion of the CXCR5 CAR encoding nucleic acid may be employed. Appropriate vectors for CrispR/Cas and TALEN-mediated insertion are known to a skilled person.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus.

In a preferred embodiment the invention therefore relates to a method for transfecting cells with an expression vector encoding a CAR. For example, in some embodiments, the vector comprises additional sequences, such as sequences that facilitate expression of the CAR, such a promoter, enhancer, poly-A signal, and/or one or more introns. In preferred embodiments, the CAR-coding sequence is flanked by transposon sequences, such that the presence of a transposase allows the coding sequence to integrate into the genome of the transfected cell.

In some embodiments, the genetically transformed cells are further transfected with a transposase that facilitates integration of a CAR coding sequence into the genome of the transfected cells. In some embodiments the transposase is provided as DNA expression vector. However, in preferred embodiments, the transposase is provided as an expressible RNA or a protein such that long-term expression of the transposase does not occur in the transgenic cells. For example, in some embodiments, the transposase is provided as an mRNA (e.g., an mRNA comprising a cap and poly-A tail). Any transposase system may be used in accordance with the embodiments of the present invention. However, in some embodiments, the transposase is salmonid-type Tel-like transposase (SB). For example, the transposase can be the so called "Sleeping beauty" transposase, see e.g., U.S. Pat. No. 6,489,458, incorporated herein by reference. In some embodiments, the transposase is an engineered enzyme with increased enzymatic activity. Some specific examples of transposases include, without limitation, SB 10, SB 11 or SB 100X transposase (see, e.g., Mates et al, 2009, Nat Genet. 41(6):753-61, or U.S. Pat. No. 9,228,180, herein incorporated by reference). For example, a method can involve electroporation of cells with an mRNA encoding an SB 10, SB 11 or SB 100X transposase.

Sequence Variants:

Sequence variants of the claimed nucleic acids, proteins, antibodies, antibody fragments and/or CARs, for example those defined by % sequence identity, that maintain similar binding properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

The recitation "sequence identity" as used herein refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, He, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. Substitutions may be carried out that preferably do not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, lie and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened.

Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

Genetically Modified Cells and Immune Cells

The present invention contemplates, in particular embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction—permanently or transiently—of extra genetic material in the form of DNA or RNA into the total genetic material in a cell that restores, corrects, or modifies expression of a gene, or for the purpose of expressing a therapeutic polypeptide, e.g., a CAR. In particular embodiments, the CARs contemplated herein are introduced and expressed in immune effector cells so as to redirect their specificity to a target antigen of interest, e.g., a CXCR5 polypeptide.

An "immune cell" or "immune effector cell" is any cell of the immune system that has one or more effector functions (e.g., cytotoxic cell killing activity, secretion of cytokines, induction of ADCC and/or CDC). An immune effector cell can be also differentiated from iPSCs (induced pluriotent stem cells)

Immune effector cells of the invention can be autologous/autogeneic ("self") or non-autologous ("non-self," e.g., allogeneic, syngeneic or xenogeneic). "Autologous," as used herein, refers to cells from the same subject, and represent a preferred embodiment of the invention. "Allogeneic," as used herein, refers to cells of the same species that differ genetically to the cell in comparison.

"Syngeneic," as used herein, refers to cells of a different subject that are genetically identical to the cell in comparison. "Xenogeneic," as used herein, refers to cells of a different species to the cell in comparison. In preferred embodiments, the cells of the invention are autologous or allogeneic.

Illustrative immune effector cells used with the CARs contemplated herein include T lymphocytes. The terms "T cell" or "T lymphocyte" are art-recognized and are intended to include thymocytes, immature T lymphocytes, mature T lymphocytes, resting T lymphocytes, cytokine-induced killer cells (CIK cells) or activated T lymphocytes. Cytokine-induced killer (CIK) cells are typically CD3- and CD56-positive, non-major histocompatibility complex (MHC)-restricted, natural killer (NK)-like T lymphocytes. A T cell can be a T helper (Th; CD4+ T cell) cell, for example a T helper 1 (Th1) or a T helper 2 (Th2) cell. The T cell can be a cytotoxic T cell (CTL; CD8+ T cell), CD4+CD8+ T cell, CD4 CD8 T cell, or any other subset of T cells. Other illustrative populations of T cells suitable for use in particular embodiments include naive T cells and memory T cells and stem cell-like memory cells TSCM).

For example, when reintroduced back to patients after autologous cell transplantation, the T cells modified with the CAR of the invention as described herein may recognize and kill tumor cells. CIK cells may have enhanced cytotoxic activity compared to other T cells, and therefore represent a preferred embodiment of an immune cell of the present invention.

As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Progenitors can be iPSCs that become immune effector cells under defined culture conditions.

The present invention provides methods for making the immune effector cells which express the CAR contemplated herein. In one embodiment, the method comprises transfecting or transducing immune effector cells isolated from an individual such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells described herein, the source of cells is obtained from a subject. In particular embodiments, the CAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation, antibody-conjugated bead-based methods such as MACS™ separation (Miltenyi). In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells can be further isolated by positive or negative selection techniques. One method for use herein is cell sorting and/or selection via negative magnetic immunoadherence or flow cytometry that uses a cocktail of monoclonal antibodies directed to cell surface markers present on the cells negatively selected.

PBMC may be directly genetically modified to express CARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells.

In some embodiments, the immune cell of the present invention, for example the T cells described herein, can be obtained from inducible pluripotent stem cells (iPSCs) using methods known to a skilled person.

Accepted approaches for producing CAR T cells rely on the genetic modification and expansion of mature circulating T-cells. Such processes utilize autologous T cells and reduce risk of graft-versus-host (GvHD) disease from allogeneic T cells through endogenous TCR expression as well as rejection through MHC incompatibility. As an alternative, direct in vitro differentiation of engineered T cells from pluripotent stem cells, such as inducible pluripotent stem cells, provides an essentially unlimited source of cells that can be genetically modified to express the CAR of the present invention. In some embodiments, a so-called master iPSC line can be maintained, which represents a renewable source for consistently and repeatedly manufacturing homogeneous cell products. In some embodiments, the transformation of a master iPSC cell line with the CAR encoding nucleic acid is contemplated, prior to expansion and differentiation to the desired immune cell, preferably T cell. T lymphocytes can for example be generated from iPSCs, such that iPSCs could be modified with the CAR encoding nucleic acids and subsequently expanded and differentiated to T cells for administration to the patient. Differentiation to the appropriate immune cell, such a T cell, could also be conducted from the iPSCs before transformation with CAR encoding nucleic acids and expansion prior to administration. All possible combinations of iPSC expansion, genetic modification and expansion to provide suitable numbers of cells for administration are contemplated in the invention.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein (e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAR proteins.

In one embodiment, the invention provides a method of storing genetically modified murine, human or humanized CAR protein expressing immune effector cells which target a CXCR5 protein, comprising cryopreserving the immune effector cells such that the cells remain viable upon thawing. A fraction of the immune effector cells expressing the CAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

Compositions and Formulations

The compositions contemplated herein may comprise one or more polypeptides, polynucleotides, vectors comprising same, genetically modified immune effector cells, etc., as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions of the present invention comprise an amount of CAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount. The term prophylactic does not necessarily refer to a complete prohibition or prevention of a particular medical disorder. The term prophylactic also refers to the reduction of risk of a certain medical disorder occurring or worsening in its symptoms.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject {e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject).

It can generally be stated that a pharmaceutical composition comprising the T cells described herein may be administered at a dosage of $10^2$ to $10^{10}$ cells/kg body weight, preferably $10^5$ to $10^7$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells may be administered. CAR expressing cell compositions may be administered multiple times at dosages within these ranges. The cells may be allogeneic, syngeneic, xenogeneic, or autologous to the patient undergoing therapy.

Generally, compositions comprising the cells activated and expanded as described herein may be utilized in the treatment and prevention of diseases that arise in individuals who are immunocompromised. In particular, compositions comprising the CAR-modified T cells contemplated herein are used in the treatment of B cell malignancies. The CAR-modified T cells of the present invention may be administered either alone, or as a pharmaceutical composition in combination with carriers, diluents, excipients, and/or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAR-expressing immune effector cells, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Therapeutic Methods

The genetically modified immune effector cells contemplated herein provide improved methods of adoptive immunotherapy for use in the treatment of medical disorders associated with the presence of pathogenic cells expressing CXCR5 that include, but are not limited to immunoregulatory conditions and hematological malignancies.

As use herein, "medical disorders associated with the presence of pathogenic cells expressing CXCR5" refer to medical conditions, such as a cancer or autoimmune disease, in which the cells involved in pathophysiology of the disease demonstrate expression of CXCR5, and preferably presentation of CXCR5 on the cell surface. The expression of CXCR5 can be determined by various methods known to a skilled person, for example by isolating cells from a patient and assessing these by PCR using primers directed CXCR5 transcripts, immune-staining with anti CXCR5 antibodies, or by analysis by flow cytometry. Such pathogenic cells may typically be pathogenic mature B cells and/or memory B cells, and/or pathogenic T cells and/or T follicular helper cells.

In particular embodiments, compositions comprising CAR-modified T cells contemplated herein are used in the treatment of hematologic malignancies, including but not limited to B cell malignancies such as, for example, non-Hodgkin's lymphoma (NHL), such as B cell NHL or T cell non-Hodgkin's lymphoma, with or without a leukemic tumor cell dissemination.

Non-Hodgkin lymphoma encompasses a large group of cancers of lymphocytes (white blood cells). Non-Hodgkin lymphomas can occur at any age and are often marked by lymph nodes that are larger than normal, fever, and weight loss. Non-Hodgkin lymphomas can also present on extranodal sites, such as the central nervous system, mucosal tissues including lung, intestine, colon and gut. There are many different types of non-Hodgkin lymphoma. For example, non-Hodgkin's lymphoma can be divided into aggressive (fast-growing) and indolent (slow-growing) types.

Non-Hodgkin lymphomas can be derived from B cells and T-cells. As used herein, the term "non-Hodgkin lymphoma" includes both "B cell" and "T cell" non-Hodgkin lymphoma. B cell non-Hodgkin lymphomas (NHL) include Burkitt lymphoma, chronic lymphocytic leukemia/small lymphocytic lymphoma (CLL/SLL), diffuse large B cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B cell non-Hodgkin lymphomas.

T-cell lymphomas account for approximately 15 percent of all NHLs in the United States. There are many different forms of T-cell lymphomas, such as angioimmunoblastic T-cell lymphoma (AITL), which is a mature T-cell lymphoma of blood or lymph vessel immunoblasts. Further forms of T cell lymphomas relate to cutaneous T cell lymphoma and T cell lymphoma with a leukemic dissemination.

Chronic lymphocytic leukemia (CLL) can also be treated with the present CAR, and is an indolent (slow-growing) cancer that causes a slow increase in immature white blood cells (B lymphocytes). Cancer cells spread through the blood and bone marrow, and can also affect the lymph nodes or other organs such as the liver and spleen. CLL eventually causes the bone marrow to fail. A different presentation of the disease is called small lymphocytic lymphoma and localizes mostly to secondary lymphoid organs, e.g. lymph nodes and spleen.

In one embodiment of the invention the CAR or immune cell expressing said CAR is intended for use in the treatment of an autoimmune disease, preferably an auto-antibody-dependent autoimmune disease, preferably an autoimmune disease with an inflammatory component.

Deregulated CXCR5-expressing follicular T-helper (Tfh) cells represent an important mechanism contributing to exacerbated humoral immune responses and autoantibody production during autoimmune diseases. Hence, CXCR5-expressing Tfh cells represent a feasible target in the context of autoimmunity.

The autoimmune disease to be treated is preferably selected from Takayasu Arteritis, Giant-cell arteritis, familial Mediterranean fever, Kawasaki disease, Polyarteritis nodosa, cutanous Polyarteritis nodosa, Hepatitis-associated arteritis, Behcet's syndrome, Wegener's granulomatosis, ANCA-vasculitidies, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, preferably systemic lupus erythematosus (SLE), aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disease, Autoimmune polyglandular syndrome, Autoimmune Addison Syndrome, Pemphigus vulgaris, Pemphigus foliaceus, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, most preferably SLE.

Systemic lupus erythematosus (SLE), also known as lupus, is an autoimmune disease in which the body's immune system attacks healthy tissue in various parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face.

Follicular T-helper cells (Tfh) cells have been recently discovered as the major cellular reservoir of Human Immunodeficiency Virus (HIV) among CD4+ T helper cells (Leong et al. 2017, Frontiers in Immunology, 8:622) and CAR immune cells expressing the CAR of the present invention could target the follicular reservoir of HIV-producing T helper cells. As such, the CAR of the present invention may be used in eliminating or inhibiting a reservoir of HIV-producing T helper cells in the treatment of HIV. In one embodiment, the reservoir of HIV-producing T helper cells is therefore to be considered as a group of pathogenic cells expressing CXCR5, in particular pathogenic T cells.

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a B cell malignancy, that can be treated with the cell-based therapeutics and methods disclosed herein. Suitable subjects include laboratory animals (such as mouse, rat, rabbit, or guinea pig), farm animals, and domestic animals or pets (such as a cat or dog). Non-human primates and, preferably, human patients, are included. Typical subjects include human patients that have a B cell malignancy, have been diagnosed with a B cell malignancy, or are at risk or having a B cell malignancy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" or "prophylactic" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In one embodiment, a method of treating a B cell related condition in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

EXAMPLES

The invention is demonstrated by way of the examples disclosed below. The examples provide technical support for and a more detailed description of potentially preferred, non-limiting embodiments of the invention.

In order to demonstrate the functionality and beneficial properties of the CAR described herein, the following examples are to be considered:
- co-cultures of CAR-transduced human T cells with different target cell lines show specific T cell activation by distinct CXCR5+ cell lines; readout was release of IFN-gamma as effector cytokine from T cells;
- cytotoxicity assays reveal selective killing of CXCR5+ cell lines; essentially no killing was seen in CXCR5-negative cell lines, e.g. Nalm6 and NCI-H929.
- In vivo experiments relate to using a xenotransplantation NSG mouse model to generate data on i) functionality, ii) off-target reactivity, iii) T cell memory, and iv) biosafety of adoptively transferred CAR-T cells against B-NHL cell lines. For B-NHL the cytolytic capacity of anti-CXCR5 CAR-T cells is compared with an established anti-CD19 CAR-T cell product.

Example 1: Cloning and Plasmid Preparation

Figure 7:
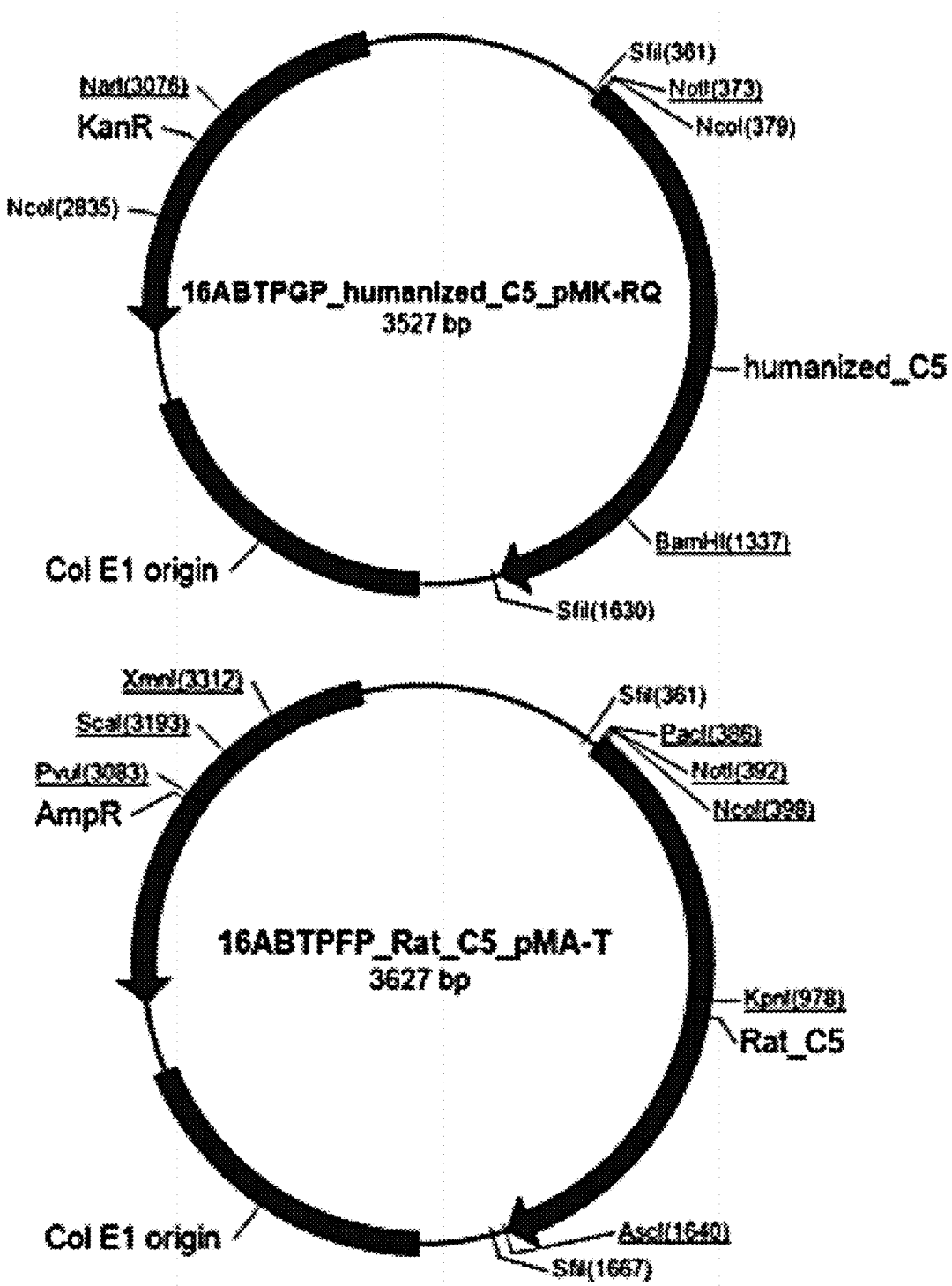
FIG. 7: GeneArt™ Plasmid with the humanized and rat CXCR5-CAR Sequence. Excised scFV was demonstrated using gel electrophoresis.
Figure 7:
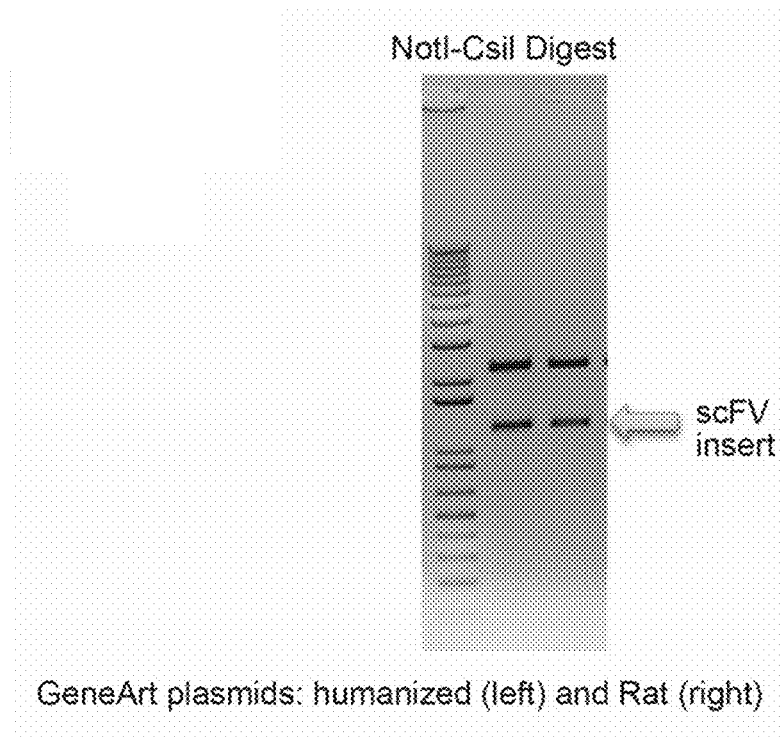
Figure 8:
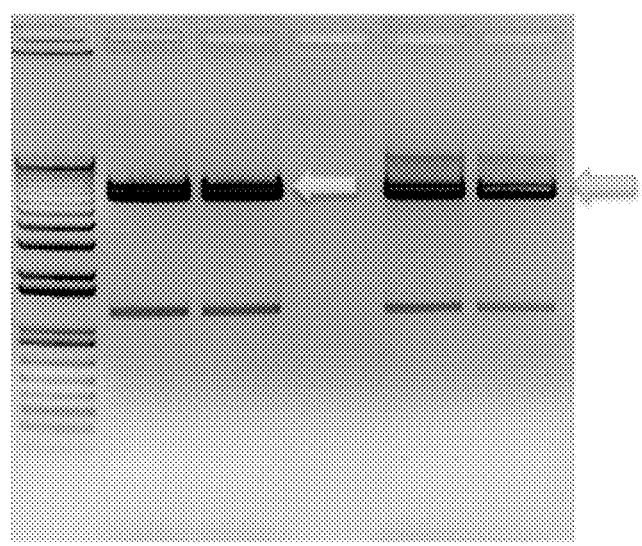
FIG. 8: Gel electrophoresis of the construct and vectors after restriction. Also depicted is a plasmid MP71 comprising the CAR-encoding construct.
Figure 8:
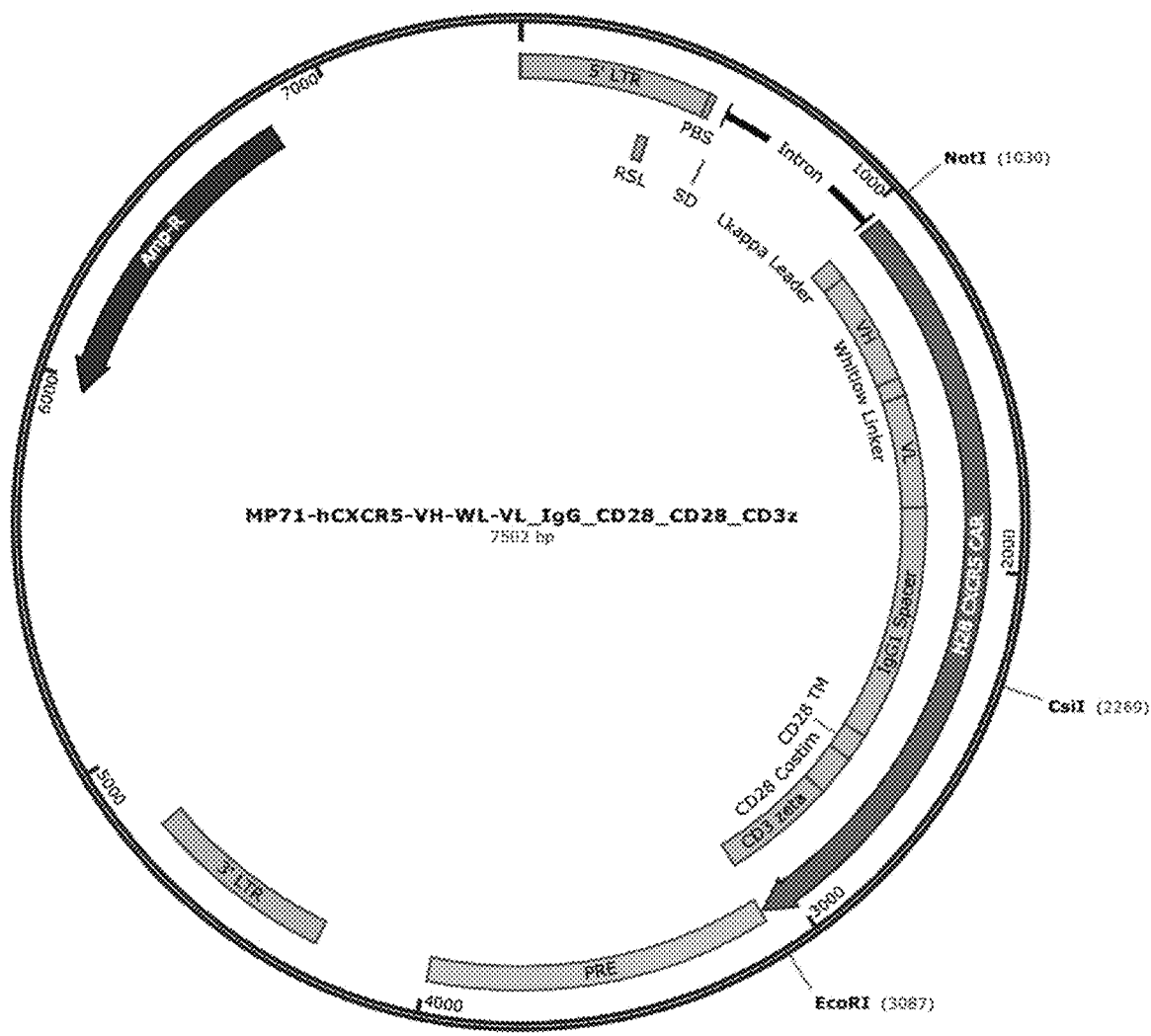

The CAR scFv sequences were synthesized using GeneArt™ (Gene Synthesis Service). Restriction digestion of the synthesized sequences was carried out using NotI and CsiI (FIG. 7) in order to release the scFv insert from the GeneArt plasmid. The retroviral vector MP71, comprising additional CAR sequences, was digested with NotI and CsiI to enable subsequent ligation of the isolated scFv insert into the CAR construct in the vector. The digested vector was subsequently dephosphorylated. The fragments were separated using gel electrophoresis (FIG. 8) and purified.

The CAR scFv sequence generated as described above was subsequently ligated into the purified vector comprising the additional CAR sequences (50 ng) at a ratio of 3:1. Transformation of the ligation mixture into MACH-1 was carried out. A control digest was conducted and the Mini-preparation was sequenced. The constructs were subsequently re-transformed into MACH-1. A maxi-preparation of the MP71-CXCR5-CAR plasmid was produced.

MP71 is a single (+)-strand-RNA-Virus. Reverse-Transcriptase converts the retroviral RNA-Genome into a DNA copy. The DNA integrates as a provirus at a random position into the target genome. Through cell division the virus reproduces stably as a provirus.

MP71 comprises the following regulatory cis elements:

LTRs (=long terminal repeats) originate from the murine myeloproliferative sarcoma virus (MPSV), which contain promotors. The leader sequence of the vector is derived from the murine embryonic stem cell virus. The PRE (=posttranscriptional regulatory element) originally comes from the woodchuck hepatitis virus.

MP71 has been deactivated, since retroviral genes are missing and it is thus no longer replication-competent. Structural genes were previously introduced separately into two helper plasmids in the packaging cell line. Transfection requires gag, pol and env gene products. Infectious viral particles are released into the cell culture supernatant and can be used to transduce PBLs. High transduction rates with high expression rates in human PBLs can be achieved.

Example 2: Transfection and Transduction

Day 0: Seeding HEK-T(293T)- or GalV-cells for virus production in 6 well plates

Day 1: Transient 3-plasmid transfection for retrovirus production (calcium phosphate transfection). Per well, 18 µg of DNA was used, in 250 mM Cacl2, 150 µl H2O, according to standard protocols. Cells are incubated for 6 h at 37° C., medium is exchanged, further incubation carried out for 48 h at 37° C.

Coating of 24-Well Non-Tissue Culture Plates with Anti-huCD3 Und Anti-huCD28 Antibodies:

Prepare anti-CD3/anti-CD28-antibody solution in PBS (5 µg/ml anti-CD3, 1 µg/ml anti-CD28), 0.5 ml per well. Incubate each well with 0.5 ml antibody solution for 2 h at 37° C., replace with sterile 2% BSA-solution (in water), incubation: 30 min (37° C.). Remove BSA-solution and wash wells with 2 ml PBS.

Purification of PBMCs from 40 ml Blood (~2.5×10$^7$ PBMCs):

Prepare 12.5 ml Ficoll-Gradient medium in 2×50 ml Falcon-Tube, dilute blood with RPMI (+100 IU/ml Penicillin, Streptomycin) to 45 ml, mix and coat with 22.5 ml Blood-Medium-mixture, centrifuge (20 min, 20° C., 1800 rpm, RZB *648, G 17.9). Discard 15 ml upper phase. Transfer remainder of the upper phase with white-milky PBMC-containing intermediate phase to a new 50 ml Falcon-Tube, fill to 45 ml with RPMI (+100 IU/ml Penicillin, Streptomycin) and centrifuge. Re-suspend pellets in 45 ml RPMI (+100 IU/ml Penicillin, Streptomycin), centrifuge, combine pellets in 10-20 ml T cell medium, stain one sample with trypan blue, count cells and add cells at a concentration of 1-1.5×10$^6$ cells/ml (T-cell medium (+100 IU/ml IL-2) corresponds to 400 U/ml clinic-IL2) to the anti-CD3, anti-CD28 coated wells. Centrifuge remainder of PBMCs, suspend in freezing medium and store in Cryo tubes at −80° C.

Day 3: Transduction of PBLs

Remove and filter (0.45 µm filter) viral supernatant from HEK-T- or GalV-cells. Treat stimulated PBMCs with 1.0 ml viral supernatant. Treat stimulated PBLs with 1 ml viral supernatant and centrifuge in the CD3-/CD28-coated wells (90 min, 32° C., 800×g). Final concentration of 100 IU/ml IL2 or 10 ng/ml IL7 und 10 ng/ml IL15, and additionally 4 µg/ml (8 µl) Protamine sulfate.

Day 4: Transduction of PBLs

Filter remaining viral supernatant (4° C.) and second supernatant from HEK-T- or GalV-cells (0.45 µm). Collect 1 ml supernatant from the PBLs. Adjust cytokine concentrations to 100 IU/ml IL2 or 10 ng/ml IL7 und 10 ng/ml IL15, as well as 4 µg/ml (8 µl) Protamine sulfate. Centrifuge at 90 min 800×g at 32° C. 4 h after transduction, PBLs are washed out the 24-well plate in to a T25 cell culture flask. Fresh medium with IL2 or IL7/IL15 is added.

Day 7 to Day 13: Culture PBLs, treat T cell medium with fresh IL2 or IL7/IL15.

Day 13: End T-cell stimulation.

Rinse PBL-cultures from the cell culture flasks, centrifugation, re-suspend pellet in T-cell medium (+10 IU/ml IL2 or 1 ng/ml IL7/IL15).

As of Day 15: Functional assays

Example 3: Functional In Vitro Testing of Anti-CXCR5 CAR T Cells

Confirmation of CXCR5 CAR-Expression on Human T Cells Following Retroviral Transduction:

Evidence is provided on folding and transport of the CAR receptor in context of human T cells. The functionality of the retrovirus transduction protocol is demonstrated.

1) Human peripheral blood leukocytes were purified via a Ficoll gradient. Cells were cultured, stimulated and retrovirally transduced as described above.

Following transduction, cells were further cultured in either IL2 or IL-7/IL15 containing medium prior to the analysis of CXCR5-CAR expression.

2) Transduction rate and viability were assessed by flow cytometry (FACS) analysis. To detect CXCR5-CAR expression, cells were stained with anti-human IgG-antibody that recognizes selectively the human IgG1 or IgG4 section in the spacer region of the CAR construct. A costaining for CD3/CD8 T cells was performed.

Figure 9:
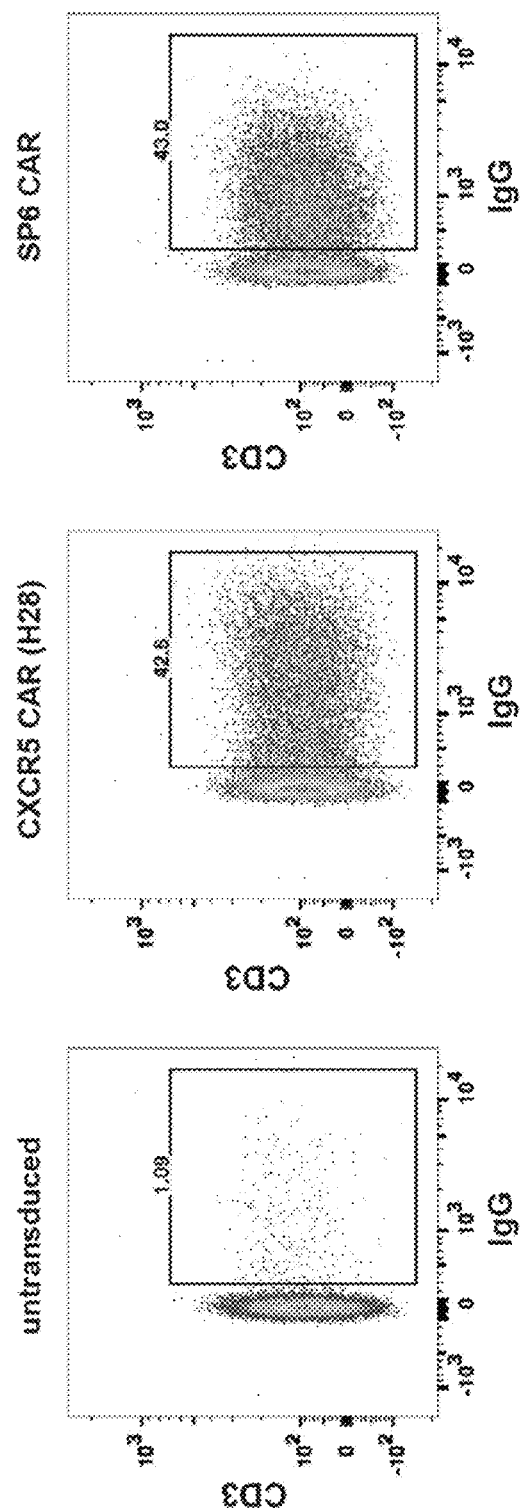
FIG. 9: Confirmation by flow cytometry of CXCR5 CAR-expression on human T cells following retroviral transduction: CAR Expression, construct H28, SP6, untransduced.

Results are demonstrated in FIG. 9.

Co-Cultures of CAR-Transduced Human T Cells with Different Target Cell Lines Show Specific T Cell Activation by Distinct CXCR5$^+$ B-NHL Cell Lines The readout employed for CAR-T cell activation was release of IFN-gamma as an effector cytokine from T cells.

1) Retrovirus-transduced human T cells were generated, as detailed above. The following T cells were employed: CXCR5-CD28 CAR-receptor variant (H28), CXCR5-4-1BB CAR-receptor variant (HBB1), CXCR5-CD28/4-1BB CAR receptor variant (H288BB), SP6-negative control CAR, UT±untransduced T cells.

2) Retrovirally transduced T cells were co-cultured for 18-20 hrs in the presence of the listed cell lines or primary cells; ratio 1:1.

| Cell line | Origin | CXCR5-positivity |
|---|---|---|
| DOHH-2 | immunoblastic B cell lymphoma progressed from follicular centroblastic/centrocytic lymphoma (FL) | yes |
| OCI-Ly7 | diffuse large B cell lymphoma (DLBCL), germinal center type | yes |
| SU-DHL4 | diffuse large B cell lymphoma (DLBCL), germinal center type | yes |

-continued

| | | |
|---|---|---|
| JeKo-1 | mantle cell lymphoma (MCL), B-NHL | yes |
| SC-1 | B follicular lymphoma (B-NHL) | yes |
| JVM-3 | B cell chronic lymphocytic leukemia (B-CLL) | yes |
| NALM-6 | B acute lymphoblastic leukemia (B-ALL) | no |
| REH | B acute lymphoblastic leukemia (B-ALL) | no |
| NCI-H929 | multiple myeloma (MM) | no |
| Jurkat | T cell acute lymphoblastic leukemia (T-ALL) | no |
| SW-620 | Colon adenocarcinoma cell | no |
| HEK293 | Embryonic kidney cell | no |
| HEK-CXCR5 | Embryonic kidney cell transfected with CXCR5 | yes |

| Primary cells | Origin | CXCR5-positivity |
|---|---|---|
| MCL PDX | Patient-derived mantle cell lymphoma xenograft | yes |
| HUVEC | Human Umbilical Vein Endothelial Cells | no |
| HUAEC | Human Umbilical Artery Endothelial Cells | no |
| HA | Human Astrocytes | no |
| HPNC | Human Perineurial Cells | no |
| HCoEpiC | Human Colonic Epithelial Cells | no |
| HN | Human Neurons | no |

3) After co-cultivation, cell-free culture supernatant was sampled and control levels of IFN-gamma were determined. The maximum release value was induced by PMA/ionomycin stimulation of effector T cells; the minimum release value was induced by T cells only.

4) IFN-gamma release was determined in the supernatant by ELISA.

Figure 11:
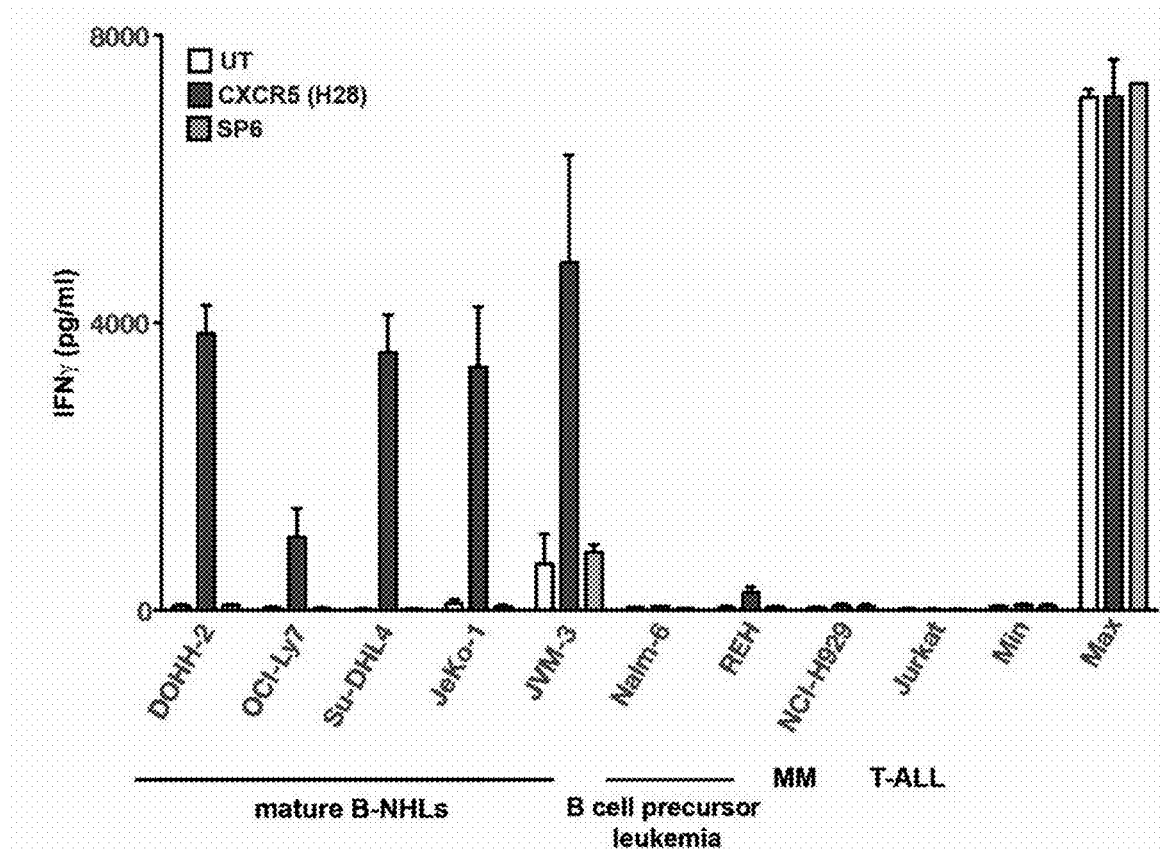
FIG. 11: Co-cultures of CAR-transduced human T cells with different target cell lines show specific T cell activation by distinct CXCR5+ B-NHL and control cell lines. Functional in vitro co-cultivation and IFN-gamma ELISA was performed. The levels of IFN-gamma released is indicative of T cell activation. Untransduced (UT; left bar in each series), CXCR5-CAR expressing T cells (CXCR5 (H28); middle bar in each series) and SP6 T cells (SP6; right bar in each series) were co-cultured with the target cell lines DOHH-2, SU-DHL4, OCI-Ly7, JeKo-1, NALM6, REH, NCI-H929 and Jurkat cells. DOHH-2, SU-DHL4, OCI-Ly7 and JeKo-1 target cells show specific IFN-gamma release in response to treatment with the CXCR5 CAR-T cells of the present invention. JVM-3 also shows IFN-gamma release after treatment.

The results are depicted in FIG. 11.

Cytotoxicity Assays Reveal Selective Killing of CXCR5-Positive Cell Lines; Essentially No Killing was Seen in CXCR5-Negative Cell Lines The $^{51}$Cr-release assay was employed for quantitation of cytotoxic T lymphocyte activity. The assay enables the measurement of target cell cytolysis.

1) Retrovirus-transduced human T cells were generated, as detailed above. CXCR5 CAR-receptor variant (H28) was employed, in addition to SP6-negative control CAR and UT±untransduced T cells.

2) Target cells were labelled with $^{51}$Cr

3) CAR-T cells and labeled target cells were then co-cultured for 4 hrs and the effector cell to target cell ratio was titrated:

Effector to Target Ratio:

80:1

0:1

20:1

10:1

5:1

2.5:1

4) Cell-free cell culture supernatant were harvested,

5) Supernatants were transferred to LUMA-scintillation plates, released $^{51}$Cr was measured in a gamma scintillation counter. The maximum release value was determined by target cells lysed by application to the LUMA plates; the minimum release value was determined using target cells alone.

Figure 12:
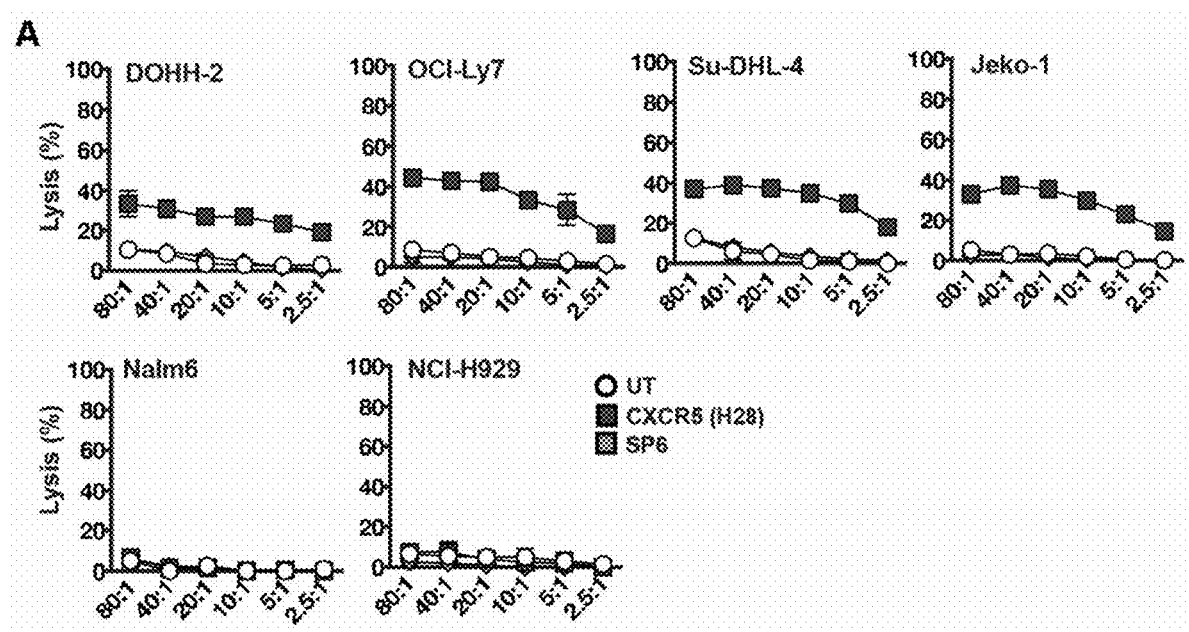
FIG. 12, A and B: Cytotoxicity assays reveal selective killing of CXCR5-postive cell lines; essentially no killing was seen in CXCR5-negative cell lines. Two independent functional in vitro co-cultivation and 51Cr release assays were performed. (A, B) DOHH-2, SU-DHL4, OCI-Ly7, SC-1 (only in (B)), JeKo-1 target cell lines show lysis after treatment with the inventive CAR-Ts, whereas cells not expressing CXCR5 (Nalm6 and NCI-H929) show no lysis.
Figure 12:
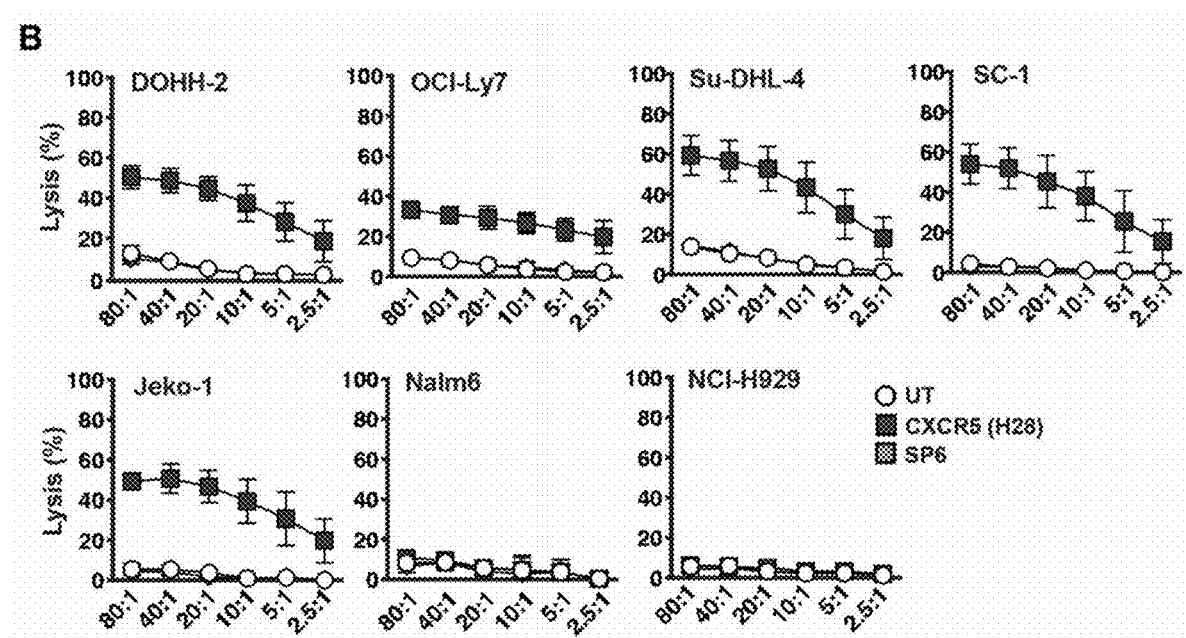

Results are shown in FIG. 12.

Example 4: In Vivo Experiments Using a Xenotransplantation NSG Mouse Model to Assess Adoptively Transferred CAR-T Cells Against B-NHL Cell Lines To demonstrate that CAR-T cells equipped with the diverse anti CXCR5-CAR-variants described herein have effector activity, also under in situ conditions, CXCR5+ B-NHL cell lines are transplanted via an i.v. route into NSG-mice (NOD.Cg-Prkdc$^{scid}$ Il2rg$^{tm1}$Wjl/SzJ).

The CXCR5+ B-NHL cell lines are:

SU-DHL4 (DLBCL), JEKO-1 (mantle cell lymphoma), JVM3 (CLL), DOHH-2 (FL), OCI-Ly7 or SC-1.

A negative control cell line is included, that is REH (ALL), which is not destroyed by the anti CXCR5 CAR T cells in vitro, but is a target for anti CD19 CAR.

These mice are specifically suited for a xenotransplantation because they support human cell growth by cytokine provision and have no T, B, and NK cells for rejection of the transplant. The B-NHL cell lines are also stably transduced with a firefly-luciferase gene that allows for in vivo tumor cell detection by applying luciferin. Progression and distribution of tumors injected are monitored by bioluminescence imaging using the IVIS-system.

Next, when tumor cell growth is confirmed by intensity increase of the luciferase luminescent signal, at about 5-8 days after tumor cell inoculation, human CAR T-cells are administered in a titrated manner, starting with $5 \times 10^5$ up to $5 \times 10^6$ cells per recipient on an i.v. route. Anti-CXCR5 CAR T cells are compared with an anti CD19 CAR and two suitable negative controls, such as an irrelevant SP6 control and an untransduced T cell control.

In 3-5 day intervals, luminescence intensity is measured and growth retardation/progression and disappearance of tumor-cell associated signals is determined in the animals. An observation interval of 28 days is employed. A reduction in luminescence intensity and disappearance of tumor-cell associated signals indicates a therapeutic effect of the CAR T cells.

Figure 13:
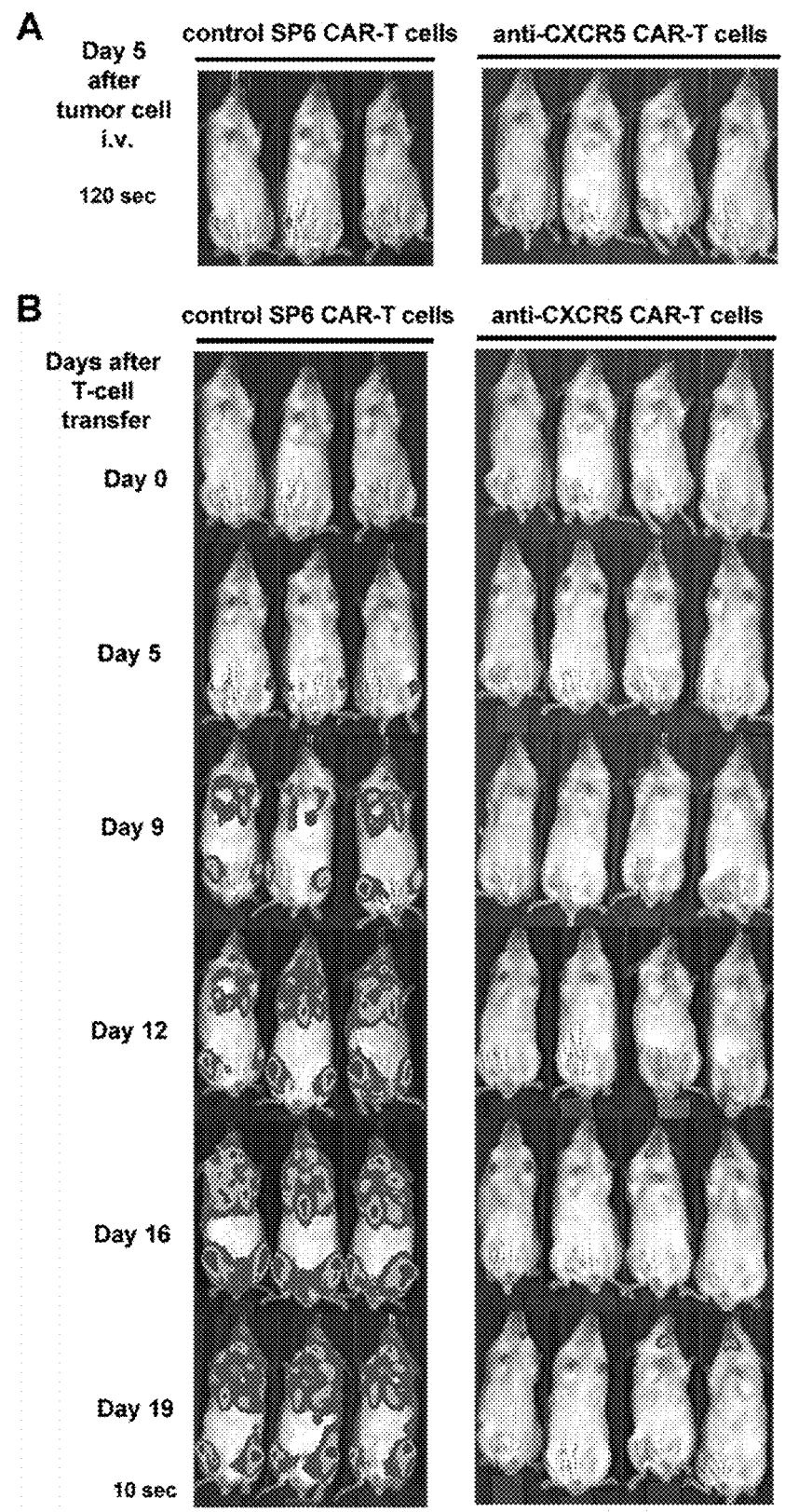
FIG. 13, A-C. CXCR5 redirected CAR-T cells are effective against B-cell non Hodgkin's lymphoma (B-NHL) in a xenografted NSG mouse model. To provide proof-of-concept that the strong in vitro activity of T cells modified with the CXCR5 CAR translates into efficient antitumor activity in vivo, cohorts of NOD.Cg-Prkdc$^{scid}$ Il2rg$^{tm1\ Wjl}$/SzJ (NSG) mice were inoculated i.v. with $5 \times 10^5$ mantle cell lymphoma cells (MCL) JeKo-1 (FIG. 13, A-C), transduced with the luciferase gene in tandem with GFP. NSG mice do not develop T, B, and NK cells and are therefore suitable for tolerance and growth of xenotransplantated human cells. (A) Engraftment of MCL tumors in a xenografted NSG mouse model. Mice were challenged by i.v. transplantation of MCL cells. At day 5 after tumor inoculation, tumor cell growth was visualized by IVIS imaging. To measure onset of tumor burden, imaging was extended to 120 sec (day 0). (B) To follow treatment efficacy and to scale down bioluminescence intensity for better presentation, mice as in (A) were again imaged for 10 sec at day 0. At the same day, mice received $3 \times 10^6$ anti-CXCR5 CAR-transduced T cells (n=4), as a negative control SP6-CAR- transduced T cells (n=3) were employed (day 0). Subsequent IVIS-exposures after CAR-T cell transfer were done at 10 sec to allow better comparisons between day 0 and day 19. (C) Mean values of bioluminescence signals obtained from regions of interests covering the entire body of each mouse are plotted for each group at each time point (C). While essentially all SP6 CAR treated animals had progressive lymphoma disease, characterized by strong luminescence signals over the bone marrow in hind limbs, thoracic and abdominal organs, this was clearly not the case for the CXCR5 CAR treatment group. This provides the first pre-clinical in vivo proof that CXCR5 CAR-T cells have anti-tumor activity to B-NHL lymphoma entities.
Figure 13:
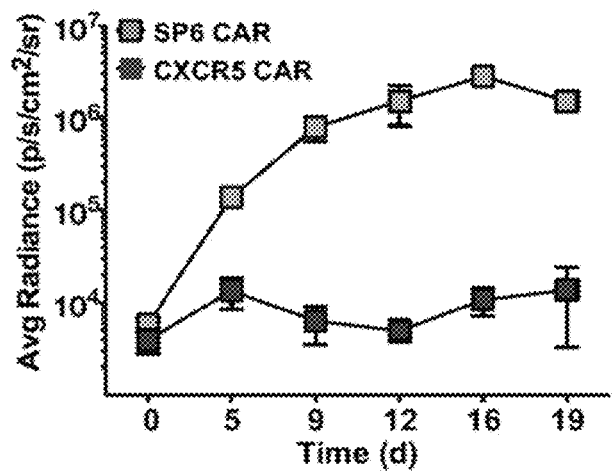

The above experiment was conducted with NOD.Cg-Prkdc$^{scid}$Il2rg$^{tm1\ Wjl}$/SzJ (NSG) mice by inoculating the mice i.v. with $5 \times 10^5$ mantle cell lymphoma cells (MCL) JeKo-1, transduced with the luciferase gene in tandem with GFP (FIG. 13). Mice subsequently received $3 \times 10^6$ anti-CXCR5 CAR-transduced T cells (n=4), and as a negative control SP6-CAR-transduced T cells (n=3) were employed (day 0). Mean values of bioluminescence signals were obtained from regions of interests covering the entire body of each mouse. The data is plotted for each group at each time point (FIG. 13C). While essentially all SP6 CAR treated animals had progressive lymphoma disease, characterized by strong luminescence signals over the bone marrow in hind limbs, thoracic and abdominal organs, this was clearly not the case for the CXCR5 CAR treatment group. This provides the first pre-clinical in vivo proof that CXCR5 CAR-T cells have anti-tumor activity to B-NHL lymphoma entities.

Figure 14:
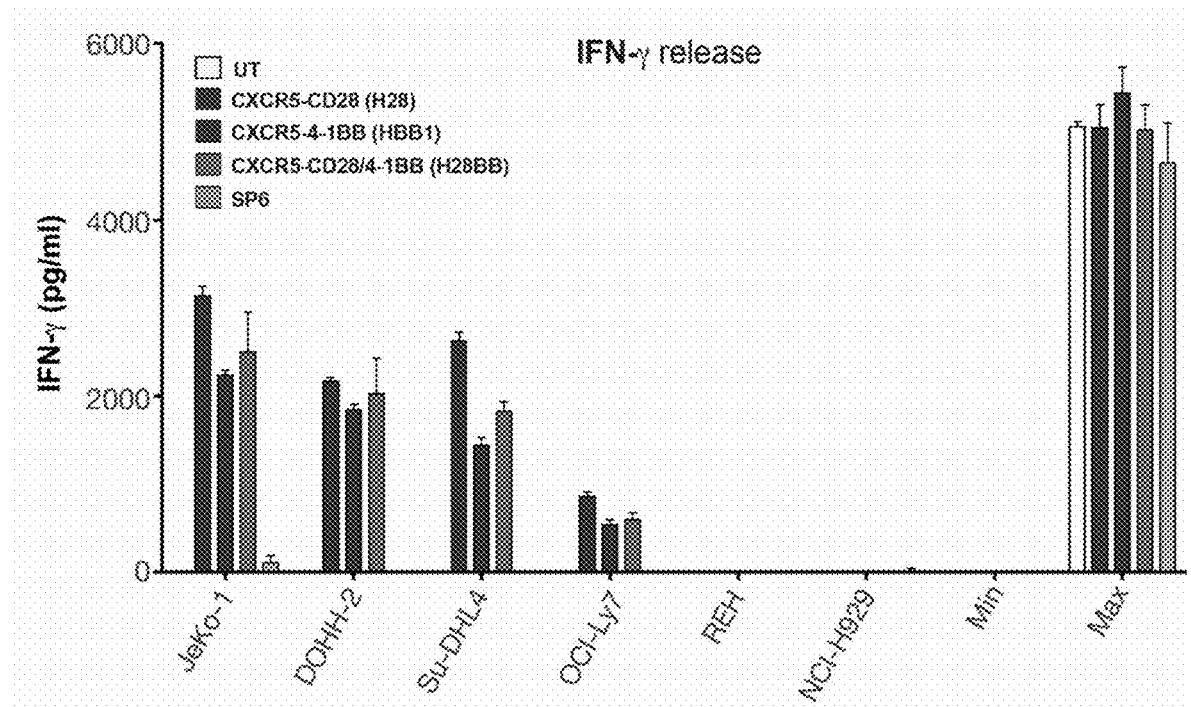
FIG. 14: Co-cultures of CAR-transduced human T cells with different target cell lines show specific T cell activation by distinct CXCR5+ B-NHL and control cell lines. Functional in vitro cocultivation and IFN-gamma (upper panel), IL-2 (middle panel), and TNF-alpha (lower panel) ELISA was performed. The levels of IFN-gamma, IL-2, and TNF-alpha released are indicative of T cell activation and T cell functionality. Untransduced (UT, open bars), CXCR5-CD28 CAR (H28, red bars), CXCR5-41BB (HBB1; blue bars), CXCR5-CD28/41BB (H28BB, green bars) expressing T cells and SP6 T cells (SP6, grey bars) were co-cultured with the target cell lines JeKo-1, DOHH-2, SU-DHL4, OCI-Ly7, REH, and NCI-H929 cells. DOHH-2, SU-DHL4, OCI-Ly7 and JeKo-1 target cells show specific IFN-gamma, IL-2, and TNF-alpha release in response to treatment with the CXCR5 CAR-T cells of the present invention.
Figure 14:
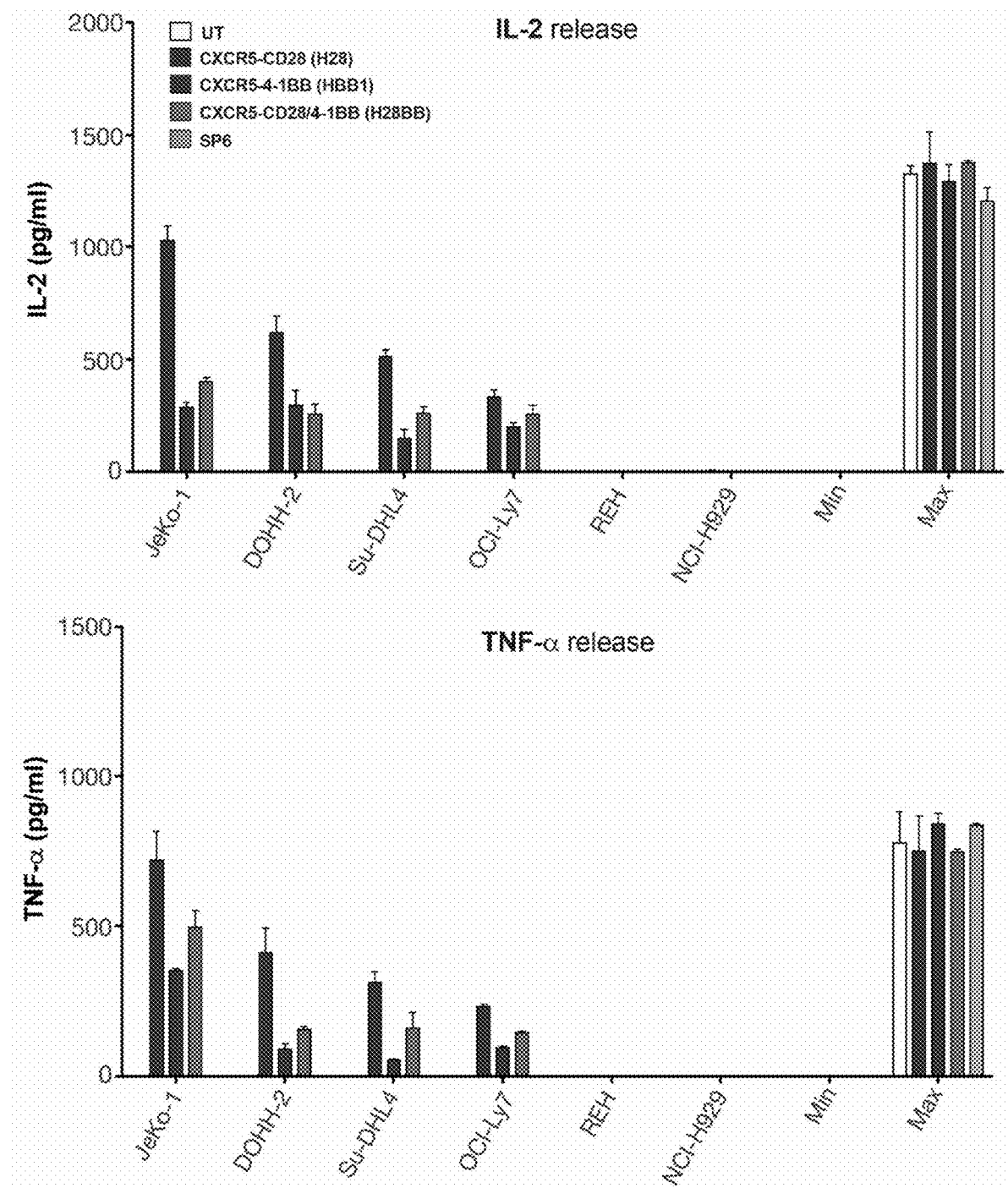

FIG. 14 shows alternative CAR components with (1) 4-1BB or CD28 as a co-stimulatory component and (2) a 3rd generation CAR with CD28 and 4-1BB as co-stimulatory components, and their functional effect in co-culture experiments using CAR T cells with tumor cell lines. Specific activation of CAR-T cells by CXCR5-bearing tumor cells is demonstrated by the release of IFN-gamma, IL-2 and TNF-alpha.

Figure 10:
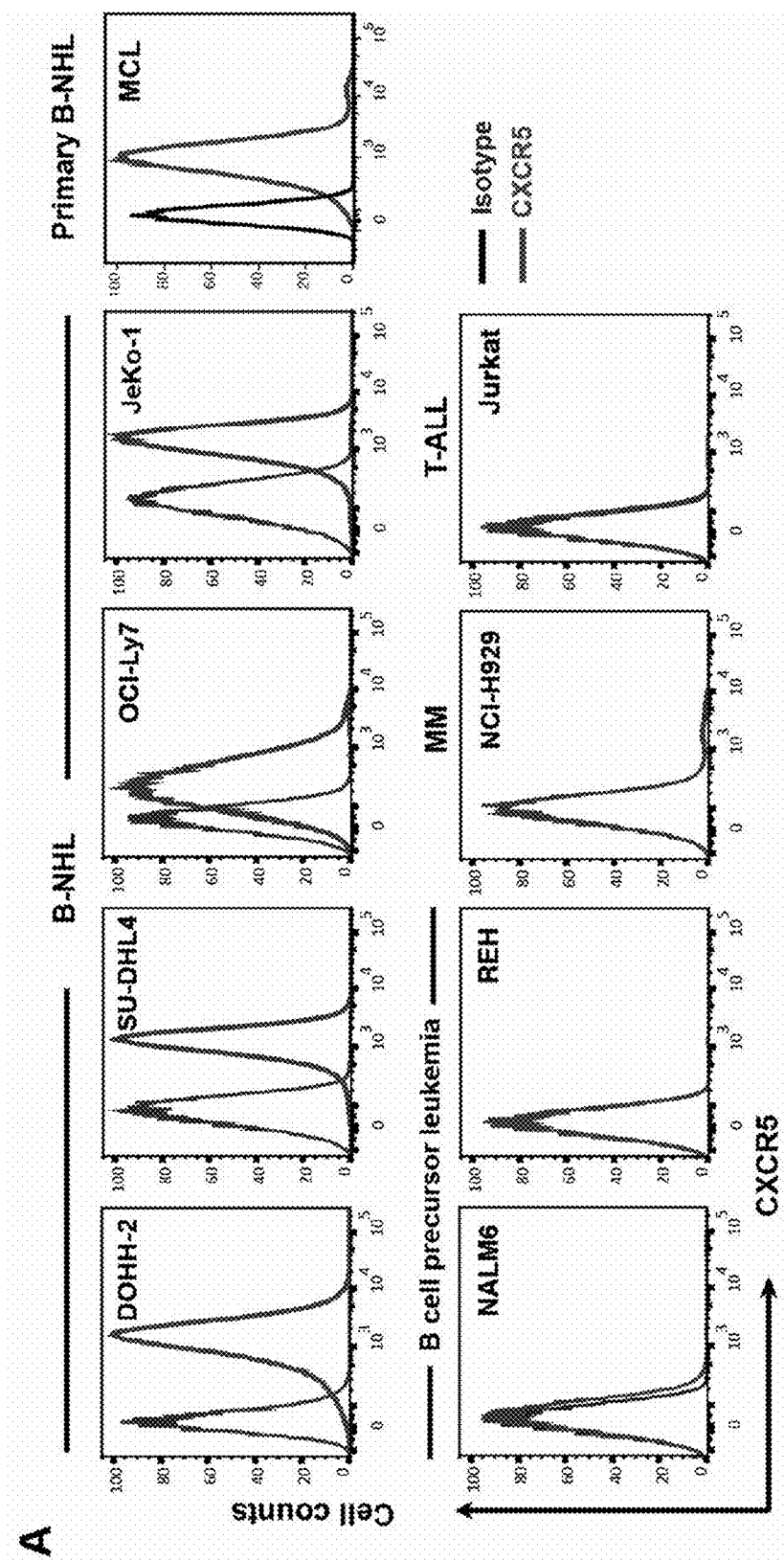
FIG. 10, A-C: CXCR5 expression on the cell types assessed in the functional assays. (A) CXCR5 expression on some of the cell types assessed in the functional assays. Assessed were the B-NHL cell lines DOHH-2, SU-DHL4, OCI-Ly7, and JeKo-1, the primary patient-derived MCL xenograft, the B-ALL cell lines NALM6, REH, the MM cell line NCI-H929, and the T-ALL cell line Jurkat. As can be seen from the analysis, CXCR5 was expressed on the B-NHLs DOHH-2, SU-DHL4, OCI-Ly7 and JeKo-1 cell lines. (B) To rule out that the CXCR5 CAR-T cells of the present invention show crossreactivity with healthy human tissues, CXCR5 expression was assessed on a panel of primary cells derived from human healthy tissues. None of the tested primary human cells (HUVEC, human umbilical vein endothelial cells; HUAEC, human umbilical artery endothelial cells; HA, human astrocytes; HN, human neurons; HPNC, human perineurial cells; HCoEpiC, human colonic epithelial cells) showed CXCR5 surface expression by anti-CXCR5 immunostaining and flow cytometry analysis.(C) Quantitative determination of CXCR5 density per cell on selected B-NHL cell lines (SU-DHL4, OCI-Ly7, DOHH-2, SC-1, JeKo-1, MEC-1, JVM-3), on the MM cell line (NCI-H929), on B- (REH, NALM-6) and T-ALL (Jurkat) cell lines, on the colon adenocarcionoma cell line (SW-620), and the non- or CXCR5-transfected embryonic kidney cell line (HEK293, HEK-CXCR5, respectively) was performed by employing QuantiBRITE PE calibration beads and a CXCR5-specific antibody.
Figure 10:
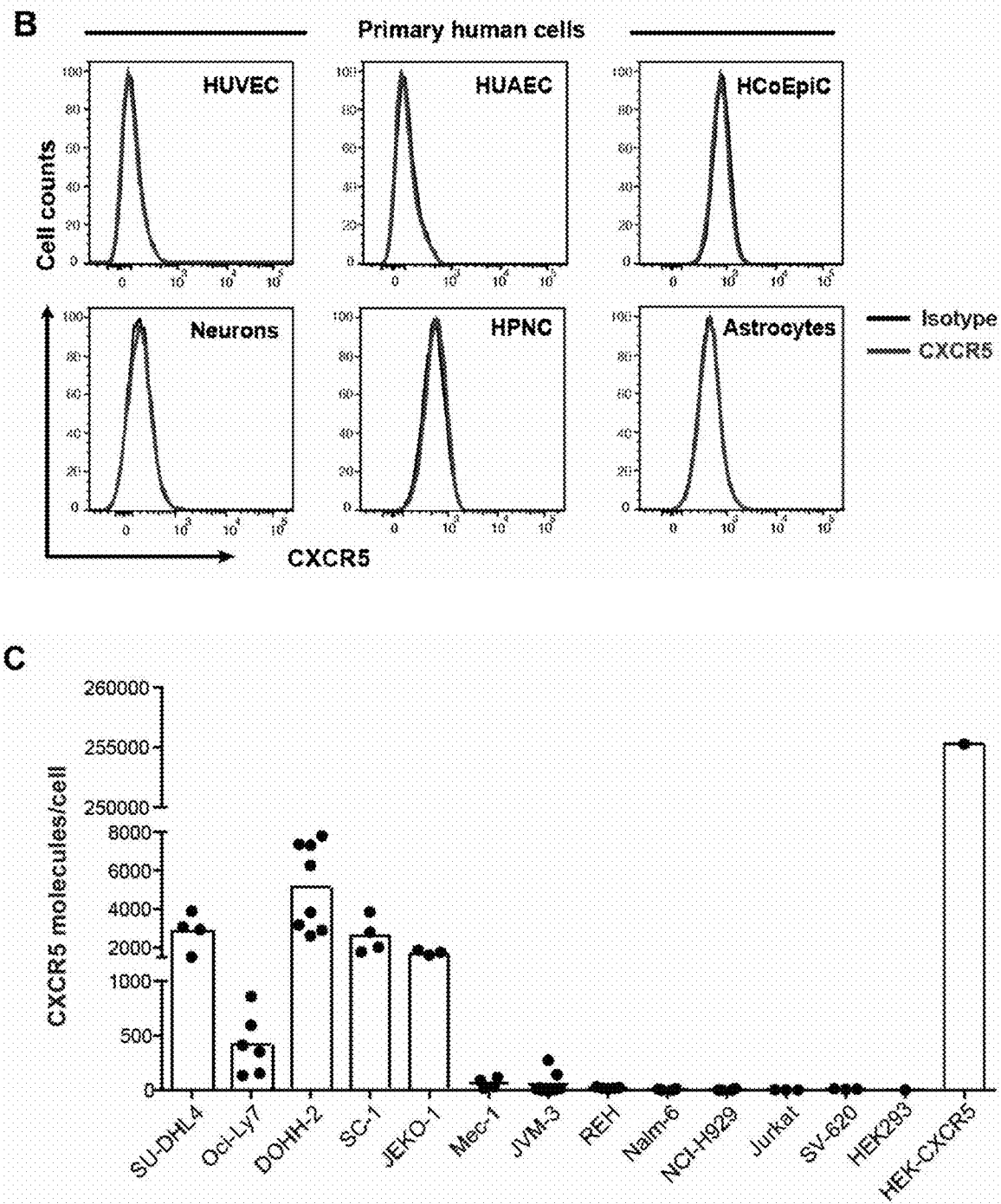
Figure 15:
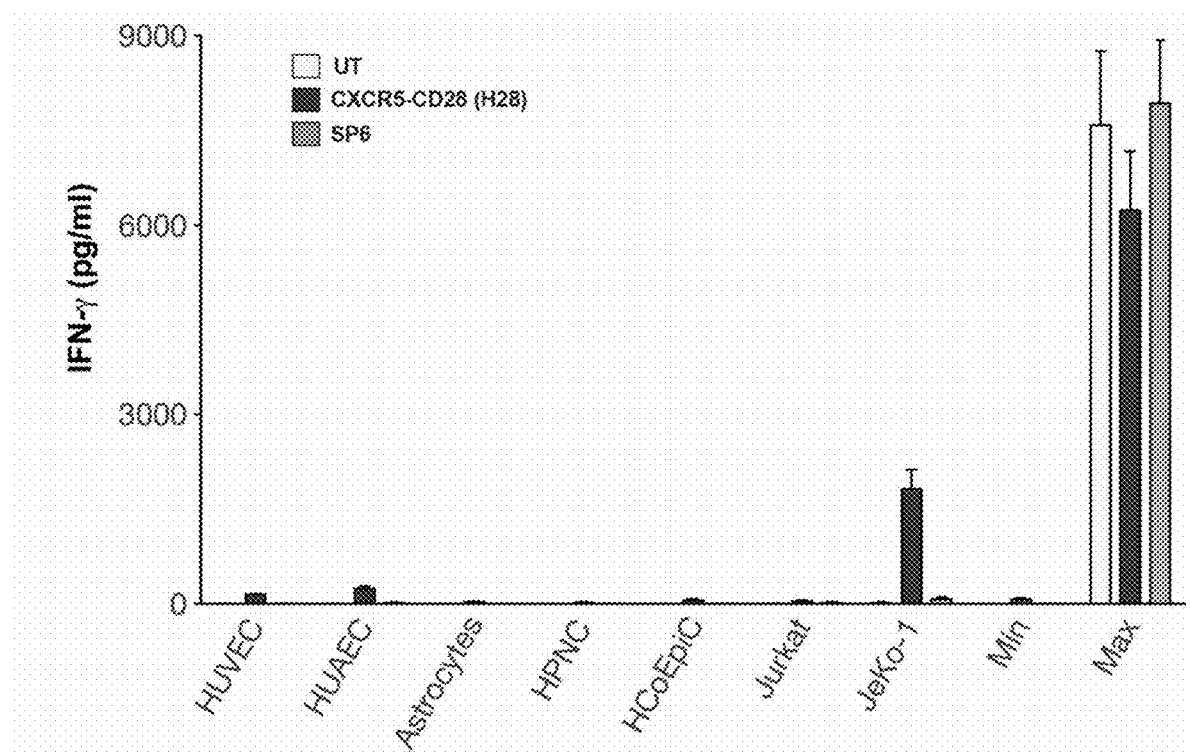
FIG. 15: Co-cultures of CAR-transduced human T cells with CXCR5-negative primary cells of different human tissues as targets show no off-target T cell activation, whereas the CXCR5-expressing B-NHL cell line JeKo-1 mediates specific T cell activation and serves as a positive control. Functional in vitro co-cultivation and IFN-gamma ELISA was performed. Untransduced (UT, open bars), CXCR5-CD28 CAR (H28, red bars) expressing T cells and SP6 CAR T cells (SP6, grey bars) were co-cultured with the primary cells HUVECs, HUAECs, HAs, HNs, HPNCs, HCoEpiCs; with the T-ALL cell line Jurkat, and the B-NHL cell line JeKo-1. Lack of IFN-gamma release is indicative of an absent specific T cell activation in the presence of CXCR5-negative primary cells, and the CXCR5-negative T-ALL cell line Jurkat. CXCR5-CD28 CAR-T cells of the present invention show specific IFN-gamma release in response to co-cultivation with CXCR5-expressing JeKo-1 target cells.

While the CXCR5-CD28 (H28) CAR appears to be the most effective, the two alternative CARs, CXCR5-4-1BB (HBB1) and CXCR5-CD28/4-1BB (H28BB), also show distinct specific activity. FIG. 15 shows that primary cells from healthy human tissues that do not carry CXCR5 (also refer data in FIG. 10B) do not induce specific activity of CXCR5-CD28 CAR-T cells.

Example 5: Clinical Approaches in Particular Patient Collectives

In the human setting in vivo, the invention is expected to show efficacy in B-NHL patients with diffuse large B-cell lymphoma, follicular lymphoma, chronic lymphocytic leukemia, and mantle cell lymphoma. Patients with the following characteristics are to be enrolled in a clinical phase I study: i) patients with multidrug resistances, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared and multiple lines of other standard of care therapies have failed, vi) patients with rapid progressive disease after autologous stem cell transplantation, vii) patients with progressive disease after allogeneic stem cell transplantation, viii) as a bridging therapy before allogeneic stem cell transplantation, and/or ix) patients exhibiting escape variants or mutants of CD19 and/or CD20 on tumor cells, such that current antibody therapies (anti CD20, Rituximab, anti CD19, Oletuzumab, BITE CD19/CD3, Blimatumomab) or anti-CD19 CAR therapies have lost/downregulated their target structures and become ineffective.

In the human setting in vivo, the invention is expected to show efficacy in T-NHL patients with angioimmunoblastic T-cell lymphoma, and various forms of T-cell lymphoma with leukemic dissemination, skin localization or any other organ dissemination. For these patients, selective treatments do not exist, except for generalized chemotherapy regimens. Therefore, patients with following characteristics are to be enrolled in a clinical phase I study: i) patients with multidrug resistances, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared and one or two lines of other standard of care therapies have failed, vi) patients with rapid progressive disease after autologous stem cell transplantation, vii) patients with progressive disease after allogeneic stem cell transplantation, viii) as a bridging therapy before allogeneic stem cell transplantation, ix) as second line therapy for patients with progressive disease upon one line of standard chemotherapy.

The invention claimed is:

1. A chimeric antigen receptor polypeptide (CAR), comprising:
   i. an extracellular antigen-binding domain, comprising an antibody or antibody fragment that binds CXC chemokine receptor type 5 (CXCR5) protein,
   ii. a transmembrane domain, and
   iii. an intracellular domain,
   wherein the antigen-binding domain comprises:
      a variable heavy chain (VH), said VH comprising complementary determining region (CDR) sequences of SEQ ID NO. 1, SEQ ID NO. 2 and SEQ ID NO. 3, and
      a variable light chain (VL), said VL comprising CDR sequences of SEQ ID NO. 4, SEQ ID NO 5, and SEQ ID NO. 6.

2. A chimeric antigen receptor (CAR) polypeptide according to claim 1, comprising a VH domain according to SEQ ID NO. 7:
EVQLVESGGGLVQPGX1SLX2LSCX3ASGFTFSTSG-MX4WFRQAPGKGLX5WVX6YISSSSGFVYADX-7VKGRFTISRDNAQNX8LYLQX9NSLX10X11E-DTAX1 2YYCARSEAAFWGQGTLVTVSS, wherein X1:G or K, X2:R or K; X3:A or S; X4:N or H; X5:E or D; X6:S or A; X7:S or A; X8:S or T; X9:M or L; X10:R or K, X11:A or S; X12:V or I;

and a VL domain according to SEQ ID NO. 8:
DIVLTQX1PRSX2PVTPGEX3ASISCRSX4KSRLSR-MGITPLNWYLQKPGX5SPQLLIYRMSNX6ASGV-PDRFSGSGSX7TDFTLKISKVETEDVGVYYCAQ-FLEYPP TFGSGTKLEIK, wherein X1:S or A; X2:L or V; X3:P or S; X4:S or N; X5:Q or K; X6:R or L; X7:G or E.

3. A chimeric antigen receptor (CAR) polypeptide according to claim 1, comprising
a VH domain according to: SEQ ID NO. 9, or SEQ ID NO. 10; and
a VL domain according to SEQ ID NO. 11, or SEQ ID NO. 12.

4. A chimeric antigen receptor (CAR) polypeptide according to claim 1, wherein when said CAR is expressed in a genetically modified immune cell, said immune cell binds CXCR5 on the surface of a CXCR5-expressing cell and is activated, thereby inducing cytotoxic activity against said CXCR5-expressing cell.

5. A chimeric antigen receptor (CAR) polypeptide according to claim 1:
wherein the extracellular antigen-binding domain comprises a linker polypeptide positioned between the VH and VL domains; and/or
wherein the transmembrane domain is selected from the group consisting of a CD8α domain according to SEQ ID NO. 20 and a CD28 domain according to SEQ ID NO 21; and/or
wherein the intracellular domain comprises a co-stimulatory domain selected from the group consisting of a 4-1BB co-stimulatory domain according to SEQ ID NO. 22; a CD28 co-stimulatory domain according to SEQ ID NO. 23, and a co-stimulatory domain comprising both a 4-1BB according to SEQ ID NO. 22 and a CD28 co-stimulatory domain according to SEQ ID NO. 23 arranged adjacently; and/or
comprising additionally a signaling domain (activation domain), wherein said signaling domain is a CD3zeta (4-1BB or CD28) signaling domain according to SEQ ID NO. 24.

6. A chimeric antigen receptor (CAR) polypeptide according to claim 5, wherein the CAR additionally comprises a spacer polypeptide positioned between the extracellular antigen-binding domain and the transmembrane domain, wherein said spacer polypeptide is selected from the group consisting of:
(a) an IgG1 spacer according to (SEQ ID NO. 15,
(b) an IgG1Δ spacer according to (SEQ ID NO. 16,
(c) an IgG4 (Hi-CH2-CH3) spacer according to (SEQ ID NO. 17,
(d) an IgG4 (Hi-CH3) spacer according to (SEQ ID NO. 18,
(e) an IgG4 (Hi) spacer according to SEQ ID NO 19, and
(f) a spacer with at least 80% sequence identity to any one of SEQ ID NO. 15 to SEQ ID NO. 19.

7. A chimeric antigen receptor (CAR) polypeptide according to claim 1, comprising or consisting of a sequence according to any one of SEQ ID NO. 25, 26, 27, 28 or 29.

8. The chimeric antigen receptor (CAR) polypeptide according to claim 5, wherein said linker is selected from the group consisting of a Whitlow linker according to SEQ ID NO. 13 and a Gly-Ser linker according to SEQ ID NO. 14.

9. The chimeric antigen receptor (CAR) polypeptide according to claim 4, wherein the genetically modified immune cell in which said CAR is expressed is a T lymphocyte.

10. The chimeric antigen receptor (CAR) polypeptide according to claim 4, wherein the CXCR5-expressing cell is a DOHH-2, OCI-Ly7, SU-DHL4, JeKo-1, JVM-3, MEC-1 and/or SC-1 cell.

11. A nucleic acid molecule that encodes a chimeric antigen receptor (CAR) polypeptide according to claim 1.

12. An isolated nucleic acid molecule according to claim 11 in the form of a vector.

13. An isolated nucleic acid molecule according to claim 12, wherein said vector is a viral vector or a transposon vector.

14. The isolated nucleic acid molecule according to claim 12, wherein said vector is a sleeping beauty vector.

15. A genetically modified immune cell expressing a CAR according to claim 1.

16. A genetically modified immune cell according to claim 15, wherein the immune cell is selected from the group consisting of a T lymphocyte and an NK cell.

17. The genetically modified immune cell according to claim 16, wherein said T lymphocyte is a cytotoxic T lymphocyte.

18. A method of treating a medical disorder associated with the presence of pathogenic cells expressing CXCR5 comprising administering a genetically modified immune cell according to claim 15 to a subject.

19. The method according to claim 18, wherein the medical disorder is mature B cell non-Hodgkin's lymphoma (B-NHL).

20. The method according to claim 18, wherein the medical disorder is a T cell non-Hodgkin's lymphoma, with or without a leukemic tumor cell dissemination.

21. The method according to claim 18, wherein the medical disorder is:
a B cell-derived lymphoproliferative disorder, selected from the group consisting of acute lymphoblastic leukemia (B-ALL), chronic lymphatic leukemia (CLL), follicular lymphoma (FL), mantle cell lymphoma (MCL) and diffuse large B cell lymphoma (DLBCL); or
a T cell-derived lymphoproliferative disorder, selected from the group consisting of angioimmunoblastic T cell lymphoma, cutaneous T cell lymphoma and T cell lymphoma with a leukemic dissemination.

22. The method according to claim 18, wherein the medical disorder is an autoantibody-dependent autoimmune disease.

23. The method of treating a medical disorder associated with the presence of pathogenic cells expressing CXCR5 according to claim 18, wherein said pathogenic cells expressing CXCR5 are mature B cells and/or memory B cells, and/or pathogenic T cells and/or T follicular helper cells.

24. The method according to claim 22, wherein said autoantibody-dependent autoimmune disease is selected from the group consisting of systemic lupus erythematosus (SLE) and rheumatoid arthritis.

* * * * *

UNITED STATES PATENT AND TRADEMARK OFFICE
CERTIFICATE OF CORRECTION

PATENT NO. : 11,643,468 B2
APPLICATION NO. : 16/641181
DATED : May 9, 2023
INVENTOR(S) : Uta Höpken et al.

Page 1 of 3

It is certified that error appears in the above-identified patent and that said Letters Patent is hereby corrected as shown below:

On the Title Page

Column 1, Line 3 (Item (73) Assignee), delete "Hemlholtz" and insert -- Helmholtz --.

In the Drawings

Sheet 3 of 16 (Fig. 5), Line 2, delete "sapies" and insert -- sapiens --.

Sheet 4 of 16 (Fig. 6), Line 2, delete "sapies" and insert -- sapiens --.

In the Specification

Column 1, Line 64, delete "Bruton" and insert -- Bruton's --.

Column 2, Lines 54-55, delete "Oletuzumab" and insert -- Elotuzumab --.

Column 7, Line 6, delete "Dicksinson)." and insert -- Dickinson). --.

Column 8, Line 64, after "linker," insert -- or --.

Column 9, Line 60 (approx.), after "FWVLVVVGGVLACYSLLVTVAFIIFWV)," insert -- or --.

Column 31, Line 16-38, delete "MCL xenograft, the B-ALL cell lines NALM6, REH, the MM cell line NCI-H929, and the T-ALL cell line Jurkat. As can be seen from the analysis, CXCR5 was expressed on the B-NHLs DOHH-2, SU-DHL4, OCI-Ly7 and JeKo-1 cell lines. (B) To rule out that the CXCR5 CAR-T cells of the present invention show crossreactivity with healthy human tissues, CXCR5 expression was assessed on a panel of primary cells derived from human healthy tissues. None of the tested primary human cells (HUVEC, human umbilical vein endothelial cells; HUAEC, human umbilical artery endothelial cells; HA, human astrocytes; HN, human neurons; HPNC, human perineurial cells; HCoEpiC, human colonic epithelial cells) showed CXCR5 surface expression by Signed and Sealed this
Seventeenth Day of October, 2023

Katherine Kelly Vidal
*Director of the United States Patent and Trademark Office*

CERTIFICATE OF CORRECTION (continued)
U.S. Pat. No. 11,643,468 B2 anti-CXCR5 immunostaining and flow cytometry analysis.(C) Quantitative determination of CXCR5 density per cell on selected B-NHL cell lines (SU-DHL4, OCI-Ly7, DOHH-2, SC-1, JeKo-1, MEC-1, JVM-3), on the MM cell line (NCI-H929), on B- (REH, NALM-6) and T-ALL (Jurkat) cell lines, on the colon adenocarcinoma cell line (SW-620), and the non- or CXCR5-transfected embryonic kidney cell line (HEK293, HEK-CXCR5, respectively) was performed by employing QuantiBRITE PE calibration beads and a CXCR5-specific antibody." and insert the same on Column 31, Line 15 as a continuation of the same paragraph.

Column 31, Lines 29-30, delete "analysis.(C)" and insert -- analysis. (C) --.

Column 31, Line 33, delete "B- (REH," and insert -- B-(REH, --.

Column 31, Line 34, delete "adenocarcionoma" and insert -- adenocarcinoma --.

Column 31, Line 55, delete "postive" and insert -- positive --.

Column 31, Line 67, delete "Il2rg$^{tmlb}$" and insert -- Il2rg$^{tm1}$ --.

Column 32, Line 5, delete "xenotransplantated" and insert -- xenotransplanted --.

Column 34, Line 31, delete "{" and insert -- ( --.

Column 39, Line 65, delete "{" and insert -- ( --.

Column 39, Line 67, delete "{" and insert -- ( --.

Column 40, Line 2, delete "VN5" and insert -- V5 --.

Column 40, Line 58, delete "immune deficiency" and insert -- immunodeficiency --.

Column 44, Line 12, delete "pluriotent" and insert -- pluripotent --.

Column 44, Line 13, delete "cells)" and insert -- cells). --.

Column 48, Line 8, delete "{" and insert -- ( --.

Column 50, Line 42, delete "cutanous" and insert -- cutaneous --.

Column 50, Line 44, delete "vasculitidies," and insert -- vasculitides, --.

Column 50, Lines 45-46, delete "Hennoch" and insert -- Henoch --.

Column 50, Line 50, delete "ateritis," and insert -- arthritis, --.

Column 50, Line 51, delete "Dego's" and insert -- Degos --.

CERTIFICATE OF CORRECTION (continued)
U.S. Pat. No. 11,643,468 B2

Column 50, Line 51, delete "Eythema" and insert -- Erythema --.

Column 51, Lines 1-2, delete "Autoimmunthrombocytopenia," and insert -- Autoimmune thrombocytopenia, --.

Column 51, Line 2, delete "Autoimmunneutropenia," and insert -- Autoimmune neutropenia, --.

Column 51, Line 2, delete "Autoimmunhemolytic" and insert -- Autoimmune hemolytic --.

Column 51, Line 3, delete "Autoimmunlymphocytopenia," and insert -- Autoimmune lymphocytopenia, --.

Column 51, Line 5, delete "atropic" and insert -- atrophic --.

Column 53, Line 39, delete "Und" and insert -- and --.

Column 54, Line 3, delete "und" and insert -- and --.

Column 54, Line 9, delete "und" and insert -- and --.

Column 54, Line 53, delete "UT±" and insert -- UT= --.

Column 55, Line 45 (approx.), delete "UT±" and insert -- UT= --.

Column 55, Line 46 (approx.), delete "$^{51}$Cr" and insert -- $^{51}$Cr. --.

Column 56, Line 2, delete "Xenotransplantatlon" and insert -- Xenotransplantation --.

Column 56, Line 10 (approx.), delete "Il2rg$^{tm1}$Wjl/SzJ)." and insert -- Il2rg$^{tm1}$ Wjl/SzJ). --.

Column 56, Line 43, delete "Prkdc$^{scid}$Il2rg$^{tm1}$" and insert -- Prkdc$^{cid}$ Il2rg$^{tm1}$ --.

Column 58, Line 4, delete "Oletuzumab," and insert -- Elotuzumab, --.

Column 58, Line 4, delete "Blimatumomab)" and insert -- Blinatumomab) --.

In the Claims

Column 122, Line 64, Claim 2, delete "X1 2" and insert -- X12 --.

Column 123, Line 5, Claim 2, delete "PP T" and insert -- PPT --.

Column 124, Line 14 (approx.), Claim 13, after "nucleic" insert -- acid --.

SEQUENCE LISTING

```
<160> NUMBER OF SEQ ID NOS: 64

<210> SEQ ID NO 1
<211> LENGTH: 8
<212> TYPE: PRT
<213> ORGANISM: Artificial Sequence
<220> FEATURE:
<223> OTHER INFORMATION: antibody sequence

<400> SEQUENCE: 1

Gly Phe Thr Phe Ser Thr Ser Gly
1               5

<210> SEQ ID NO 2
<211> LENGTH: 8
<212> TYPE: PRT
<213> ORGANISM: Artificial Sequence
<220> FEATURE:
<223> OTHER INFORMATION: antibody sequence

<400> SEQUENCE: 2

Ile Ser Ser Ser Ser Gly Phe Val
1               5

<210> SEQ ID NO 3
<211> LENGTH: 7
<212> TYPE: PRT
<213> ORGANISM: Artificial Sequence
<220> FEATURE:
<223> OTHER INFORMATION: antibody sequence

<400> SEQUENCE: 3

Ala Arg Ser Glu Ala Ala Phe
1               5

<210> SEQ ID NO 4
<211> LENGTH: 11
<212> TYPE: PRT
<213> ORGANISM: Artificial Sequence
```

```
<220> FEATURE:
<223> OTHER INFORMATION: antibody sequence

<400> SEQUENCE: 4

Lys Ser Arg Leu Ser Arg Met Gly Ile Thr Pro
1               5                   10

<210> SEQ ID NO 5
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Arg Met Ser Xaa
1

<210> SEQ ID NO 6
<211> LENGTH: 9
<212> TYPE: PRT
<213> ORGANISM: Artificial Sequence
<220> FEATURE:
<223> OTHER INFORMATION: antibody sequence

<400> SEQUENCE: 6

Ala Gln Phe Leu Glu Tyr Pro Pro Thr
1               5

<210> SEQ ID NO 7
<211> LENGTH: 113
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
```

```
<222> LOCATION: (82)..(82)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid

<400> SEQUENCE: 7

Glu Val Gln Leu Val Glu Ser Gly Gly Gly Leu Val Gln Pro Gly Xaa
1               5                  10                  15

Ser Leu Xaa Leu Ser Cys Xaa Ala Ser Gly Phe Thr Phe Ser Thr Ser
            20                  25                  30

Gly Met Xaa Trp Phe Arg Gln Ala Pro Gly Lys Gly Leu Xaa Trp Val
        35                  40                  45

Xaa Tyr Ile Ser Ser Ser Ser Gly Phe Val Tyr Ala Asp Xaa Val Lys
    50                  55                  60

Gly Arg Phe Thr Ile Ser Arg Asp Asn Ala Gln Asn Xaa Leu Tyr Leu
65                  70                  75                  80

Gln Xaa Asn Ser Leu Xaa Xaa Glu Asp Thr Ala Xaa Tyr Tyr Cys Ala
                85                  90                  95

Arg Ser Glu Ala Ala Phe Trp Gly Gln Gly Thr Leu Val Thr Val Ser
            100                 105                 110

Ser

<210> SEQ ID NO 8
<211> LENGTH: 112
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 8

Asp Ile Val Leu Thr Gln Xaa Pro Arg Ser Xaa Pro Val Thr Pro Gly
1               5                  10                  15

Glu Xaa Ala Ser Ile Ser Cys Arg Ser Xaa Lys Ser Arg Leu Ser Arg
            20                  25                  30
```

Met Gly Ile Thr Pro Leu Asn Trp Tyr Leu Gln Lys Pro Gly Xaa Ser
            35                  40                  45

Pro Gln Leu Leu Ile Tyr Arg Met Ser Asn Xaa Ala Ser Gly Val Pro
 50                  55                  60

Asp Arg Phe Ser Gly Ser Gly Ser Xaa Thr Asp Phe Thr Leu Lys Ile
 65                  70                  75                  80

Ser Lys Val Glu Thr Glu Asp Val Gly Val Tyr Tyr Cys Ala Gln Phe
                 85                  90                  95

Leu Glu Tyr Pro Pro Thr Phe Gly Ser Gly Thr Lys Leu Glu Ile Lys
                100                 105                 110

<210> SEQ ID NO 9
<211> LENGTH: 113
<212> TYPE: PRT
<213> ORGANISM: Artificial Sequence
<220> FEATURE:
<223> OTHER INFORMATION: antibody sequence

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Ser
                 20                  25                  30

Gly Met Asn Trp Phe Arg Gln Ala Pro Gly Lys Gly Leu Glu Trp Val
            35                  40                  45

Ser Tyr Ile Ser Ser Ser Gly Phe Val Tyr Ala Asp Ser Val Lys
 50                  55                  60

Gly Arg Phe Thr Ile Ser Arg Asp Asn Ala Gln Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ser Glu Ala Ala Phe Trp Gly Gln Gly Thr Leu Val Thr Val Ser
                100                 105                 110

Ser

<210> SEQ ID NO 10
<211> LENGTH: 113
<212> TYPE: PRT
<213> ORGANISM: Artificial Sequence
<220> FEATURE:
<223> OTHER INFORMATION: antibody sequence

<400> SEQUENCE: 10

Glu Val Gln Leu Val Glu Ser Gly Gly Gly Leu Val Gln Pro Gly Lys
 1               5                  10                  15

Ser Leu Lys Leu Ser Cys Ser Ala Ser Gly Phe Thr Phe Ser Thr Ser
                 20                  25                  30

Gly Met His Trp Phe Arg Gln Ala Pro Gly Lys Gly Leu Asp Trp Val
            35                  40                  45

Ala Tyr Ile Ser Ser Ser Gly Phe Val Tyr Ala Asp Ala Val Lys
 50                  55                  60

Gly Arg Phe Thr Ile Ser Arg Asp Asn Ala Gln Asn Thr Leu Tyr Leu
 65                  70                  75                  80

Gln Leu Asn Ser Leu Lys Ser Glu Asp Thr Ala Ile Tyr Tyr Cys Ala
                 85                  90                  95

Arg Ser Glu Ala Ala Phe Trp Gly Gln Gly Thr Leu Val Thr Val Ser
                100                 105                 110

Ser

<210> SEQ ID NO 11
<211> LENGTH: 112
<212> TYPE: PRT
<213> ORGANISM: Artificial Sequence
<220> FEATURE:
<223> OTHER INFORMATION: antibody sequence

<400> SEQUENCE: 11

Asp Ile Val Leu Thr Gln Ser Pro Arg Ser Leu Pro Val Thr Pro Gly
1               5                   10                  15

Glu Pro Ala Ser Ile Ser Cys Arg Ser Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: antibody sequence

<400> SEQUENCE: 12

Asp Ile Val Leu Thr Gln Ala Pro Arg Ser Val Ser Val Thr Pro Gly
1               5                   10                  15

Glu Ser Ala Ser Ile Ser Cys Arg Ser Asn Lys Ser Arg Leu Ser Arg
            20                  25                  30

Met Gly Ile Thr Pro Leu Asn Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 13
<211> LENGTH: 18
<212> TYPE: PRT
<213> ORGANISM: Artificial Sequence
<220> FEATURE:
<223> OTHER INFORMATION: linker

<400> SEQUENCE: 13

Gly Ser Thr Ser Gly Ser Gly Lys Pro Gly Ser Gly Glu Gly Ser Thr
1               5                   10                  15

Lys Gly

```
<210> SEQ ID NO 14
<211> LENGTH: 17
<212> TYPE: PRT
<213> ORGANISM: Artificial Sequence
<220> FEATURE:
<223> OTHER INFORMATION: linker

<400> SEQUENCE: 14

Ser Ser Gly Gly Gly Gly Ser Gly Gly Gly Ser Gly Gly Gly Gly
1               5                   10                  15

Ser

<210> SEQ ID NO 15
<211> LENGTH: 237
<212> TYPE: PRT
<213> ORGANISM: Artificial Sequence
<220> FEATURE:
<223> OTHER INFORMATION: IgG1 spacer

<400> SEQUENCE: 15

Pro Ala Glu Pro Lys Ser Pro Asp Lys Thr His Thr Cys Pro Pro Cys
1               5                   10                  15

Pro Ala Pro Pro Val Ala Gly Pro Ser Val Phe Leu Phe Pro Pro Lys
                20                  25                  30

Pro Lys Asp Thr Leu Met Ile Ala Arg Thr Pro Glu Val Thr Cys Val
            35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 16
<211> LENGTH: 235
<212> TYPE: PRT
<213> ORGANISM: Artificial Sequence
<220> FEATURE:
<223> OTHER INFORMATION: IgG1 delta spacer
```

<400> SEQUENCE: 16

```
Pro Ala Glu Pro Lys Ser Pro Asp Lys Thr His Thr Cys Pro Pro Cys
1               5                   10                  15
Pro Ala Pro Pro Val Ala Gly Pro Ser Val Phe Leu Phe Pro Pro Lys
            20                  25                  30
Pro Lys Asp Thr Leu Met Ile Ala Arg Thr Pro Glu Val Thr Cys Val
        35                  40                  45
Val Val Asp Val Ser His Glu Asp Pro Glu Val Lys Phe Asn Trp Tyr
    50                  55                  60
Val Asp Gly Val Glu Val His Asn Ala Lys Thr Lys Pro Arg Glu Glu
65                  70                  75                  80
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Asp Glu Leu
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Ser Leu Ser Pro Gly Lys Lys
225                 230                 235
```

<210> SEQ ID NO 17
<211> LENGTH: 229
<212> TYPE: PRT
<213> ORGANISM: Artificial Sequence
<220> FEATURE:
<223> OTHER INFORMATION: IgG4 (HI-CH2-CH3) spacer

<400> SEQUENCE: 17

```
Glu Ser Lys Tyr Gly Pro Pro Cys Pro Pro Cys Pro Ala Pro Glu Phe
1               5                   10                  15
Glu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
```

```
                    115                 120                 125
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Lys
225

<210> SEQ ID NO 18
<211> LENGTH: 119
<212> TYPE: PRT
<213> ORGANISM: Artificial Sequence
<220> FEATURE:
<223> OTHER INFORMATION: IgG4 (HI-CH3) spacer

<400> SEQUENCE: 18

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
            115

<210> SEQ ID NO 19
<211> LENGTH: 12
<212> TYPE: PRT
<213> ORGANISM: Artificial Sequence
<220> FEATURE:
<223> OTHER INFORMATION: IgG4 (HI) spacer

<400> SEQUENCE: 19

Glu Ser Lys Tyr Gly Pro Pro Cys Pro Pro Cys Pro
1               5                   10

<210> SEQ ID NO 20
<211> LENGTH: 24
<212> TYPE: PRT
<213> ORGANISM: Artificial Sequence
<220> FEATURE:
<223> OTHER INFORMATION: transmembrane domain CD8 alpha

<400> SEQUENCE: 20
```

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 21
<211> LENGTH: 27
<212> TYPE: PRT
<213> ORGANISM: Artificial Sequence
<220> FEATURE:
<223> OTHER INFORMATION: transmembrane domain CD28

<400> SEQUENCE: 21

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 22
<211> LENGTH: 42
<212> TYPE: PRT
<213> ORGANISM: Artificial Sequence
<220> FEATURE:
<223> OTHER INFORMATION: Co-stimulatory domain 4-1BB

<400> SEQUENCE: 22

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 23
<211> LENGTH: 42
<212> TYPE: PRT
<213> ORGANISM: Artificial Sequence
<220> FEATURE:
<223> OTHER INFORMATION: Co-stimulatory domain CD28

<400> SEQUENCE: 23

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Leu
        35                  40
```

<210> SEQ ID NO 24
<211> LENGTH: 113
<212> TYPE: PRT
<213> ORGANISM: Artificial Sequence
<220> FEATURE:
<223> OTHER INFORMATION: Activation domain CD3 zeta (4-1BB) or (CD28)

<400> SEQUENCE: 24

```
Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45
```

```
Lys Pro Arg Lys Asn Pro Gln Glu Gly Leu Tyr Asn Glu Leu Gln
 50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
             100                 105                 110

Arg
```

```
<210> SEQ ID NO 25
<211> LENGTH: 682
<212> TYPE: PRT
<213> ORGANISM: Artificial Sequence
<220> FEATURE:
<223> OTHER INFORMATION: H28

<400> SEQUENCE: 25
```

```
Met Asp Phe Gln Val Gln Ile Phe Ser Phe Leu Leu Ile Ser Ala Ser
 1               5                   10                  15

Val Ile Met Ser Arg Glu Val Gln Leu Val Glu Ser Gly Gly Gly Leu
             20                  25                  30

Val Gln Pro Gly Gly Ser Leu Arg Leu Ser Cys Ala Ala Ser Gly Phe
         35                  40                  45

Thr Phe Ser Thr Ser Gly Met Asn Trp Phe Arg Gln Ala Pro Gly Lys
     50                  55                  60

Gly Leu Glu Trp Val Ser Tyr Ile Ser Ser Ser Ser Gly Phe Val Tyr
 65                  70                  75                  80

Ala Asp Ser Val Lys Gly Arg Phe Thr Ile Ser Arg Asp Asn Ala Gln
                 85                  90                  95

Asn Ser Leu Tyr Leu Gln Met Asn Ser Leu Arg Ala Glu Asp Thr Ala
             100                 105                 110

Val Tyr Tyr Cys Ala Arg Ser Glu Ala Ala Phe Trp Gly Gln Gly Thr
         115                 120                 125

Leu Val Thr Val Ser Ser Gly Thr Ser Gly Ser Gly Lys Pro Gly Ser
     130                 135                 140

Gly Glu Gly Ser Thr Lys Gly Asp Ile Val Leu Thr Gln Ser Pro Arg
145                 150                 155                 160

Ser Leu Pro Val Thr Pro Gly Glu Pro Ala Ser Ile Ser Cys Arg Ser
                 165                 170                 175

Ser Lys Ser Arg Leu Ser Arg Met Gly Ile Thr Pro Leu Asn Trp Tyr
             180                 185                 190

Leu Gln Lys Pro Gly Gln Ser Pro Gln Leu Leu Ile Tyr Arg Met Ser
         195                 200                 205

Asn Arg Ala Ser Gly Val Pro Asp Arg Phe Ser Gly Ser Gly Ser Gly
     210                 215                 220

Thr Asp Phe Thr Leu Lys Ile Ser Lys Val Glu Thr Glu Asp Val Gly
225                 230                 235                 240

Val Tyr Tyr Cys Ala Gln Phe Leu Glu Tyr Pro Pro Thr Phe Gly Ser
                 245                 250                 255

Gly Thr Lys Leu Glu Ile Lys Pro Ala Glu Pro Lys Ser Pro Asp Lys
             260                 265                 270

Thr His Thr Cys Pro Pro Cys Pro Ala Pro Pro Val Ala Gly Pro
         275                 280                 285
```

Ser Val Phe Leu Phe Pro Pro Lys Pro Lys Asp Thr Leu Met Ile Ala
        290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
            325                 330                 335

Ala Lys Thr Lys Pro Arg Glu Glu Gln Tyr Asn Ser Thr Tyr Arg Val
        340                 345                 350

Val Ser Val Leu Thr Val Leu His Gln Asp Trp Leu Asn Gly Lys Glu
    355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
            405                 410                 415

Cys Leu Val Lys Gly Phe Tyr Pro Ser Asp Ile Ala Val Glu Trp Glu
        420                 425                 430

Ser Asn Gly Gln Pro Glu Asn Asn Tyr Lys Thr Thr Pro Pro Val Leu
    435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
            485                 490                 495

Lys Lys Asp Pro Lys Phe Trp Val Leu Val Val Val Gly Gly Val Leu
        500                 505                 510

Ala Cys Tyr Ser Leu Leu Val Thr Val Ala Phe Ile Ile Phe Trp Val
    515                 520                 525

Arg Ser Lys Arg Ser Arg Leu Leu His Ser Asp Tyr Met Asn Met Thr
530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Leu Arg Val Lys Phe Ser Arg
            565                 570                 575

Ser Ala Asp Ala Pro Ala Tyr Gln Gln Gly Gln Asn Gln Leu Tyr Asn
        580                 585                 590

Glu Leu Asn Leu Gly Arg Arg Glu Glu Tyr Asp Val Leu Asp Lys Arg
    595                 600                 605

Arg Gly Arg Asp Pro Glu Met Gly Gly Lys Pro Arg Arg Lys Asn Pro
610                 615                 620

Gln Glu Gly Leu Tyr Asn Glu Leu Gln Lys Asp Lys Met Ala Glu Ala
625                 630                 635                 640

Tyr Ser Glu Ile Gly Met Lys Gly Glu Arg Arg Arg Gly Lys Gly His
            645                 650                 655

Asp Gly Leu Tyr Gln Gly Leu Ser Thr Ala Thr Lys Asp Thr Tyr Asp
        660                 665                 670

Ala Leu His Met Gln Ala Leu Pro Pro Arg
    675                 680

<210> SEQ ID NO 26
<211> LENGTH: 682
<212> TYPE: PRT

<213> ORGANISM: Artificial Sequence
<220> FEATURE:
<223> OTHER INFORMATION: R28

<400> SEQUENCE: 26

```
Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Lys Ser Leu Lys Leu Ser Cys Ser Ala Ser Gly Phe
        35                  40                  45

Thr Phe Ser Thr Ser Gly Met His Trp Phe Arg Gln Ala Pro Gly Lys
    50                  55                  60

Gly Leu Asp Trp Val Ala Tyr Ile Ser Ser Ser Gly Phe Val Tyr
65                  70                  75                  80

Ala Asp Ala Val Lys Gly Arg Phe Thr Ile Ser Arg Asp Asn Ala Gln
                85                  90                  95

Asn Thr Leu Tyr Leu Gln Leu Asn Ser Leu Lys Ser Glu Asp Thr Ala
            100                 105                 110

Ile Tyr Tyr Cys Ala Arg Ser Glu Ala Ala Phe Trp Gly Gln Gly Thr
        115                 120                 125

Leu Val Thr Val Ser Ser Gly Ser Thr Ser Gly Ser Gly Lys Pro Gly
    130                 135                 140

Ser Gly Glu Gly Ser Thr Lys Gly Asp Ile Val Leu Thr Gln Ala Pro
145                 150                 155                 160

Arg Ser Val Ser Val Thr Pro Gly Glu Ser Ala Ser Ile Ser Cys Arg
                165                 170                 175

Ser Asn Lys Ser Arg Leu Ser Arg Met Gly Ile Thr Pro Leu Asn Trp
            180                 185                 190

Tyr Leu Gln Lys Pro Gly Lys Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Glu Thr Asp Phe Thr Leu Lys Ile Ser Lys Val Glu Thr Glu Asp Val
225                 230                 235                 240

Gly Val Tyr Tyr Cys Ala Gln Phe Leu Glu Tyr Pro Pro Thr Phe Gly
                245                 250                 255

Ser Gly Thr Lys Leu Glu Ile Lys Pro Ala Glu Pro Lys Ser Pro Asp
            260                 265                 270

Lys Thr His Thr Cys Pro Pro Cys Pro Ala Pro Val Ala Gly Pro
        275                 280                 285

Ser Val Phe Leu Phe Pro Pro Lys Pro Lys Asp Thr Leu Met Ile Ala
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
```

```
            385                 390                 395                 400
Leu Pro Pro Ser Arg Asp Glu Leu Thr Lys Asn Gln Val Ser Leu Thr
                    405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
        450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
            500                 505                 510

Ala Cys Tyr Ser Leu Leu Val Thr Val Ala Phe Ile Ile Phe Trp Val
        515                 520                 525

Arg Ser Lys Arg Ser Arg Leu Leu His Ser Asp Tyr Met Asn Met Thr
530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Leu Arg Val Lys Phe Ser Arg
                565                 570                 575

Ser Ala Asp Ala Pro Ala Tyr Gln Gln Gly Gln Asn Gln Leu Tyr Asn
            580                 585                 590

Glu Leu Asn Leu Gly Arg Arg Glu Glu Tyr Asp Val Leu Asp Lys Arg
        595                 600                 605

Arg Gly Arg Asp Pro Glu Met Gly Gly Lys Pro Arg Arg Lys Asn Pro
    610                 615                 620

Gln Glu Gly Leu Tyr Asn Glu Leu Gln Lys Asp Lys Met Ala Glu Ala
625                 630                 635                 640

Tyr Ser Glu Ile Gly Met Lys Gly Glu Arg Arg Arg Gly Lys Gly His
                645                 650                 655

Asp Gly Leu Tyr Gln Gly Leu Ser Thr Ala Thr Lys Asp Thr Tyr Asp
            660                 665                 670

Ala Leu His Met Gln Ala Leu Pro Pro Arg
        675                 680

<210> SEQ ID NO 27
<211> LENGTH: 678
<212> TYPE: PRT
<213> ORGANISM: Artificial Sequence
<220> FEATURE:
<223> OTHER INFORMATION: HBB1

<400> SEQUENCE: 27

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Thr Ser Gly Met Asn Trp Phe Arg Gln Ala Pro Gly Lys
        50                  55                  60

Gly Leu Glu Trp Val Ser Tyr Ile Ser Ser Ser Ser Gly Phe Val Tyr
```

```
                65                  70                  75                  80
Ala Asp Ser Val Lys Gly Arg Phe Thr Ile Ser Arg Asp Asn Ala Gln
                    85                  90                  95
Asn Ser Leu Tyr Leu Gln Met Asn Ser Leu Arg Ala Glu Asp Thr Ala
                    100                 105                 110
Val Tyr Tyr Cys Ala Arg Ser Glu Ala Ala Phe Trp Gly Gln Gly Thr
                    115                 120                 125
Leu Val Thr Val Ser Ser Gly Ser Thr Ser Gly Ser Gly Lys Pro Gly
                    130                 135                 140
Ser Gly Glu Gly Ser Thr Lys Gly Asp Ile Val Leu Thr Gln Ser Pro
145                 150                 155                 160
Arg Ser Leu Pro Val Thr Pro Gly Glu Pro Ala Ser Ile Ser Cys Arg
                    165                 170                 175
Ser Ser Lys Ser Arg Leu Ser Arg Met Gly Ile Thr Pro Leu Asn Trp
                    180                 185                 190
Tyr Leu Gln Lys Pro Gly Gln Ser Pro Gln Leu Leu Ile Tyr Arg Met
                    195                 200                 205
Ser Asn Arg Ala Ser Gly Val Pro Asp Arg Phe Ser Gly Ser Gly Ser
                    210                 215                 220
Gly Thr Asp Phe Thr Leu Lys Ile Ser Lys Val Glu Thr Glu Asp Val
225                 230                 235                 240
Gly Val Tyr Tyr Cys Ala Gln Phe Leu Glu Tyr Pro Pro Thr Phe Gly
                    245                 250                 255
Ser Gly Thr Lys Leu Glu Ile Lys Pro Ala Glu Pro Lys Ser Pro Asp
                    260                 265                 270
Lys Thr His Thr Cys Pro Pro Cys Pro Ala Pro Pro Val Ala Gly Pro
                    275                 280                 285
Ser Val Phe Leu Phe Pro Pro Lys Pro Lys Asp Thr Leu Met Ile Ala
                    290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                    325                 330                 335
Ala Lys Thr Lys Pro Arg Glu Glu Gln Tyr Asn Ser Thr Tyr Arg Val
                    340                 345                 350
Val Ser Val Leu Thr Val Leu His Gln Asp Trp Leu Asn Gly Lys Glu
                    355                 360                 365
Tyr Lys Cys Lys Val Ser Asn Lys Ala Leu Pro Ala Pro Ile Glu Lys
                    370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                    405                 410                 415
Cys Leu Val Lys Gly Phe Tyr Pro Ser Asp Ile Ala Val Glu Trp Glu
                    420                 425                 430
Ser Asn Gly Gln Pro Glu Asn Asn Tyr Lys Thr Thr Pro Pro Val Leu
                    435                 440                 445
Asp Ser Asp Gly Ser Phe Phe Leu Tyr Ser Lys Leu Thr Val Asp Lys
                    450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro
                    485                 490                 495
```

-continued

Gly Lys Lys Ile Tyr Ile Trp Ala Pro Leu Ala Gly Thr Cys Gly Val
            500                 505                 510

Leu Leu Leu Ser Leu Val Ile Thr Leu Tyr Cys Lys Arg Gly Arg Lys
        515                 520                 525

Lys Leu Leu Tyr Ile Phe Lys Gln Pro Phe Met Arg Pro Val Gln Thr
    530                 535                 540

Thr Gln Glu Glu Asp Gly Cys Ser Cys Arg Phe Pro Glu Glu Glu
545                 550                 555                 560

Gly Gly Cys Glu Leu Leu Arg Val Lys Phe Ser Arg Ser Ala Asp Ala
                565                 570                 575

Pro Ala Tyr Gln Gln Gly Gln Asn Gln Leu Tyr Asn Glu Leu Asn Leu
            580                 585                 590

Gly Arg Arg Glu Glu Tyr Asp Val Leu Asp Lys Arg Arg Gly Arg Asp
        595                 600                 605

Pro Glu Met Gly Gly Lys Pro Arg Arg Lys Asn Pro Gln Glu Gly Leu
    610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
            660                 665                 670

Gln Ala Leu Pro Pro Arg
            675

<210> SEQ ID NO 28
<211> LENGTH: 683
<212> TYPE: PRT
<213> ORGANISM: Artificial Sequence
<220> FEATURE:
<223> OTHER INFORMATION: HBB2

<400> SEQUENCE: 28

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Thr Ser Gly Met Asn Trp Phe Arg Gln Ala Pro Gly Lys
    50                  55                  60

Gly Leu Glu Trp Val Ser Tyr Ile Ser Ser Ser Gly Phe Val Tyr
65                  70                  75                  80

Ala Asp Ser Val Lys Gly Arg Phe Thr Ile Ser Arg Asp Asn Ala Gln
                85                  90                  95

Asn Ser Leu Tyr Leu Gln Met Asn Ser Leu Arg Ala Glu Asp Thr Ala
            100                 105                 110

Val Tyr Tyr Cys Ala Arg Ser Glu Ala Ala Phe Trp Gly Gln Gly Thr
        115                 120                 125

Leu Val Thr Val Ser Ser Gly Thr Ser Gly Ser Gly Lys Pro Gly
    130                 135                 140

Ser Gly Glu Gly Ser Thr Lys Gly Asp Ile Val Leu Thr Gln Ser Pro
145                 150                 155                 160

Arg Ser Leu Pro Val Thr Pro Gly Glu Pro Ala Ser Ile Ser Cys Arg
                165                 170                 175

```
Ser Ser Lys Ser Arg Leu Ser Arg Met Gly Ile Thr Pro Leu Asn Trp
            180                 185                 190

Tyr Leu Gln Lys Pro Gly Gln Ser Pro Gln Leu Leu Ile Tyr Arg Met
            195                 200                 205

Ser Asn Arg Ala Ser Gly Val Pro Asp Arg Phe Ser Gly Ser Gly Ser
210                 215                 220

Gly Thr Asp Phe Thr Leu Lys Ile Ser Lys Val Glu Thr Glu Asp Val
225                 230                 235                 240

Gly Val Tyr Tyr Cys Ala Gln Phe Leu Glu Tyr Pro Pro Thr Phe Gly
                245                 250                 255

Ser Gly Thr Lys Leu Glu Ile Lys Pro Ala Glu Pro Lys Ser Pro Asp
            260                 265                 270

Lys Thr His Thr Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ala
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
            500                 505                 510

Ala Cys Tyr Ser Leu Leu Val Thr Val Ala Phe Ile Ile Phe Trp Val
            515                 520                 525

Lys Arg Gly Arg Lys Lys Leu Leu Tyr Ile Phe Lys Gln Pro Phe Met
            530                 535                 540

Arg Pro Val Gln Thr Thr Gln Glu Glu Asp Gly Cys Ser Cys Arg Phe
545                 550                 555                 560

Pro Glu Glu Glu Glu Gly Gly Cys Glu Leu Arg Val Lys Phe Ser
                565                 570                 575

Arg Ser Ala Asp Ala Pro Ala Tyr Gln Gln Gly Gln Asn Gln Leu Tyr
            580                 585                 590
```

```
Asn Glu Leu Asn Leu Gly Arg Arg Glu Glu Tyr Asp Val Leu Asp Lys
            595                 600                 605

Arg Arg Gly Arg Asp Pro Glu Met Gly Gly Lys Pro Arg Arg Lys Asn
610                 615                 620

Pro Gln Glu Gly Leu Tyr Asn Glu Leu Gln Lys Asp Lys Met Ala Glu
625                 630                 635                 640

Ala Tyr Ser Glu Ile Gly Met Lys Gly Glu Arg Arg Arg Gly Lys Gly
            645                 650                 655

His Asp Gly Leu Tyr Gln Gly Leu Ser Thr Ala Thr Lys Asp Thr Tyr
            660                 665                 670

Asp Ala Leu His Met Gln Ala Leu Pro Pro Arg
            675                 680

<210> SEQ ID NO 29
<211> LENGTH: 724
<212> TYPE: PRT
<213> ORGANISM: Artificial Sequence
<220> FEATURE:
<223> OTHER INFORMATION: H28BB

<400> SEQUENCE: 29

Met Asp Phe Gln Val Gln Ile Phe Ser Phe Leu Leu Ile Ser Ala Ser
1               5                   10                  15

Val Ile Met Ser Arg Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Thr Ser Gly Met Asn Trp Phe Arg Gln Ala Pro Gly Lys
50                  55                  60

Gly Leu Glu Trp Val Ser Tyr Ile Ser Ser Ser Gly Phe Val Tyr
65                  70                  75                  80

Ala Asp Ser Val Lys Gly Arg Phe Thr Ile Ser Arg Asp Asn Ala Gln
                85                  90                  95

Asn Ser Leu Tyr Leu Gln Met Asn Ser Leu Arg Ala Glu Asp Thr Ala
            100                 105                 110

Val Tyr Tyr Cys Ala Arg Ser Glu Ala Ala Phe Trp Gly Gln Gly Thr
        115                 120                 125

Leu Val Thr Val Ser Ser Gly Ser Thr Ser Gly Ser Gly Lys Pro Gly
130                 135                 140

Ser Gly Glu Gly Ser Thr Lys Gly Asp Ile Val Leu Thr Gln Ser Pro
145                 150                 155                 160

Arg Ser Leu Pro Val Thr Pro Gly Glu Pro Ala Ser Ile Ser Cys Arg
                165                 170                 175

Ser Ser Lys Ser Arg Leu Ser Arg Met Gly Ile Thr Pro Leu Asn Trp
            180                 185                 190

Tyr Leu Gln Lys Pro Gly Gln Ser Pro Gln Leu Leu Ile Tyr Arg Met
        195                 200                 205

Ser Asn Arg Ala Ser Gly Val Pro Asp Arg Phe Ser Gly Ser Gly Ser
210                 215                 220

Gly Thr Asp Phe Thr Leu Lys Ile Ser Lys Val Glu Thr Glu Asp Val
225                 230                 235                 240

Gly Val Tyr Tyr Cys Ala Gln Phe Leu Glu Tyr Pro Thr Phe Gly
                245                 250                 255

Ser Gly Thr Lys Leu Glu Ile Lys Pro Ala Glu Pro Lys Ser Pro Asp
            260                 265                 270
```

-continued

```
Lys Thr His Thr Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ala
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
        450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
            500                 505                 510

Ala Cys Tyr Ser Leu Leu Val Thr Val Ala Phe Ile Ile Phe Trp Val
            515                 520                 525

Arg Ser Lys Arg Ser Arg Leu Leu His Ser Asp Tyr Met Asn Met Thr
530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Leu Lys Arg Gly Arg Lys Lys
                565                 570                 575

Leu Leu Tyr Ile Phe Lys Gln Pro Phe Met Arg Pro Val Gln Thr Thr
            580                 585                 590

Gln Glu Glu Asp Gly Cys Ser Cys Arg Phe Pro Glu Glu Glu Glu Gly
            595                 600                 605

Gly Cys Glu Leu Arg Val Lys Phe Ser Arg Ser Ala Asp Ala Pro Ala
        610                 615                 620

Tyr Gln Gln Gly Gln Asn Gln Leu Tyr Asn Glu Leu Asn Leu Gly Arg
625                 630                 635                 640

Arg Glu Glu Tyr Asp Val Leu Asp Lys Arg Arg Gly Arg Asp Pro Glu
                645                 650                 655

Met Gly Gly Lys Pro Arg Arg Lys Asn Pro Gln Glu Gly Leu Tyr Asn
            660                 665                 670

Glu Leu Gln Lys Asp Lys Met Ala Glu Ala Tyr Ser Glu Ile Gly Met
            675                 680                 685

Lys Gly Glu Arg Arg Arg Gly Lys Gly His Asp Gly Leu Tyr Gln Gly
```

```
                690                 695                 700
Leu Ser Thr Ala Thr Lys Asp Thr Tyr Asp Ala Leu His Met Gln Ala
705                 710                 715                 720

Leu Pro Pro Arg

<210> SEQ ID NO 30
<211> LENGTH: 21
<212> TYPE: PRT
<213> ORGANISM: Artificial Sequence
<220> FEATURE:
<223> OTHER INFORMATION: Lkappa Leader

<400> SEQUENCE: 30

Met Asp Phe Gln Val Gln Ile Phe Ser Phe Leu Leu Ile Ser Ala Ser
1               5                   10                  15

Val Ile Met Ser Arg
            20

<210> SEQ ID NO 31
<211> LENGTH: 2049
<212> TYPE: DNA
<213> ORGANISM: Artificial Sequence
<220> FEATURE:
<223> OTHER INFORMATION: H28d

<400> SEQUENCE: 31
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agcaccagcg catgaactg gttcagacag     180 gcccctggca agggcctgga atgggtgtcc tacatcagca gcagctccgg cttcgtgtac     240
gccgacagcg tgaagggccg gttcaccatc agcagagaca cgcccagaa cagcctgtac     300 ctgcagatga ctccctgcg ggccgaggac accgccgtgt actactgtgc agaagcgag     360 gccgcctttt ggggccaggg aacactcgtg acagtgtcca gcggcagcac aagcggctct     420
ggcaaacctg gatctggcga gggcagcacc aagggcgata cgtgctgac ccagagcccc     480 agatccctgc ctgtgacacc tggcgagcct gccagcatca gctgcagaag cagcaagagc     540
cggctgagcc ggatgggcat cacccccctg aactggtatc tgcagaaacc cggccagtcc     600
ccccagctgc tgatctaccg gatgagcaac agagccagcg gcgtgcccga tagattttcc     660
ggctctggaa gcggcaccga cttcaccctg aagatcagca aggtggaaac cgaggacgtg     720
ggcgtgtact attgcgccca gttcctggaa taccccccca cctttggcag cggcaccaag     780
ctggaaatca agcccgccga gcccaagagc ccgacaaga cccataccctg ccctccatgt     840 cctgcccctc cagtggctgg ccctagcgtg ttcctgttcc cccaaaagcc aaggacacc      900 ctgatgatcg cccggacccc tgaagtgacc tgcgtggtgg tggatgtgtc ccacgaggat     960
cccgaagtga agttcaattg gtacgtggac ggcgtggaag tgcacaacgc caagaccaag    1020
cccagagagg aacagtacaa cagcacctac cgggtggtgt ctgtgctgac cgtgctgcat    1080
caggactggc tgaacggcaa agagtacaag tgcaaggtgt ccaacaaggc cctgcctgcc    1140
cccatcgaga aaaccatctc caaggccaag ggacagcccc gcgagcccca ggtgtacaca    1200
ctgcctccaa gcagggacga gctgaccaag aaccaggtca gcctgacctg cctggtcaaa    1260
ggcttctatc ccagcgacat cgccgtggag tgggagagca tgggcagcc ggagaacaac     1320 tacaagacca cgcctcccgt gctggactcc gacggctcct tcttcctcta cagcaagctc    1380
```

```
accgtggaca agagcaggtg gcagcagggg aacgtcttct catgctccgt gatgcatgag    1440
gctctgcaca accactacac gcagaagagc ctctccctgt ctccgggtaa aaaagatccc    1500
aaattttggg tgctggtggt ggttggtgga gtcctggctt gctatagctt gctagtaaca    1560
gtggccttta ttattttctg ggtgaggagt aagaggagca ggctcctgca cagtgactac    1620
atgaacatga ctccccgccg ccccgggccc acccgcaagc attaccagcc ctatgcccca    1680
ccacgcgact tcgcagccta tcgctccctg agagtgaagt tcagcaggag cgcagacgcc    1740
cccgcgtacc agcagggcca gaaccagctc tataacgagc tcaatctagg acgaagagag    1800
gagtacgatg ttttggacaa gagacgtggc cgggaccctg agatgggggg aaagccgaga    1860
aggaagaacc ctcaggaagg cctgtacaat gaactgcaga agataagat ggcggaggcc     1920 tacagtgaga ttgggatgaa aggcgagcgc cggagggggca aggggcacga tggcctttac    1980
cagggtctca gtacagccac caaggacacc tacgacgccc ttcacatgca ggccctgccc    2040
cctcgctga                                                           2049
```

<210> SEQ ID NO 32
<211> LENGTH: 2049
<212> TYPE: DNA
<213> ORGANISM: Artificial Sequence
<220> FEATURE:
<223> OTHER INFORMATION: R28d

<400> SEQUENCE: 32

```
atggatttcc aggtgcagat cttcagcttc ctgctgatct ccgccagcgt gatcatgagc      60
cgcgaggtac agctggtgga gtctggagga ggcttagtgc agcctggaaa gtccctgaaa     120
ctctcctgtt cagcctctgg attcacattc agtacctctg gcatgcactg gtttcgccaa     180
gctccaggaa aggggctgga ttgggttgca tacattagta gtagcagcgg tttcgtctat     240
gcagacgctg tgaagggccg gttcaccatc tccagagaca atgcacagaa caccctgtac     300
ctgcaactca cagtctgaa gtctgaagac actgccatct attactgtgc aagaagcgag     360
gctgctttct ggggccaagg cactctggtc actgtctctt caggcagcac cagcggctcc     420
ggcaagcctg gctctggcga gggcagcaca aaggagatat ttgtgttgac tcaagctcca     480
cgctctgtat ctgtcactcc tggagagtca gcttccatct cctgcaggtc taataagagt     540
cgactgagta ggatgggcat cactcccttg aattggtacc ttcagaagcc aggaaagtct     600
cctcagctcc tgatatatcg gatgtccaac cttgcctcag gagttccaga caggtttagt     660
ggcagtgggt cagaaacaga ttttacactg aaaatcagta aggtggagac tgaggatgtt     720
ggcgtttatt actgtgcaca gtttctagaa tatcctccta cgttcggttc tgggaccaag     780
ctggagatca aacctgccga gcctaagagc cccgacaaga cccacacctg tccccccttgt   840 cctgcccctc cagtggctgg ccctagcgtg ttcctgttcc cccaaagcc aaggatacc       900 ctgatgatcg cccggacccc cgaagtcaca tgcgtggtgg tggacgtgag ccacgaagac     960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
caggactggc tgaatggcaa ggagtacaag tgcaaggtct ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc ccagcgacat cgccgtggag tgggagagca atgggcagcc ggagaacaac    1320
tacaagacca cgcctcccgt gctggactcc gacggctcct tcttcctcta cagcaagctc    1380
```

-continued

```
accgtggaca agagcaggtg gcagcagggg aacgtcttct catgctccgt gatgcatgag    1440
gctctgcaca accactacac gcagaagagc ctctccctgt ctccgggtaa aaaagatccc    1500
aaattttggg tgctggtggt ggttggtgga gtcctggctt gctatagctt gctagtaaca    1560
gtggccttta ttattttctg ggtgaggagt aagaggagca ggctcctgca cagtgactac    1620
atgaacatga ctccccgccg ccccgggccc acccgcaagc attaccagcc ctatgcccca    1680
ccacgcgact tcgcagccta tcgctccctg agagtgaagt tcagcaggag cgcagacgcc    1740
cccgcgtacc agcagggcca gaaccagctc tataacgagc tcaatctagg acgaagagag    1800
gagtacgatg ttttggacaa gagacgtggc cgggaccctg agatgggggg aaagccgaga    1860
aggaagaacc ctcaggaagg cctgtacaat gaactgcaga agataagat ggcggaggcc     1920 tacagtgaga ttgggatgaa aggcgagcgc ggaggggca aggggcacga tggcctttac     1980
cagggtctca gtacagccac caaggacacc tacgacgccc ttcacatgca ggccctgccc    2040
cctcgctga                                                             2049
```

<210> SEQ ID NO 33
<211> LENGTH: 2037
<212> TYPE: DNA
<213> ORGANISM: Artificial Sequence
<220> FEATURE:
<223> OTHER INFORMATION: HBB1d

<400> SEQUENCE: 33

```
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agcaccagcg gcatgaactg gttcagacag     180
gcccctggca agggcctgga atgggtgtcc tacatcagca gcagctccgg cttcgtgtac     240
gccgacagcg tgaagggccg gttcaccatc agcagagaca cgcccagaa cagcctgtac      300 ctgcagatga actccctgcg ggccgaggac accgccgtgt actactgtgc cagaagcgag    360
gccgcctttt ggggccaggg aacactcgtg acagtgtcca gcggcagcac aagcggctct    420
ggcaaacctg gatctggcga gggcagcacc aagggcgata tcgtgctgac ccagagcccc   480
agatccctgc ctgtgacacc tggcgagcct gccagcatca gctgcagaag cagcaagagc    540
cggctgagcc ggatgggcat acccccctg aactggtatc tgcagaaacc cggccagtcc     600
ccccagctgc tgatctaccg gatgagcaac agagccagcg gcgtgcccga tagattttcc    660
ggctctggaa gcggcaccga cttcaccctg aagatcagca aggtggaaac cgaggacgtg    720
ggcgtgtact attgcgccca gttcctggaa tacccccca ctttggcag cggcaccaag     780 ctggaaatca gcccgccga gcccaagagc ccgacaaga cccatcctg ccctccatgt      840 cctgccctc cagtggctgg ccctagcgtg ttcctgttcc cccaaagcc caaggacacc     900 ctgatgatcg cccggacccc tgaagtgacc tgcgtggtgg tggatgtgtc cacgaggat    960 cccgaagtga agttcaattg gtacgtggac ggcgtggaag tgcacaacgc caagaccaag   1020
cccagagagg aacagtacaa cagcacctac cgggtggtgt ctgtgctgac cgtgctgcat   1080
caggactggc tgaacggcaa agagtacaag tgcaaggtgt ccaacaaggc cctgcctgcc   1140
cccatcgaga aaaccatctc caaggccaag ggacagcccc gcgagcccca ggtgtacaca   1200
ctgcctccaa gcagggacga gctgaccaag aaccaggtgt ccctgacctg cctcgtgaag   1260
ggcttctacc cctccgatat cgccgtggaa tgggagagca atggccagcc cgagaacaac   1320
```

```
tacaagacca ccccccctgt gctggacagc gacggctcat tcttcctgta cagcaagctg    1380
acagtggaca agagccggtg gcagcagggc aacgtgttca gctgcagcgt gatgcacgag    1440
gctctgcaca accactacac ccagaagtcc ctgagcagcc tgagcccagg caagaagatc    1500
tacatctggg cccctctggc cggcacctgt ggcgtgctgc tgctgtctct cgtgatcaca    1560
ctgtactgca gcggggcag aaagaagctg ctgtacatct tcaagcagcc cttcatgcgg    1620
cccgtgcaga ccacccagga gaggacggc tgctcctgca gattcccga ggaagaagaa     1680 ggcggctgcg agctgctgcg cgtgaagttt tctagaagcg ccgacgcccc tgcctaccag    1740
cagggccaga accagctgta caacgagctg aacctgggca gacgggaaga gtacgacgtg    1800
ctggataagc ggagaggccg ggaccctgag atgggcggca gcctagaag aaagaacccc    1860 caggaaggcc tgtataacga actgcagaaa gacaagatgg ccgaggccta cagcgagatc    1920
ggaatgaagg gcgagcggag aagaggcaag ggccacgatg gactgtacca gggcctgagc    1980
accgccacca aggacaccta tgacgccctg cacatgcagg ctctgccccc cagataa       2037
```

<210> SEQ ID NO 34
<211> LENGTH: 2052
<212> TYPE: DNA
<213> ORGANISM: Artificial Sequence
<220> FEATURE:
<223> OTHER INFORMATION: HBB2d

<400> SEQUENCE: 34

```
atggatttcc aggtgcagat cttcagcttc ctgctgatct ccgccagcgt gatcatgagc      60
cgcgaggtgc agctggtgga atctggcgga ggactggtgc agcctggcgg ctctctgaga     120
ctgtcttgtg ccgccagcgg cttcaccttc agcaccagcg gcatgaactg gttcagacag     180
gcccctggca agggcctgga atgggtgtcc tacatcagca gcagctccgg cttcgtgtac     240
gccgacagcg tgaagggccg gttcaccatc agcagagaca cgcccagaa cagcctgtac     300 ctgcagatga ctcccctgcg ggccgaggac accgccgtgt actactgtgc cagaagcgag    360
gccgcctttt ggggccaggg aacactcgtg acagtgtcca gcggcagcac aagcggctct    420
ggcaaacctg gatctggcga gggcagcacc aagggcgata tcgtgctgac ccagagcccc    480
agatccctgc ctgtgacacc tggcgagcct gccagcatca gctgcagaag cagcaagagc    540
cggctgagcc ggatgggcat caccccctg aactggtatc tgcagaaacc cggccagtcc    600
ccccagctgc tgatctaccg gatgagcaac agagccagcg gcgtgcccga tagatttcc    660 ggctctggaa gcggcaccga cttcaccctg aagatcagca aggtgaaac cgaggacgtg    720 ggcgtgtact attgcgccca gttcctggaa taccccccca cctttggcag cggcaccaag    780
ctggaaatca gcccgccga gcccaagagc ccgacaaga cccataccctg ccctccatgt    840 cctgcccctc cagtggctgg ccctagcgtg ttcctgttcc cccaaagcc caaggacacc    900 ctgatgatcg cccggacccc tgaagtgacc tgcgtggtgg tggatgtgtc ccacgaggat    960
cccgaagtga agttcaattg gtacgtggac ggcgtggaag tgcacaacgc caagaccaag   1020
cccagagagg aacagtacaa cagcacctac cgggtggtgt ctgtgctgac cgtgctgcat   1080
caggactggc tgaacggcaa agagtacaag tgcaaggtgt ccaacaaggc cctgcctgcc   1140
cccatcgaga aaaccatctc caaggccaag ggacagcccc gcgagcccca ggtgtacaca   1200
ctgcctccaa gcagggacga gctgaccaag aaccaggtca gcctgacctg cctggtcaaa   1260
ggcttctatc ccagcgacat cgccgtggag tgggagagca atgggcagcc ggagaacaac   1320
tacaagacca cgcctcccgt gctggactcc gacggctcct tcttcctcta cagcaagctc   1380
```

| | |
|---|---|
| accgtggaca agagcaggtg gcagcagggg aacgtcttct catgctccgt gatgcatgag | 1440 |
| gctctgcaca accactacac gcagaagagc ctctccctgt ctccgggtaa aaaagatccc | 1500 |
| aaattttggg tgctggtggt ggttggtgga gtcctggctt gctatagctt gctagtaaca | 1560 |
| gtggccttta ttattttctg ggtgaagcgg ggcagaaaga agctgctgta catcttcaag | 1620 |
| cagcccttca tgcggcccgt gcagaccacc caggaagagg acggctgctc ctgcagattc | 1680 |
| cccgaggaag aagaaggcgg ctgcgagctg ctgagagtga agttcagcag gagcgcagac | 1740 |
| gcccccgcgt accagcaggg ccagaaccag ctctataacg agctcaatct aggacgaaga | 1800 |
| gaggagtacg atgttttgga caagagacgt ggccgggacc ctgagatggg gggaaagccg | 1860 |
| agaaggaaga accctcagga aggcctgtac aatgaactgc agaaagataa gatggcggag | 1920 |
| gcctacagtg agattgggat gaaaggcgag cgccggaggg gcaaggggca cgatggcctt | 1980 |
| taccagggtc tcagtacagc caccaaggac acctacgacg cccttcacat gcaggccctg | 2040 |
| ccccctcgct ga | 2052 |

```
<210> SEQ ID NO 35
<211> LENGTH: 2175
<212> TYPE: DNA
<213> ORGANISM: Artificial Sequence
<220> FEATURE:
<223> OTHER INFORMATION: H28BBd

<400> SEQUENCE: 35
```

| | |
|---|---|
| atggatttcc aggtgcagat cttcagcttc ctgctgatct ccgccagcgt gatcatgagc | 60 |
| cgcgaggtgc agctggtgga atctggcgga ggactggtgc agcctggcgg ctctctgaga | 120 |
| ctgtcttgtg ccgccagcgg cttcaccttc agcaccagcg gcatgaactg gttcagacag | 180 |
| gcccctggca agggcctgga atgggtgtcc tacatcagca gcagctccgg cttcgtgtac | 240 |
| gccgacagcg tgaagggccg gttcaccatc agcagagaca cgcccagaa cagcctgtac | 300 |
| ctgcagatga actccctgcg ggccgaggac accgccgtgt actactgtgc cagaagcgag | 360 |
| gccgcctttt ggggccaggg aacactcgtg acagtgtcca gcggcagcac aagcggctct | 420 |
| ggcaaacctg gatctggcga gggcagcacc aagggcgata tcgtgctgac ccagagcccc | 480 |
| agatccctgc ctgtgacacc tggcgagcct gccagcatca gctgcagaag cagcaagagc | 540 |
| cggctgagcc ggatgggcat cacccccctg aactggtatc tgcagaaacc cggccagtcc | 600 |
| ccccagctgc tgatctaccg gatgagcaac agagccagcg gcgtgcccga tagattttcc | 660 |
| ggctctggaa gcggcaccga cttcaccctg aagatcagca aggtggaaac cgaggacgtg | 720 |
| ggcgtgtact attgcgccca gttcctggaa taccccccca cctttggcag cggcaccaag | 780 |
| ctggaaatca gccccgccga gcccaagagc cccgacaaga cccatacctg ccctccatgt | 840 |
| cctgcccctc cagtggctgg ccctagcgtg ttcctgttcc cccaaagcc aaggacacc | 900 |
| ctgatgatcg cccggacccc tgaagtgacc tgcgtggtgg tggatgtgtc ccacgaggat | 960 |
| cccgaagtga agttcaattg gtacgtggac ggcgtggaag tgcacaacgc caagaccaag | 1020 |
| cccagagagg aacagtacaa cagcacctac cgggtggtgt ctgtgctgac cgtgctgcat | 1080 |
| caggactggc tgaacggcaa agagtacaag tgcaaggtgt ccaacaaggc cctgcctgcc | 1140 |
| cccatcgaga aaaccatctc caaggccaag ggacagcccc gcgagcccca ggtgtacaca | 1200 |
| ctgcctccaa gcagggacga gctgaccaag aaccaggtca gcctgacctg cctggtcaaa | 1260 |
| ggcttctatc ccagcgacat cgccgtggag tgggagagca atgggcagcc ggagaacaac | 1320 |

```
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctccgggtaa aaaagatccc    1500
aaattttggg tgctggtggt ggttggtgga gtcctggctt gctatagctt gctagtaaca    1560
gtggccttta ttattttctg ggtgaggagt aagaggagca ggctcctgca cagtgactac    1620
atgaacatga ctccccgccg ccccgggccc accgcaagc attaccagcc ctatgcccca    1680
ccacgcgact tcgcagccta tcgctccctg aagcggggca gaaagaagct gctgtacatc    1740
ttcaagcagc ccttcatgcg gcccgtgcag accacccagg aagaggacgg ctgctcctgc    1800
agattccccg aggaagaaga aggcggctgc gagctgagag tgaagttcag caggagcgca    1860 gacgccccg cgtaccagca gggccagaac cagctctata cgagctcaa tctaggacga    1920 agagaggagt acgatgtttt ggacaagaga cgtggccggg accctgagat ggggggaaag    1980
ccgagaagga agaaccctca ggaaggcctg tacaatgaac tgcagaaaga taagatggcg    2040
gaggcctaca gtgagattgg gatgaaaggc gagcgccgga ggggcaaggg gcacgatggc    2100
ctttaccagg gtctcagtac agccaccaag gacacctacg acgcccttca catgcaggcc    2160 ctgcccctc gctga                                                     2175

<210> SEQ ID NO 36
<211> LENGTH: 63
<212> TYPE: DNA
<213> ORGANISM: Artificial Sequence
<220> FEATURE:
<223> OTHER INFORMATION: Lkappa Leader d

<400> SEQUENCE: 36
atggatttcc aggtgcagat cttcagcttc ctgctgatct ccgccagcgt gatcatgagc    60
cgc                                                                 63

<210> SEQ ID NO 37
<211> LENGTH: 339
<212> TYPE: DNA
<213> ORGANISM: Artificial Sequence
<220> FEATURE:
<223> OTHER INFORMATION: Humanized VHd

<400> SEQUENCE: 37
gaggtgcagc tggtggaatc tggcggagga ctggtgcagc ctggcggctc tctgagactg    60
tcttgtgccg ccagcggctt caccttcagc accagcggca tgaactggtt cagacaggcc    120
cctggcaagg gcctggaatg ggtgtcctac atcagcagca gctccggctt cgtgtacgcc    180
gacagcgtga agggccggtt caccatcagc agagacaacg cccagaacag cctgtacctg    240
cagatgaact cctgcgggc cgaggacacc gccgtgtact actgtgccag aagcgaggcc    300
gccttttggg gccagggaac actcgtgaca gtgtccagc                          339

<210> SEQ ID NO 38
<211> LENGTH: 339
<212> TYPE: DNA
<213> ORGANISM: Artificial Sequence
<220> FEATURE:
<223> OTHER INFORMATION: Rat VHd

<400> SEQUENCE: 38
gaggtacagc tggtggagtc tggaggaggc ttagtgcagc ctggaaagtc cctgaaactc    60
tcctgttcag cctctggatt cacattcagt acctctggca tgcactggtt cgccaagct    120
```

```
ccaggaaagg ggctggattg ggttgcatac attagtagta gcagcggttt cgtctatgca      180
gacgctgtga agggccggtt caccatctcc agagacaatg cacagaacac cctgtacctg      240
caactcaaca gtctgaagtc tgaagacact gccatctatt actgtgcaag aagcgaggct      300
gctttctggg gccaaggcac tctggtcact gtctcttca                             339

<210> SEQ ID NO 39
<211> LENGTH: 336
<212> TYPE: DNA
<213> ORGANISM: Artificial Sequence
<220> FEATURE:
<223> OTHER INFORMATION: Humanized VLd

<400> SEQUENCE: 39
gatatcgtgc tgacccagag ccccagatcc ctgcctgtga cacctggcga gcctgccagc       60
atcagctgca gaagcagcaa gagccggctg agccggatgg gcatcacccc cctgaactgg      120
tatctgcaga acccggcca gtccccccag ctgctgatct accggatgag caacagagcc       180
agcggcgtgc ccgatagatt tccggctct ggaagcggca ccgacttcac cctgaagatc       240
agcaaggtgg aaaccgagga cgtgggcgtg tactattgcg cccagttcct ggaataccccc     300 cccacctttg gcagcggcac caagctggaa atcaag                                336

<210> SEQ ID NO 40
<211> LENGTH: 336
<212> TYPE: DNA
<213> ORGANISM: Artificial Sequence
<220> FEATURE:
<223> OTHER INFORMATION: Rat VLd

<400> SEQUENCE: 40
gatattgtgt tgactcaagc tccacgctct gtatctgtca ctcctggaga gtcagcttcc       60
atctcctgca ggtctaataa gagtcgactg agtaggatgg gcatcactcc cttgaattgg      120
taccttcaga agccaggaaa gtctcctcag ctcctgatat atcggatgtc caaccttgcc      180
tcaggagttc cagacaggtt tagtggcagt gggtcagaaa cagattttac actgaaaatc      240
agtaaggtgg agactgagga tgttggcgtt tattactgtg cacagttct agaatatcct       300 cctacgttcg gttctgggac caagctggag atcaaa                                336

<210> SEQ ID NO 41
<211> LENGTH: 54
<212> TYPE: DNA
<213> ORGANISM: Artificial Sequence
<220> FEATURE:
<223> OTHER INFORMATION: Humanized Whitlow d

<400> SEQUENCE: 41
ggcagcacaa gcggctctgg caaacctgga tctggcgagg gcagcaccaa gggc             54

<210> SEQ ID NO 42
<211> LENGTH: 54
<212> TYPE: DNA
<213> ORGANISM: Artificial Sequence
<220> FEATURE:
<223> OTHER INFORMATION: Rat Whitlow d

<400> SEQUENCE: 42
ggcagcacca gcggctccgg caagcctggc tctggcgagg gcagcacaaa ggga             54

<210> SEQ ID NO 43
```

<211> LENGTH: 711
<212> TYPE: DNA
<213> ORGANISM: Artificial Sequence
<220> FEATURE:
<223> OTHER INFORMATION: Humanized IgG1 spacer d

<400> SEQUENCE: 43

```
cccgccgagc caagagccc cgacaagacc catacctgcc ctccatgtcc tgcccctcca    60
gtggctggcc ctagcgtgtt cctgttcccc ccaaagccca aggacaccct gatgatcgcc   120
cggaccctg aagtgacctg cgtggtggtg gatgtgtccc acgaggatcc cgaagtgaag    180
ttcaattggt acgtggacgg cgtggaagtg cacaacgcca agaccaagcc cagagaggaa   240
cagtacaaca gcacctaccg ggtggtgtct gtgctgaccg tgctgcatca ggactggctg   300
aacggcaaag agtacaagtg caaggtgtcc aacaaggccc tgcctgcccc catcgagaaa   360
accatctcca aggccaaggg acagccccgc gagcccagg tgtacacact gcctccaagc   420
agggacgagc tgaccaagaa ccaggtcagc ctgacctgcc tggtcaaagg cttctatccc   480
agcgacatcg ccgtggagtg ggagagcaat gggcagccgg agaacaacta caagaccacg   540
cctcccgtgc tggactccga cggctccttc ttcctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaaa aagatcccaa a            711
```

<210> SEQ ID NO 44
<211> LENGTH: 711
<212> TYPE: DNA
<213> ORGANISM: Artificial Sequence
<220> FEATURE:
<223> OTHER INFORMATION: Rat IgG1 spacer d

<400> SEQUENCE: 44

```
cctgccgagc ctaagagccc cgacaagacc cacacctgtc cccttgtcc tgcccctcca    60
gtggctggcc ctagcgtgtt cctgttcccc ccaaagccca aggataccct gatgatcgcc   120
cggaccccg aagtcacatg cgtggtggtg gacgtgagcc acgaagaccc tgaggtcaag    180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaggg gcagcccga gaaccacagg tgtacaccct gcccccatcc   420
cgggatgagc tgaccaagaa ccaggtcagc ctgacctgcc tggtcaaagg cttctatccc   480
agcgacatcg ccgtggagtg ggagagcaat gggcagccgg agaacaacta caagaccacg   540
cctcccgtgc tggactccga cggctccttc ttcctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaaa aagatcccaa a            711
```

<210> SEQ ID NO 45
<211> LENGTH: 265
<212> TYPE: DNA
<213> ORGANISM: Artificial Sequence
<220> FEATURE:
<223> OTHER INFORMATION: Humanized IgG1 delta spacer d

<400> SEQUENCE: 45

```
ccaggtgtcc ctgacctgcc tcgtgaaggg cttctacccc tccgatatcg ccgtggaatg    60
ggagagcaat ggccagcccg agaacaacta caagaccacc cccctgtgc tggacagcga   120
```

```
cggctcattc ttcctgtaca gcaagctgac agtggacaag agccggtggc agcagggcaa      180
cgtgttcagc tgcagcgtga tgcacgaggc tctgcacaac cactacaccc agaagtccct      240
gagcagcctg agcccaggca agaag                                            265
```

<210> SEQ ID NO 46
<211> LENGTH: 440
<212> TYPE: DNA
<213> ORGANISM: Artificial Sequence
<220> FEATURE:
<223> OTHER INFORMATION: Rat IgG1 delta spacer d

<400> SEQUENCE: 46

```
cctgccgagc ctaagagccc cgacaagacc cacacctgtc cccttgtcc tgcccctcca       60 gtggctggcc ctagcgtgtt cctgttcccc ccaaagccca aggatacct gatgatcgcc       120 cggaccccccg aagtcacatg cgtggtggtg gacgtgagcc acgaagaccc tgaggtcaag     180
ttcaactggt acgtggacgg cgtggaggtg cataatgcca agacaaagcc gcgggaggag     240
cagtacaaca gcacgtaccg tgtggtcagc gtcctcaccg tcctgcacca ggactggctg      300
aatggcaagg agtacaagtg caaggtctcc aacaaagccc tcccagcccc catcgagaaa     360
accatctcca agccaaagg gcagccccga gaaccacagg tgtacaccct gccccatcc       420 cgggatgagc tgaccaagaa                                                  440
```

<210> SEQ ID NO 47
<211> LENGTH: 72
<212> TYPE: DNA
<213> ORGANISM: Artificial Sequence
<220> FEATURE:
<223> OTHER INFORMATION: transmembrane domain CD8 alpha d

<400> SEQUENCE: 47

```
atctacatct gggcccctct ggccggcacc tgtggcgtgc tgctgctgtc tctcgtgatc      60
acactgtact gc                                                          72
```

<210> SEQ ID NO 48
<211> LENGTH: 81
<212> TYPE: DNA
<213> ORGANISM: Artificial Sequence
<220> FEATURE:
<223> OTHER INFORMATION: transmembrane domain CD28 d

<400> SEQUENCE: 48

```
ttttgggtgc tggtggtggt tggtggagtc ctggcttgct atagcttgct agtaacagtg      60
gcctttatta ttttctgggt g                                                81
```

<210> SEQ ID NO 49
<211> LENGTH: 126
<212> TYPE: DNA
<213> ORGANISM: Artificial Sequence
<220> FEATURE:
<223> OTHER INFORMATION: Co-stimulatory domain 4-1BB d

<400> SEQUENCE: 49

```
aagcggggca gaaagaagct gctgtacatc ttcaagcagc ccttcatgcg gcccgtgcag      60
accacccagg aagaggacgg ctgctcctgc agattccccg aggaagaaga aggcggctgc     120
gagctg                                                                 126
```

<210> SEQ ID NO 50

```
<211> LENGTH: 126
<212> TYPE: DNA
<213> ORGANISM: Artificial Sequence
<220> FEATURE:
<223> OTHER INFORMATION: Co-stimulatory domain CD28 d

<400> SEQUENCE: 50
aggagtaaga ggagcaggct cctgcacagt gactacatga acatgactcc ccgccgcccc    60
gggcccaccc gcaagcatta ccagccctat gccccaccac gcgacttcgc agcctatcgc   120
tccctg                                                              126

<210> SEQ ID NO 51
<211> LENGTH: 342
<212> TYPE: DNA
<213> ORGANISM: Artificial Sequence
<220> FEATURE:
<223> OTHER INFORMATION: Activation domain CD3 zeta (4-1BB) d

<400> SEQUENCE: 51
ctgcgcgtga agttttctag aagcgccgac gcccctgcct accagcaggg ccagaaccag    60
ctgtacaacg agctgaacct gggcagacgg aagagtacg acgtgctgga taagcggaga   120
ggccgggacc ctgagatggg cggcaagcct agaagaaaga cccccagga aggcctgtat    180 aacgaactgc agaaagacaa gatggccgag gcctacagcg agatcggaat gaagggcgag    240
cggagaagag gcaagggcca cgatggactg taccagggcc tgagcaccgc caccaaggac    300
acctatgacg cccctgcacat gcaggctctg ccccccagat aa                     342

<210> SEQ ID NO 52
<211> LENGTH: 339
<212> TYPE: DNA
<213> ORGANISM: Artificial Sequence
<220> FEATURE:
<223> OTHER INFORMATION: Activation domain CD3 zeta (CD28) d

<400> SEQUENCE: 52
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240 cggagggca aggggcacga tggcctttac cagggtctca gtacagccac caaggacacc    300
tacgacgccc ttcacatgca ggccctgccc cctcgctga                          339

<210> SEQ ID NO 53
<211> LENGTH: 333
<212> TYPE: DNA
<213> ORGANISM: Artificial
<220> FEATURE:
<223> OTHER INFORMATION: hHC

<400> SEQUENCE: 53
gaggtgcagc tggtggagag cggcggcggc ctggtgcagc ccggcggcag cctgaggctg     60
agctgcgccg ccagcggctt caccttcagc accagcggca tgaactggtt caggcaggcc    120
cccggcaagg gcctggagtg ggtgagctac atcagcagca gcgcggcctt cgtgtacgcc    180
gacagcgtga agggcaggtt caccatcagc agggacaacg cccagaacag cctgtacctg    240
cagatgaaca gcctgagggc cgaggacacc gccgtgtact actgcgccag gagcgaggcc    300
gccttctggg gccagggcac cctggtgacc gtg                                 333
```

<210> SEQ ID NO 54
<211> LENGTH: 336
<212> TYPE: DNA
<213> ORGANISM: Artificial
<220> FEATURE:
<223> OTHER INFORMATION: hLC

<400> SEQUENCE: 54

```
gacatcgtgc tgacccagag ccccgcagc ctgcccgtga cccccggcga gcccgccagc      60
atcagctgca ggtcctccaa gtccaggctg agcaggatgg catcacccc cctgaactgg     120 tacctgcaga agcccggcca gagccccag ctgctgatct acaggatgag caacagggcc     180
agcggcgtgc ccgacaggtt cagcggcagc ggcagcggca ccgacttcac cctgaagatc     240
agcaaggtgg agaccgagga cgtgggcgtg tactactgcg cccagttcct ggagtacccc     300
cccaccttcg gcagcggcac caagctggag atcaag                              336
```

<210> SEQ ID NO 55
<211> LENGTH: 113
<212> TYPE: PRT
<213> ORGANISM: Rattus norvegicus

<400> SEQUENCE: 55

```
Glu Val Gln Leu Val Glu Ser Gly Gly Gly Leu Val Gln Pro Gly Lys
1               5                   10                  15

Ser Leu Lys Leu Ser Cys Ser Ala Ser Gly Phe Thr Phe Ser Thr Ser
            20                  25                  30

Gly Met His Trp Phe Arg Gln Ala Pro Gly Lys Gly Leu Asp Trp Val
        35                  40                  45

Ala Tyr Ile Ser Ser Ser Ser Gly Phe Val Tyr Ala Asp Ala Val Lys
    50                  55                  60

Gly Arg Phe Thr Ile Ser Arg Asp Asn Ala Gln Asn Thr Leu Tyr Leu
65                  70                  75                  80

Gln Leu Asn Ser Leu Lys Ser Glu Asp Thr Ala Ile Tyr Tyr Cys Ala
                85                  90                  95

Arg Ser Glu Ala Ala Phe Trp Gly Gln Gly Thr Leu Val Thr Val Ser
            100                 105                 110

Ser
```

<210> SEQ ID NO 56
<211> LENGTH: 113
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (16)..(16)
<223> OTHER INFORMATION: X is Lys or Gly
<220> FEATURE:
<221> NAME/KEY: VARIANT
<222> LOCATION: (19)..(19)
<223> OTHER INFORMATION: X is Lys or Arg
<220> FEATURE:
<221> NAME/KEY: VARIANT
<222> LOCATION: (22)..(22)
<223> OTHER INFORMATION: X is Ser or Ala
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: VARIANT

```
<222> LOCATION: (35)..(35)
<223> OTHER INFORMATION: X is His or Asn
<220> FEATURE:
<221> NAME/KEY: VARIANT
<222> LOCATION: (46)..(46)
<223> OTHER INFORMATION: X is Asp ro Glu
<220> FEATURE:
<221> NAME/KEY: VARIANT
<222> LOCATION: (49)..(49)
<223> OTHER INFORMATION: X is Ala or Ser
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: VARIANT
<222> LOCATION: (77)..(77)
<223> OTHER INFORMATION: X is Thr or Ser
<220> FEATURE:
<221> NAME/KEY: VARIANT
<222> LOCATION: (82)..(82)
<223> OTHER INFORMATION: X is Leu or Met
<220> FEATURE:
<221> NAME/KEY: VARIANT
<222> LOCATION: (86)..(86)
<223> OTHER INFORMATION: X is Lys or Arg
<220> FEATURE:
<221> NAME/KEY: VARIANT
<222> LOCATION: (87)..(87)
<223> OTHER INFORMATION: X is Ser or Ala
<220> FEATURE:
<221> NAME/KEY: VARIANT
<222> LOCATION: (92)..(92)
<223> OTHER INFORMATION: X is Ile or Val

<400> SEQUENCE: 56

Glu Val Gln Leu Val Glu Ser Gly Gly Gly Leu Val Gln Pro Gly Xaa
1               5                   10                  15

Ser Leu Xaa Leu Ser Cys Xaa Ala Ser Gly Phe Thr Phe Ser Thr Ser
            20                  25                  30

Gly Met Xaa Trp Phe Arg Gln Ala Pro Gly Lys Gly Leu Xaa Trp Val
        35                  40                  45

Xaa Tyr Ile Ser Ser Ser Ser Gly Phe Val Tyr Ala Asp Xaa Val Lys
50                  55                  60

Gly Arg Phe Thr Ile Ser Arg Asp Asn Ala Gln Asn Xaa Leu Tyr Leu
65                  70                  75                  80

Gln Xaa Asn Ser Leu Xaa Xaa Glu Asp Thr Ala Xaa Tyr Tyr Cys Ala
            85                  90                  95

Arg Ser Glu Ala Ala Phe Trp Gly Gln Gly Thr Leu Val Thr Val Ser
            100                 105                 110

Ser

<210> SEQ ID NO 57
<211> LENGTH: 113
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

Gly Met Asn Trp Phe Arg Gln Ala Pro Gly Lys Gly Leu Glu Trp Val
        35                  40                  45

Ser Tyr Ile Ser Ser Ser Ser Gly Phe Val Tyr Ala Asp Ser Val Lys
50                  55                  60
```

```
Gly Arg Phe Thr Ile Ser Arg Asp Asn Ala Gln Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ser Glu Ala Ala Phe Trp Gly Gln Gly Thr Leu Val Thr Val Ser
            100                 105                 110

Ser

<210> SEQ ID NO 58
<211> LENGTH: 112
<212> TYPE: PRT
<213> ORGANISM: Rattus norvegicus

<400> SEQUENCE: 58

Asp Ile Val Leu Thr Gln Ala Pro Arg Ser Val Ser Val Thr Pro Gly
1               5                   10                  15

Glu Ser Ala Ser Ile Ser Cys Arg Ser Asn Lys Ser Arg Leu Ser Arg
            20                  25                  30

Met Gly Ile Thr Pro Leu Asn Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: X is Val or Leu
<220> FEATURE:
<221> NAME/KEY: VARIANT
<222> LOCATION: (12)..(12)
<223> OTHER INFORMATION: X is Ser or Pro
<220> FEATURE:
<221> NAME/KEY: VARIANT
<222> LOCATION: (18)..(18)
<223> OTHER INFORMATION: X is Ser or Pro
<220> FEATURE:
<221> NAME/KEY: VARIANT
<222> LOCATION: (26)..(26)
<223> OTHER INFORMATION: X is Asn or Ser
<220> FEATURE:
<221> NAME/KEY: VARIANT
<222> LOCATION: (47)..(47)
<223> OTHER INFORMATION: X is Lys or Gln
<220> FEATURE:
<221> NAME/KEY: VARIANT
<222> LOCATION: (59)..(59)
<223> OTHER INFORMATION: X is Leu or Arg
<220> FEATURE:
<221> NAME/KEY: VARIANT
<222> LOCATION: (73)..(73)
```

<223> OTHER INFORMATION: X is Glu or Gly

<400> SEQUENCE: 59

Asp Ile Val Leu Thr Gln Xaa Pro Arg Ser Xaa Xaa Val Thr Pro Gly
1               5                   10                  15

Glu Xaa Ala Ser Ile Ser Cys Arg Ser Xaa Lys Ser Arg Leu Ser Arg
            20                  25                  30

Met Gly Ile Thr Pro Leu Asn Trp Tyr Leu Gln Lys Pro Gly Xaa Ser
        35                  40                  45

Pro Gln Leu Leu Ile Tyr Arg Met Ser Asn Xaa Ala Ser Gly Val Pro
    50                  55                  60

Asp Arg Phe Ser Gly Ser Gly Ser Xaa Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 60
<211> LENGTH: 112
<212> TYPE: PRT
<213> ORGANISM: Homo sapiens

<400> SEQUENCE: 60

Asp Ile Val Leu Thr Gln Ser Pro Arg Ser Leu Pro Val Thr Pro Gly
1               5                   10                  15

Glu Pro Ala Ser Ile Ser Cys Arg Ser Ser Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 61
<211> LENGTH: 333
<212> TYPE: DNA
<213> ORGANISM: Artificial Sequence
<220> FEATURE:
<223> OTHER INFORMATION: antibody sequence

<400> SEQUENCE: 61
gaggtgcagc tggtggagag cggcggcggc ctggtgcagc ccggcggcag cctgaggctg      60
agctgcgccg ccagcggctt caccttcagc accagcggca tgaactggtt caggcaggcc    120
cccggcaagg gcctggagtg ggtgagctac atcagcagca gcagcggctt cgtgtacgcc    180
gacagcgtga aggcaggtt caccatcagc agggacaacg cccagaacag cctgtacctg     240
cagatgaaca gcctgagggc cgaggacacc gccgtgtact actgcgccag gagcgaggcc    300
gccttctggg gccagggcac cctggtgacc gtg                                 333

<210> SEQ ID NO 62
<211> LENGTH: 333

```
<212> TYPE: DNA
<213> ORGANISM: Artificial Sequence
<220> FEATURE:
<223> OTHER INFORMATION: antibody sequence

<400> SEQUENCE: 62
gaggtgcagc tggtggaatc tggcggagga ctggtgcagc ctggcggctc tctgagactg      60
tcttgtgccg ccagcggctt caccttcagc accagcggca tgaactggtt cagacaggcc     120
cctggcaagg gcctggaatg ggtgtcctac atcagcagca gctccggctt cgtgtacgcc     180
gacagcgtga agggccggtt caccatcagc agagacaacg cccagaacag cctgtacctg     240
cagatgaact ccctgcgggc cgaggacacc gccgtgtact actgtgccag aagcgaggcc     300
gccttttggg gccagggaac actcgtgaca gtg                                  333

<210> SEQ ID NO 63
<211> LENGTH: 336
<212> TYPE: DNA
<213> ORGANISM: Artificial Sequence
<220> FEATURE:
<223> OTHER INFORMATION: antibody sequence

<400> SEQUENCE: 63
gacatcgtgc tgacccagag cccccgcagc ctgcccgtga cccccggcga gcccgccagc      60
atcagctgca ggtcctccaa gtccaggctg agcaggatgg gcatcacccc cctgaactgg     120
tacctgcaga gcccggcca gagcccccag ctgctgatct acaggatgag caacagggcc     180
agcggcgtgc ccgacaggtt cagcggcagc ggcagcggca ccgacttcac cctgaagatc     240
agcaaggtgg agaccgagga cgtgggcgtg tactactgcg cccagttcct ggagtacccc     300
cccaccttcg gcagcggcac caagctggag atcaag                              336

<210> SEQ ID NO 64
<211> LENGTH: 336
<212> TYPE: DNA
<213> ORGANISM: Artificial Sequence
<220> FEATURE:
<223> OTHER INFORMATION: antibody sequence

<400> SEQUENCE: 64
gatatcgtgc tgacccagag ccccagatcc ctgcctgtga cacctggcga gcctgccagc      60
atcagctgca aagcagcaa gagccggctg agccggatgg gcatcacccc cctgaactgg     120
tatctgcaga acccggcca gtcccccag ctgctgatct accggatgag caacagagcc     180
agcggcgtgc ccgatagatt ttccggctct ggaagcggca ccgacttcac cctgaagatc     240
agcaaggtgg aaaccgagga cgtgggcgtg tactattgcg cccagttcct ggaataccc     300 cccacctttg gcagcggcac caagctggaa atcaag                              336
```